United States Patent [19]

Wilson et al.

[11] Patent Number: 5,652,224
[45] Date of Patent: Jul. 29, 1997

[54] METHODS AND COMPOSITIONS FOR GENE THERAPY FOR THE TREATMENT OF DEFECTS IN LIPOPROTEIN METABOLISM

[75] Inventors: James M. Wilson, Gladwyne; Karen Kozarsky, Philadelphia; Jerome Strauss, III, Wyndmoor, all of Pa.

[73] Assignee: The Trustees of the University of Pennsylvania, Philadelphia, Pa.

[21] Appl. No.: 393,734

[22] Filed: Feb. 24, 1995

[51] Int. Cl.$^6$ .............................. A61K 48/00; C12N 15/00
[52] U.S. Cl. .................. 514/44; 424/93.21; 435/172.3; 435/320.1; 435/325; 435/354; 435/366; 435/369; 435/370
[58] Field of Search .................. 424/93.21; 435/320.1, 435/240.2, 172.3, 240.1; 514/44, 2; 536/22.1; 530/350

[56] References Cited

U.S. PATENT DOCUMENTS

| | | | |
|---|---|---|---|
| 4,658,019 | 4/1987 | Kung et al. | 530/388.75 |
| 5,017,691 | 5/1991 | Lee et al. | 530/351 |
| 5,166,320 | 11/1992 | Wu et al. | 530/395 |
| 5,240,846 | 8/1993 | Collins et al. | 435/240.1 |

FOREIGN PATENT DOCUMENTS

| | | |
|---|---|---|
| 501233 | 9/1992 | European Pat. Off. . |
| 555880 | 8/1993 | European Pat. Off. . |
| WO90/05147 | 5/1990 | WIPO . |
| WO91/18088 | 11/1991 | WIPO . |
| WO93/00431 | 1/1993 | WIPO . |
| 9410322 | 5/1994 | WIPO . |
| WO94/12649 | 6/1994 | WIPO . |
| WO94/17832 | 8/1994 | WIPO . |
| WO95/06743 | 3/1995 | WIPO . |
| WO95/13374 | 5/1995 | WIPO . |

OTHER PUBLICATIONS

Hodgson, Exp. Opin. Ther. Pat., 5(5):459–468, 1995.
Oka et al, Eur. J. Biochem., 224, 1994, 975–982.
Herz et al. (See Foreign Documents).
Marshall, Science, 269, 1995, 1050–1055.
Miller, FASEB Journal, 9, 1995, 190–199.
Culver et al., TIG, 10(5), 1994, 174–178.
Neve, Trends. Neurosci, 16(7), 1993, 251–253.
J. Webb et al, "Characterization and Tissue-Specific Expression of the Human 'Very Low Density Lipoprotein (VLDL) Receptor' mRNA", Human Molecular Genetics, 3(4):531–537 (1994).
J. Wilson, "Cystic Fibrosis—Vehicles for Gene Therapy", Nature, 365:691–692 (Oct. 21, 1993) [Wilson I].
J. Wilson et al, "Correction of the Genetic Defect in Hepatocytes from the Watanabe Heritable Hyperlipidemic Rabbit", Proc. Natl. Acad. Sci. USA, 85:4421–4425 (Jun., 1988) [Wilson II].

J. Wilson et al, "Research Article—Transplantation of Allogeneic Hepatocytes into LDL Receptor Deficient Rabbits Leads to Transient Improvement in Hypercholesterolemia", Clin. Bio., 3:21–26 (Spring, 1991) [Wilson III].
J. Wilson et al, "A Novel Mechanism for Achieving Transgene Persistence in vivo after Somatic Gene Transfer into Hepatocytes", J. Biol. Chem., 267(16):11483–11489 (Jun. 5, 1992) [Wilson IV].
K. Kozarsky et al, "In Vivo Correction of Low Density Lipoprotein Receptor Deficiency in the Watanabe Heritable Hyperlipidemic Rabbit with Recombinant Adenoviruses", J. Biol. Chem., 269(18):13695–13702 (May 6, 1994) [Kozarsky I].
K. Kozarsky et al, "Adenovirus-Mediated Correction of the Genetic Defect in Hepatocytes from Patients with Familial Hypercholesterolemia", Somatic Cell and Molecular Genetics, 19(5):449–458 (Sep., 1993) [Kozarsky II].
K. Kozarsky et al, "Gene Therapy: Adenovirus Vectors", Curr. Opin. Genet. Devel., 3:499–503 (Mar., 1993) [Kozarsky III].
Y. Yang et al, "MHC Class I–Restricted Cytotoxic T Lymphocytes to Viral Antigens Destroy Hepatocytes in Mice Infected with E1–Deleted Recombinant Adenoviruses", Immunity, 1:433–442 (Aug., 1994) [Yang I].
Y. Yang et al, "Cellular Immunity to Viral Antigens Limits E1-Deleted Adenoviruses for Gene Therapy", Proc. Natl. Acad. Sci. USA, 91:4407–4411 (May, 1994) [Yang II].
Y. Yang et al, "Inactivation of E2a in Recombinant Adenoviruses Improves the Prospect for Gene Therapy in Cystic Fibrosis", Nature Genetics, 7:362–369 (Jul., 1994) [Yang III].
J. Goldstein et al, "Familial Hypercholesterolemia", in The Metabolic Basis of Inherited Disease, Chapter 48, 6th ed., C.R. Scrivers et al (eds), McGraw-Hill Information Services Co., New York, pp. 1215–1250 (1989) [Goldstein I].
J. Goldstein et al, "Defective Lipoprotein Receptors and Atherosclerosis—Lessons from an Animal Counterpart of Familial Hypercholesterolemia", New Engl. J. Med., 309(5):288–296 (Aug. 4, 1983) [Goldstein II].

(List continued on next page.)

Primary Examiner—Jacqueline M. Stone
Assistant Examiner—Andrew Milne
Attorney, Agent, or Firm—Howson and Howson

[57] ABSTRACT

The invention provides a recombinant viral vector comprising the DNA of, or corresponding to, at least a portion of the genome of an adenovirus, which portion is capable of infecting a hepatic cell; and a human VLDL receptor gene operatively linked to regulatory sequences directing its expression. The vector is capable of expressing the normal VLDL receptor gene product in hepatic cells in vivo or in vitro. This viral vector is useful in the treatment of metabolic disorders caused by the accumulation of LDL in plasma, such as familial hypercholesterolemia or familial combined hyperlipidemia.

13 Claims, 29 Drawing Sheets

OTHER PUBLICATIONS

J. Goldstein et al, "Disorders of the Biogenesis and Secretion of Lipoproteins", in *The Metabolic Basis of Inherited Disease*, Chapter 44B, 6th ed., C.R. Scrivers et al (eds), McGraw–Hill Information Services Co., New York, pp. 1155–1156 (1989) [Goldstein III].

S. Ishibashi et al, "Hypercholesterolemia in Low Density Lipoprotein Receptor Knockout Mice and its Reversal by Adenovirus–Mediated Gene Delivery", *J. Clin. Invest.*, 92:883–893 (Aug., 1993) [Ishibashi I].

S. Ishibashi et al, "Massive Xanthomatosis and Atherosclerosis in Cholesterol–fed Low Density Lipoprotein Receptor–negative Mice", *J. Clin. Invest.*, 93:1885–1893 (May, 1994) [Ishibashi II].

M. Gafvels et al, "Cloning of a cDNA Encoding a Putative Human Very Low Density Lipoprotein/Apolipoprotein E Receptor and Assignment of the Gene to Chromosome 9pter–p266", *Somatic Cell and Molecular Genetics*, 19(6):557–569 (Sep., 1993) [Gafvels I].

M. Gafvels et al, "Cloning of a Complementary Deoxyribonucleic Acid Encoding the Murine Homolog of the Very Low Density Lipoprotein/Apolipoprotein–E Receptor: Expression Pattern and Assignment of the Gene to Mouse Chromosome 19", *Endocrinology*, 135(1):387–394 (Jul., 1994) [Gafvels II].

S. Takahashi et al, "Rabbit Very Low Density Lipoprotein Receptor: A Low Density Lipoprotein Receptor–Like Protein with Distinct Ligand Specificity", *Proc. Natl. Acad. Sci. USA*, 89:9252–9256 (Oct., 1992).

J. Engelhardt et al, "Ablation of E2A in Recombinant Adenoviruses Improves Transgene Persistence and Decreases Inflammatory Response in Mouse Liver", *Proc. Natl. Acad. Sci. USA*, 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.*, 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

Y. Watanabe, "Serial Inbreeding of Rabbits with Hereditary Hyperlipidemia (WHHL–Rabbit)", *Atherosclerosis*, 36:261–268 (1980).

K. Tanzawa et al, "WHHL–Rabbit: A Low Density Lipoprotein Receptor–Deficient Animal Model for Familial Hypercholesterolemia", *FEBS Letters*, 118(1):81–84 (Aug., 1980).

M Horwitz, "Adenoviridae and Their Replication", *Virology*, 2d edition, ed. B. N. Fields, Raven Press, Ltd., New York, Chapter 60, pp. 1679–1721 (1990).

M. Grossman et al, "Towards Liver–Directed Gene Therapy: Retrovirus–Mediated Gene Transfer into Human Hepatocytes", *Som. Cell. and Mol. Gen.*, 17(6):601–607 (Nov., 1991).

M. Boshart et al, "A Very Strong Enhancer is Located Upstream of an Immediate Early Gene of Human Cytomegalovirus", *Cell*, 41:521–530 (Jun., 1985).

C. Wu et al, "Targeting Genes: Delivery and Persistent Expression of a Foreign Gene Driven by Mammalian Regulatory Elements in vivo", *J. Biol. Chem.*, 264(29):16985–16987 (Oct. 15, 1989).

K. Fisher et al, "Biochemical and Functional Analysis of an Adenovirus–Based Ligand Complex for Gene Transfer", *Biochem. J.*, 299:49–58 (Apr. 1, 1994).

C. Laughlin et al, "Cloning of Infectious Adeno–associated Virus Genomes in Bacterial Plasmids", *Gene*, 23:65–73 (Jul., 1983).

J. Price et al, "Lineage Analysis in the Vertebrate Nervous System by Retrovirus–mediated Gene Transfer", *Proc. Natl. Acad. Sci. USA*, 84:156–160 (Jan., 1987).

T. Kost et al, "The Nucleotide Sequence of the Chick Cytoplasmid beta–actin Gene", *Nucl. Acids Res.*, 11(23):8287–8301 (Dec. 11, 1983).

J. Schreiber et al, "Recombinant Retroviruses Containing Novel Reporter Genes", *BioTechniques*, 14(5):818–823 (May, 1993).

J. Riordan et al, "Identification of the Cystic Fibrosis Gene: Cloning and Characterization of Complementary DNA", *Science*, 245:1066–1073 (Sep. 8, 1989).

M. Brown et al, "A Receptor–Mediated Pathway for Cholesterol Homeostasis", *Science*, 232:34–46 (Apr. 4, 1986).

T. Yamamato et al, "The Human LDL Receptor: A Cysteine–Rich Protein with Multiple Alu Sequences in its mRNA", *Cell*, 39:27–38 (Nov., 1984).

R. Samulski et al, "Helper–Free Stocks of Recombinant Adeno–Associated Viruses: Normal Integration does not Require Viral Gene Expression", *J. Virol.*, 63(9):3822–3828 (Sep., 1989).

T. Shenk et al, "Genetic Analysis of Adenoviruses", *Current Topics in Microbiol. and Immunol.*, 111:1–39 (1984).

P. Hearing et al, "Identification of a Repeated Sequence Element Required for Efficient Encapsidation of the Adenovirus Type 5 Chromosome", *J. Virol.*, 61(8):2555–2558 (Aug., 1987).

M. Grable et al, "Adenovirus Type 5 Packaging Domain is Composed of a Repeated Element that is Functionally Redundant", *J. Virol.*, 64(5):2047–2056 (May, 1990) [Grable I].

M. Grable et al, "cis and trans Requirements for the Selective Packaging of Adenovirus Type 5 DNA", *J. Virol.*, 66(2):723–731 (Feb., 1992) [Grable II].

F. Wittmaack et al, "Localization and Regulation of the Human Very Low Density Lipoprotein/Apolipoprotein–E Receptor: Trophoblast Expression Predicts a Role for the Receptor in Placental Lipid Transport", *Endocrinol.*, 136(1):340–348 (Jan., 1995).

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

J. Logan et al, "Adenovirus Tripartite Leader Sequence Enhances Translation of mRNAs Late After Infection", *Proc. Natl. Acad. Sci. USA*, 81:3655–3659 (Jun., 1984).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

P. Scott, "IL–12: Initiation Cytokine for Cell–Mediated Immunity", *Science*, 260:496–497 (Apr., 1993).

R. Manetti et al. "Natural Killer Cell Stimulatory Factor (Interleukin 12 [IL–12]) Induces T Helper Type 1 (Th1)–specific Immune Responses and Inhibits the Development of IL–4–Producing Th Cells", *J. Exp. Med.*, 177:1199–1204 (Apr., 1993).

A. D'Andrea et al, "Production of Natural Killer Cell Stimulatory Factor (Interleukin 12) by Peripheral Blood Mononuclear Cells", *J. Exp. Med.*, 176:1387–1398 (Nov., 1992).

S. Morris et al, "Effects of IL–12 on in Vivo Cytokine Gene Expression and Ig Isotype Selection", *J. Immunol.*, 152:1047–1056 (Feb., 1994).

F. Heinzel et al, "Recombinant Interleukin 12 Cures Mice Infected with Leishmania major", *J. Exp. Med.*, 177:1505–1509 (May, 1993).

T. Yokota et al, "Isolation and Characterization of a Human Interleukin cDNA Clone, Homologous to Mouse B–Cell Stimulatory Factor 1, that Expresses B–cell– and T–cell–Stimulating Activities", *Proc. Natl. Acad. Sci. USA*, 83:5894–5898 (Aug., 1986).

F. Durie et al, "The Role of CD40 in the Regulation of Humoral and Cell–Mediated Immunity", *Immunol. Today*, 15(9):406–410 (Sep., 1994).

J. Cohen, "Naked DNA Points Way to Vaccines", *Science*, 259:1691–1692 (Mar. 19, 1993).

K. Kozarsky et al, "Effective Treatment of Familial Hypercholesterolaemia in the Mouse Model Using Adenovirus–Mediated Transfer of the VLDL Receptor Gene", *Nature Genetics*, 13:54–62 (May, 1996).

P. Frykman et al, "Normal Plasma Lipoproteins and Fertility in Gene–Targeted Mice Homozygous for a Disruption in the Gene Encoding Very Low Density Lipoprotein Receptor", *Proc. Natl. Acad. Sci. USA*, 92:8453–8457 (Aug., 1995).

FIGURE 8A

```
CTCTGCGGGC CGCGGGTGCG GGTCGTCGCT ACCGGCTCTC TCCGTTCTGT           50

GCTCTCTTCT GCTCTCGGCT CCCCACCCCC TCTCCCTTCC CTCCTCTCCC          100

CTTGCCTCCC CTCCTCTGCA GCGCCTGCAT TATTTTCTGC CCGCAGCTCG          150

GCTTGCACTG CTGCTGCAGC CCGGGGAGGT GGCTGGGTGG GTGGGGAGGA          200

GACTGTGCAA GTTGTAGGGG AGGGGGTGCC CTCTTCTTCC CCGCTCCCTT          250

CCCCAGCCAA GTGGTTCCCC TCCTTCTCCC CCTTTCCCCT CCCAGCCCCC          300

ACCTTCTTCC TCTTTCGGAA GGGCTGGTAA CTTGTCGTGC GGAGCGAACG          350

GCGGCGGCGG CGGCGGCGGC GGCACCATCC AGGCGGGCAC C ATG GGC ACG       400
                                             Met Gly Thr
                                              1
```

| | | | | | | | | | | | | |
|---|---|---|---|---|---|---|---|---|---|---|---|---|
| TCC | GCG | CTC | TGG | GCC | GTC | TGG | CTG | CTG | CTC | GCG | CTG | TGC | TGG | 442 |
| Ser | Ala | Leu | Trp | Ala | Val | Trp | Leu | Leu | Leu | Ala | Leu | Cys | Trp |
|  | 5 |  |  |  | 10 |  |  |  |  | 15 |  |  |  |

```
TCC GCG CTC TGG GCC GTC TGG CTG CTG CTC GCG CTG TGC TGG         442
Ser Ala Leu Trp Ala Val Trp Leu Leu Leu Ala Leu Cys Trp
     5                   10                  15

GCG CCC CGG GAG AGC GGC GCC ACC GGA ACC GGG AGA AAA GCC         484
Ala Pro Arg Glu Ser Gly Ala Thr Gly Thr Gly Arg Lys Ala
         20                  25                  30

AAA TGT GAA CCC TCC CAA TTC CAG TGC ACA AAT GGT CGC TGT         526
Lys Cys Glu Pro Ser Gln Phe Gln Cys Thr Asn Gly Arg Cys
             35                  40                  45

ATT ACG CTG TTG TGG AAA TGT GAT GGG GAT GAA GAC TGT GTT         568
Ile Thr Leu Leu Trp Lys Cys Asp Gly Asp Glu Asp Cys Val
                 50                  55

GAC GGC AGT GAT GAA AAG AAC TGT GTA AAG AAG ACG TGT GCT         610
Asp Gly Ser Asp Glu Lys Asn Cys Val Lys Lys Thr Cys Ala
60                   65                  70

GAA TCT GAC TTC GTG TGC AAC AAT GGC CAG TGT GTT CCC AGC         652
Glu Ser Asp Phe Val Cys Asn Asn Gly Gln Cys Val Pro Ser
         75                  80                  85

CGA TGG AAG TGT GAT GGA GAT CCT GAC TGC GAA GAT GGT TCA         694
Arg Trp Lys Cys Asp Gly Asp Pro Asp Cys Glu Asp Gly Ser
             90                  95                  100

GAT GAA AGC CCA GAA CAG TGC CAT ATG AGA ACA TGC CGC ATA         736
Asp Glu Ser Pro Glu Gln Cys His Met Arg Thr Cys Arg Ile
                 105                 110                 115

CAT GAA ATC AGC TGT GGC GCC CAT TCT ACT CAG TGT ATC CCA         778
His Glu Ile Ser Cys Gly Ala His Ser Thr Gln Cys Ile Pro
                     120                 125
```

FIGURE 8B

| | | | | | | | | | | | | |
|---|---|---|---|---|---|---|---|---|---|---|---|---|
| GTG | TCC | TGG | AGA | TGT | GAT | GGT | GAA | AAT | GAT | TGT | GAC | AGT | GGA | 820 |
| Val | Ser | Trp | Arg | Cys | Asp | Gly | Glu | Asn | Asp | Cys | Asp | Ser | Gly | |
| 130 | | | | 135 | | | | | 140 | | | | | |

```
GTG TCC TGG AGA TGT GAT GGT GAA AAT GAT TGT GAC AGT GGA        820
Val Ser Trp Arg Cys Asp Gly Glu Asn Asp Cys Asp Ser Gly
130             135                 140

GAA GAT GAA GAA AAC TGT GGC AAT ATA ACA TGT AGT CCC GAC        862
Glu Asp Glu Glu Asn Cys Gly Asn Ile Thr Cys Ser Pro Asp
    145                 150                 155

GAG TTC ACC TGC TCC AGT GGC CGC TGC ATC TCC AGG AAC TTT        904
Glu Phe Thr Cys Ser Ser Gly Arg Cys Ile Ser Arg Asn Phe
        160                 165                 170

GTA TGC AAT GGC CAG GAT GAC TGC AGC GAT GGC AGT GAT GAG        946
Val Cys Asn Gly Gln Asp Asp Cys Ser Asp Gly Ser Asp Glu
            175                 180                 185

CTG GAC TGT GCC CCG CCA ACC TGT GGC GCC CAT GAG TTC CAG        988
Leu Asp Cys Ala Pro Pro Thr Cys Gly Ala His Glu Phe Gln
                190                 195

TGC AGC ACC TCC TCC TGC ATC CCC ATC AGC TGG GTA TGC GAC       1030
Cys Ser Thr Ser Ser Cys Ile Pro Ile Ser Trp Val Cys Asp
200                 205                 210

GAT GAT GCA GAC TGC TCC GAC CAA TCT GAT GAG TCC CTG GAG       1072
Asp Asp Ala Asp Cys Ser Asp Gln Ser Asp Glu Ser Leu Glu
    215                 220                 225

CAG TGT GGC CGT CAG CCA GTC ATA CAC ACC AAG TGT CCA GCC       1114
Gln Cys Gly Arg Gln Pro Val Ile His Thr Lys Cys Pro Ala
        230                 235                 240

AGC GAA ATC CAG TGC GGC TCT GGC GAG TGC ATC CAT AAG AAG       1156
Ser Glu Ile Gln Cys Gly Ser Gly Glu Cys Ile His Lys Lys
            245                 250                 255

TGG CGA TGT GAT GGG GAC CCT GAC TGC AAG GAT GGC AGT GAT       1198
Trp Arg Cys Asp Gly Asp Pro Asp Cys Lys Asp Gly Ser Asp
                260                 265

GAG GTC AAC TGT CCC TCT CGA ACT TGC CGA CCT GAC CAA TTT       1240
Glu Val Asn Cys Pro Ser Arg Thr Cys Arg Pro Asp Gln Phe
270                 275                 280

GAA TGT GAG GAT GGC AGC TGC ATC CAT GGC AGC AGG CAG TGT       1282
Glu Cys Glu Asp Gly Ser Cys Ile His Gly Ser Arg Gln Cys
    285                 290                 295

AAT GGT ATC CGA GAC TGT GTC GAT GGT TCC GAT GAA GTC AAC       1324
Asn Gly Ile Arg Asp Cys Val Asp Gly Ser Asp Glu Val Asn
        300                 305                 310

TGC AAA AAT GTC AAT CAG TGC TTG GGC CCT GGA AAA TTC AAG       1366
Cys Lys Asn Val Asn Gln Cys Leu Gly Pro Gly Lys Phe Lys
            315                 320                 325
```

FIGURE 8C

| | | | | | | | | | | | | |
|---|---|---|---|---|---|---|---|---|---|---|---|---|
| TGC | AGA | AGT | GGA | GAA | TGC | ATA | GAT | ATC | AGC | AAA | GTA | TGT AAC | 1408
| Cys | Arg | Ser | Gly | Glu | Cys | Ile | Asp | Ile | Ser | Lys | Val | Cys Asn |
| | | | 330 | | | | | 335 | | | | |

```
TGC AGA AGT GGA GAA TGC ATA GAT ATC AGC AAA GTA TGT AAC    1408
Cys Arg Ser Gly Glu Cys Ile Asp Ile Ser Lys Val Cys Asn
            330                 335

CAG GAG CAG GAC TGC AGG GAC TGG AGT GAT GAG CCC CTG AAA    1450
Gln Glu Gln Asp Cys Arg Asp Trp Ser Asp Glu Pro Leu Lys
340             345                 350

GAG TGT CAT ATA AAC GAA TGC TTG GTA AAT AAT GGT GGA TGT    1492
Glu Cys His Ile Asn Glu Cys Leu Val Asn Asn Gly Gly Cys
    355                 360             365

TCT CAT ATC TGC AAA GAC CTA GTT ATA GGC TAC GAG TGT GAC    1534
Ser His Ile Cys Lys Asp Leu Val Ile Gly Tyr Glu Cys Asp
        370             375                 380

TGT GCA GCT GGG TTT GAA CTG ATA GAT AGG AAA ACC TGT GGA    1576
Cys Ala Ala Gly Phe Glu Leu Ile Asp Arg Lys Thr Cys Gly
            385             390                 395

GAT ATT GAT GAA TGC CAA AAT CCA GGA ATC TGC AGT CAA ATT    1618
Asp Ile Asp Glu Cys Gln Asn Pro Gly Ile Cys Ser Gln Ile
                400             405

TGT ATC AAC TTA AAA GGC GGT TAC AAG TGT GAA TGT AGT CGT    1660
Cys Ile Asn Leu Lys Gly Gly Tyr Lys Cys Glu Cys Ser Arg
410             415                 420

GCC TAT CAA ATG GAT CTT GCT ACT GGC GTG TGC AAG GCA GTA    1702
Ala Tyr Gln Met Asp Leu Ala Thr Gly Val Cys Lys Ala Val
        425             430                 435

GGC AAA GAG CCA AGT CTG ATC TTC ACT AAT CGA AGA GAC ATC    1744
Gly Lys Glu Pro Ser Leu Ile Phe Thr Asn Arg Arg Asp Ile
            440             445                 450

AGG AAG ATT GGC TTA GAG AGG AAA GAA TAT ATC CAA CTA GTT    1786
Arg Lys Ile Gly Leu Glu Arg Lys Glu Tyr Ile Gln Leu Val
                455             460                 465

GAA CAG CTA AGA AAC ACT GTG GCT CTC GAT GCT GAC ATT GCT    1828
Glu Gln Leu Arg Asn Thr Val Ala Leu Asp Ala Asp Ile Ala
            470             475

GCC CAG AAA CTA TTC TGG GCC GAT CTA AGC CAA AAG GCT ATC    1870
Ala Gln Lys Leu Phe Trp Ala Asp Leu Ser Gln Lys Ala Ile
480             485                 490

TTC AGT GCC TCA ATT GAT GAC AAG GTT GGT AGA CAT GTT AAA    1912
Phe Ser Ala Ser Ile Asp Asp Lys Val Gly Arg His Val Lys
        495             500                 505

ATG ATC GAC AAT GTC TAT AAT CCT GCA GCC ATT GCT GTT GAT    1954
Met Ile Asp Asn Val Tyr Asn Pro Ala Ala Ile Ala Val Asp
            510             515                 520
```

FIGURE 8D

```
TGG GTG TAC AAG ACC ATC TAC TGG ACT GAT GCG GCT TCT AAG         1996
Trp Val Tyr Lys Thr Ile Tyr Trp Thr Asp Ala Ala Ser Lys
            525                 530                 535

ACT ATT TCA GTA GCT ACC CTA GAT GGA ACC AAG AGG AAG TTC         2038
Thr Ile Ser Val Ala Thr Leu Asp Gly Thr Lys Arg Lys Phe
            540                 545

CTG TTT AAC TCT GAC TTG CGA GAG CCT GCC TCC ATA GCT GTG         2080
Leu Phe Asn Ser Asp Leu Arg Glu Pro Ala Ser Ile Ala Val
550                 555                 560

GAC CCA CTG TCT GGC TTT GTT TAC TGG TCA GAC TGG GGT GAA         2122
Asp Pro Leu Ser Gly Phe Val Tyr Trp Ser Asp Trp Gly Glu
        565                 570                 575

CCA GCT AAA ATA GAA AAA GCA GGA ATG AAT GGA TTC GAT AGA         2164
Pro Ala Lys Ile Glu Lys Ala Gly Met Asn Gly Phe Asp Arg
            580                 585                 590

CGT CCA CTG GTG ACA GCG GAT ATC CAG TGG CCT AAC GGA ATT         2206
Arg Pro Leu Val Thr Ala Asp Ile Gln Trp Pro Asn Gly Ile
            595                 600                 605

ACA CTT GAC CTT ATA AAA AGT CGC CTC TAT TGG CTT GAT TCT         2248
Thr Leu Asp Leu Ile Lys Ser Arg Leu Tyr Trp Leu Asp Ser
                610                 615

AAG TTG CAC ATG TTA TCC AGC GTG GAC TTG AAT GGC CAA GAT         2290
Lys Leu His Met Leu Ser Ser Val Asp Leu Asn Gly Gln Asp
620                 625                 630

CGT AGG ATA GTA CTA AAG TCT CTG GAG TTC CTA GCT CAT CCT         2332
Arg Arg Ile Val Leu Lys Ser Leu Glu Phe Leu Ala His Pro
        635                 640                 645

CTT GCA CTA ACA ATA TTT GAG GAT CGT GTC TAC TGG ATA GAT         2374
Leu Ala Leu Thr Ile Phe Glu Asp Arg Val Tyr Trp Ile Asp
            650                 655                 660

GGG GAA AAT GAA GCA GTC TAT GGT GCC AAT AAA TTC ACT GGA         2416
Gly Glu Asn Glu Ala Val Tyr Gly Ala Asn Lys Phe Thr Gly
                665                 670                 675

TCA GAG CAT GCC ACT CTA GTC AAC AAC CTG AAT GAT GCC CAA         2458
Ser Glu His Ala Thr Leu Val Asn Asn Leu Asn Asp Ala Gln
                680                 685

GAC ATC ATT GTC TAT CAT GAA CTT GTA CAG CCA TCA GGT AAA         2500
Asp Ile Ile Val Tyr His Glu Leu Val Gln Pro Ser Gly Lys
690                 695                 700

AAT TGG TGT GAA GAA GAC ATG GAG AAT GGA GGA TGT GAA TAC         2545
Asn Trp Cys Glu Glu Asp Met Glu Asn Gly Gly Cys Glu Tyr
    705                 710                 715
```

FIGURE 8E

| | | | | | | | | | | | | |
|---|---|---|---|---|---|---|---|---|---|---|---|---|
| CTA | TGC | CTG | CCA | GCA | CCA | CAG | ATT | AAT | GAT | CAC | TCT | CCA | AAA | 2584 |
| Leu | Cys | Leu | Pro | Ala | Pro | Gln | Ile | Asn | Asp | His | Ser | Pro | Lys |
| | | 720 | | | | | 725 | | | | | 730 | |

```
CTA TGC CTG CCA GCA CCA CAG ATT AAT GAT CAC TCT CCA AAA          2584
Leu Cys Leu Pro Ala Pro Gln Ile Asn Asp His Ser Pro Lys
        720             725             730

TAT ACC TGT TCC TGT CCC AGT GGG TAC AAT GTA GAG GAA AAT          2626
Tyr Thr Cys Ser Cys Pro Ser Gly Tyr Asn Val Glu Glu Asn
        735             740                 745

GGC CGA GAC TGT CAA AGT ACT GCA ACT ACT GTG ACT TAC AGT          2668
Gly Arg Asp Cys Gln Ser Thr Ala Thr Thr Val Thr Tyr Ser
        750             755

GAG ACA AAA GAT ACG AAC ACA ACA GAA ATT TCA GCA ACT AGT          2710
Glu Thr Lys Asp Thr Asn Thr Thr Glu Ile Ser Ala Thr Ser
760             765             770

GGA CTA GTT CCT GGA GGG ATC AAT GTG ACC ACA GCA GTA TCA          2752
Gly Leu Val Pro Gly Gly Ile Asn Val Thr Thr Ala Val Ser
        775             780             785

GAG GTC AGT GTT CCC CCA AAA GGG ACT TCT GCC GCA TGG GCC          2794
Glu Val Ser Val Pro Pro Lys Gly Thr Ser Ala Ala Trp Ala
        790             795             800

ATT CTT CCT CTC TTG CTC TTA GTG ATG GCA GCA GTA GGT GGC          2836
Ile Leu Pro Leu Leu Leu Leu Val Met Ala Ala Val Gly Gly
        805             810             815

TAC TTG ATG TGG CGG AAT TGG CAA CAC AAG AAC ATG AAA AGC          2878
Tyr Leu Met Trp Arg Asn Trp Gln His Lys Asn Met Lys Ser
        820             825

ATG AAC TTT GAC AAT CCT GTG TAC TTG AAA ACC ACT GAA GAG          2920
Met Asn Phe Asp Asn Pro Val Tyr Leu Lys Thr Thr Glu Glu
830             835             840

GAC CTC TCC ATA GAC ATT GGT AGA CAC AGT GCT TCT GTT GGA          2962
Asp Leu Ser Ile Asp Ile Gly Arg His Ser Ala Ser Val Gly
        845             850             855

CAC ACG TAC CCA GCA ATA TCA GTT GTA AGC ACA GAT GAT GAT          3004
His Thr Tyr Pro Ala Ile Ser Val Val Ser Thr Asp Asp Asp
        860             865             870

CTA GCT TGACTTCTGT GACAAATGTT GACCTTTGAG GTCTAAACAA              3050
Leu Ala

ATAATACCCC CGTCGGAATG GTAACCGAGC CAGCAGCTGA AGTCTCTTTT           3100

TCTTCCTCTC GGCTGGAAGA ACATCAAGAT ACCTTTGCGT GGATCAAGCT           3150

TGCTGTACTT GACCGTTTTT ATATTACTTT TGTAAATATT CTTGTCCACA           3200

TTCTACTTCA GCTTTGGATG TGGTTACCGA GTATCTGTAA CCCTTGAATT           3250
```

FIGURE 8F

```
TCTAGACAGT ATTGCCACCT CTGGCCAAAT ATGCACTTTC CCTAGAAAGC        3300

CATATTCCAG CAGTGAAACT TGTGCTATAG TGTATACCAC CTGTACATAC        3350

ATTGTATAGG CCATCTGTAA ATATCCCAGA GAACAATCAC TATTCTTAAG        3400

CACTTTGAAA ATATTTCTAT GTAAATTATT GTAAACTTTT TCAATGGTTG        3450

GGACAATGGC AATAGGACAA AACGGGTTAC TAAGATGAAA TTGCCAAAAA        3500

AATTTATAAA CTAATTTTGG TACGTATGAA TGATATCTTT GACCTCAATG        3550

GAGGTTTGCA AGACTGAGT  GTTCAAACTA CTGTACATTT TTTTTCAAGT        3600

GCTAAAAAAT TAAACCAAGC AGCTTAAAAA AAAAAAAAAA AAAAAAAAA         3650

AAAAAA                                                        3656
```

FIGURE 9A

```
GAATTCGCTA GCATCATCAA TAATATACCT TATTTTGGAT TGAAGCCAAT ATGATAATGA
                                                                60

GGGGGTGGAG TTTGTGACGT GGCGCGGGGC GTGGGAACGG GGCGGGTGAC GTAGTAGTGT
                                                               120

GGCGGAAGTG TGATGTTGCA AGTGTGGCGG AACACATGTA AGCGACGGAT GTGGCAAAAG
                                                               180

TGACGTTTTT GGTGTGCGCC GGTGTACACA GGAAGTGACA ATTTTCGCGC GGTTTTAGGC
                                                               240

GGATGTTGTA GTAAATTTGG GCGTAACCGA GTAAGATTTG GCCATTTTCG CGGGAAAACT
                                                               300

GAATAAGAGG AAGTGAAATC TGAATAATTT TGTGTTACTC ATAGCGCGTA ATATTTGTCT
                                                               360

AGGGAGATCA GCCTGCAGGT CGTTACATAA CTTACGGTAA ATGGCCCGCC TGGCTGACCG
                                                               420

CCCAACGACC CCCGCCCATT GACGTCAATA ATGACGTATG TTCCCATAGT AACGCCAATA
                                                               480

GGGACTTTCC ATTGACGTCA ATGGGTGGAG TATTTACGGT AAACTGCCCA CTTGGCAGTA
                                                               540

CATCAAGTGT ATCATATGCC AAGTACGCCC CCTATTGACG TCAATGACGG TAAATGGCCC
                                                               600

GCCTGGCATT ATGCCCAGTA CATGACCTTA TGGGACTTTC CTACTTGGCA GTACATCTAC
                                                               660

GTATTAGTCA TCGCTATTAC CATGGTGATG CGGTTTTGGC AGTACATCAA TGGGCGTGGA
                                                               720

TAGCGGTTTG ACTCACGGGG ATTTCCAAGT CTCCACCCCA TTGACGTCAA TGGGAGTTTG
                                                               780

TTTTGGCACC AAAATCAACG GGACTTTCCA AAATGTCGTA ACAACTCCGC CCCATTGACG
                                                               840

CAAATGGGCG GTAGGCGTGT ACGGTGGGAG GTCTATATAA GCAGAGCTCT CTGGCTAACT
                                                               900

AGAGAACCCA CTGCTTAACT GGCTTATCGA AATTAATACG ACTCACTATA GGGAGACCCA
                                                               960

AGCTTCTCTG CGGGCCGCGG GTGCGGGTCG TCGCTACCGG CTCTCTCCGT TCTGTGCTCT
                                                              1020

CTTCTGCTCT CGGCTCCCCA CCCCCTCTCC CTTCCCTCCT CTCCCCTTGC CTCCCCTCCT
                                                              1080

CTGCAGCGCC TGCATTATTT TCTGCCCGCA GCTCGGCTTG CACTGCTGCT GCAGCCCGGG
                                                              1140
```

FIGURE 9B

```
GAGGTGGCTG GGTGGGTGGG GAGGAGACTG TGCAAGTTGT AGGGGAGGGG GTGCCCTCTT
                                                                1200
CTTCCCCGCT CCCTTCCCCA GCCAAGTGGT TCCCCTCCTT CTCCCCCTTT CCCCTCCCAG
                                                                1260
CCCCCACCTT CTTCCTCTTT CGGAAGGGCT GGTAACTTGT CGTGCGGAGC GAACGGCGGC
                                                                1320
GGCGGCGGCG GCGGCGGCAC CATCCAGGCG GGCACCATGG GCACGTCCGC GCTCTGGGCC
                                                                1380
GTCTGGCTGC TGCTCGCGCT GTGCTGGGCG CCCCGGGAGA GCGGCGCCAC CGGAACCGGG
                                                                1440
AGAAAAGCCA AATGTGAACC CTCCCAATTC CAGTGCACAA ATGGTCGCTG TATTACGCTG
                                                                1500
TTGTGGAAAT GTGATGGGGA TGAAGACTGT GTTGACGGCA GTGATGAAAA GAACTGTGTA
                                                                1560
AAGAAGACGT GTGCTGAATC TGACTTCGTG TGCAACAATG GCCAGTGTGT TCCCAGCCGA
                                                                1620
TGGAAGTGTG ATGGAGATCC TGACTGCGAA GATGGTTCAG ATGAAAGCCC AGAACAGTGC
                                                                1680
CATATGAGAA CATGCCGCAT ACATGAAATC AGCTGTGGCG CCCATTCTAC TCAGTGTATC
                                                                1740
CCAGTGTCCT GGAGATGTGA TGGTGAAAAT GATTGTGACA GTGGAGAAGA TGAAGAAAAC
                                                                1800
TGTGGCAATA TAACATGTAG TCCCGACGAG TTCACCTGCT CCAGTGGCCG CTGCATCTCC
                                                                1860
AGGAACTTTG TATGCAATGG CCAGGATGAC TGCAGCGATG GCAGTGATGA GCTGGACTGT
                                                                1920
GCCCCGCCAA CCTGTGGCGC CCATGAGTTC CAGTGCAGCA CCTCCTCCTG CATCCCCATC
                                                                1980
AGCTGGGTAT GCGACGATGA TGCAGACTGC TCCGACCAAT CTGATGAGTC CCTGGAGCAG
                                                                2040
TGTGGCCGTC AGCCAGTCAT ACACACCAAG TGTCCAGCCA GCGAAATCCA GTGCGGCTCT
                                                                2100
GGCGAGTGCA TCCATAAGAA GTGGCGATGT GATGGGGACC CTGACTGCAA GGATGGCAGT
                                                                2160
GATGAGGTCA ACTGTCCCTC TCGAACTTGC CGACCTGACC AATTTGAATG TGAGGATGGC
                                                                2220
AGCTGCATCC ATGGCAGCAG GCAGTGTAAT GGTATCCGAG ACTGTGTCGA TGGTTCCGAT
                                                                2280
```

FIGURE 9C

```
GAAGTCAACT GCAAAAATGT CAATCAGTGC TTGGGCCCTG GAAAATTCAA GTGCAGAAGT
                                                                2340

GGAGAATGCA TAGATATCAG CAAAGTATGT AACCAGGAGC AGGACTGCAG GGACTGGAGT
                                                                2400

GATGAGCCCC TGAAAGAGTG TCATATAAAC GAATGCTTGG TAAATAATGG TGGATGTTCT
                                                                2460

CATATCTGCA AAGACCTAGT TATAGGCTAC GAGTGTGACT GTGCAGCTGG GTTTGAACTG
                                                                2520

ATAGATAGGA AAACCTGTGG AGATATTGAT GAATGCCAAA ATCCAGGAAT CTGCAGTCAA
                                                                2580

ATTTGTATCA ACTTAAAAGG CGGTTACAAG TGTGAATGTA GTCGTGCCTA TCAAATGGAT
                                                                2640

CTTGCTACTG GCGTGTGCAA GGCAGTAGGC AAAGAGCCAA GTCTGATCTT CACTAATCGA
                                                                2700

AGAGACATCA GGAAGATTGG CTTAGAGAGG AAAGAATATA TCCAACTAGT TGAACAGCTA
                                                                2760

AGAAACACTG TGGCTCTCGA TGCTGACATT GCTGCCCAGA AACTATTCTG GCCGATCTA
                                                                2820

AGCCAAAAGG CTATCTTCAG TGCCTCAATT GATGACAAGG TTGGTAGACA TGTTAAAATG
                                                                2880

ATCGACAATG TCTATAATCC TGCAGCCATT GCTGTTGATT GGGTGTACAA GACCATCTAC
                                                                2940

TGGACTGATG CGGCTTCTAA GACTATTTCA GTAGCTACCC TAGATGGAAC CAAGAGGAAG
                                                                3000

TTCCTGTTTA ACTCTGACTT GCGAGAGCCT GCCTCCATAG CTGTGGACCC ACTGTCTGGC
                                                                3060

TTTGTTTACT GGTCAGACTG GGGTGAACCA GCTAAAATAG AAAAAGCAGG AATGAATGGA
                                                                3120

TTCGATAGAC GTCCACTGGT GACAGCGGAT ATCCAGTGGC CTAACGGAAT TACACTTGAC
                                                                3180

CTTATAAAAA GTCGCCTCTA TTGGCTTGAT TCTAAGTTGC ACATGTTATC CAGCGTGGAC
                                                                3240

TTGAATGGCC AAGATCGTAG GATAGTACTA AAGTCTCTGG AGTTCCTAGC TCATCCTCTT
                                                                3300

GCACTAACAA TATTTGAGGA TCGTGTCTAC TGGATAGATG GGGAAAATGA AGCAGTCTAT
                                                                3360

GGTGCCAATA AATTCACTGG ATCAGAGCAT GCCACTCTAG TCAACAACCT GAATGATGCC
                                                                3420
```

FIGURE 9D

```
CAAGACATCA TTGTCTATCA TGAACTTGTA CAGCCATCAG GTAAAAATTG GTGTGAAGAA
                                                            3480

GACATGGAGA ATGGAGGATG TGAATACCTA TGCCTGCCAG CACCACAGAT TAATGATCAC
                                                            3540

TCTCCAAAAT ATACCTGTTC CTGTCCCAGT GGGTACAATG TAGAGGAAAA TGGCCGAGAC
                                                            3600

TGTCAAAGTA CTGCAACTAC TGTGACTTAG AGACAAAAGA TACGAACACA ACAGAAATTT
                                                            3660

CAGCAACTAG TGGACTAGTT CCTGGAGGGA TCAATGTGAC CACAGCAGTA TCAGAGGTCA
                                                            3720

GTGTTCCCCC AAAAGGGACT TCTGCCGCAT GGGCCATTCT TCCTCTCTTG CTCTTAGTGA
                                                            3780

TGGCAGCAGT AGGTGGCTAC TTGATGTGGC GGAATTGGCA ACACAAGAAC ATGAAAAGCA
                                                            3840

TGAACTTTGA CAATCCTGTG TACTTGAAAA CCACTGAAGA GGACCTCTCC ATAGACATTG
                                                            3900

GTAGACACAG TGCTTCTGTT GGACACACGT ACCCAGCAAT ATCAGTTGTA AGCACAGATG
                                                            3960

ATGATCTAGC TTGACTTCTG TGACAAATGT TGACCTTTGA GGTCTAAACA AATAATACCC
                                                            4020

CCGTCGGAAT GGTAACCGAG CCAGCAGCTG AAGTCTCTTT TTCTTCCTCT CGGCTGGAAG
                                                            4080

AACATCAAGA TACCTTTGCG TGGATCAAGC TTGGTACCGA GCTCGGATCC ACTAGTAACG
                                                            4140

GCCGCCAGTG TGCTGGAATT CTGCAGATAT CCATCACACT GGCGGCCGCG GGATCCAGA
                                                            4200

CATGATAAGA TACATTGATG AGTTTGGACA AACCACAACT AGAATGCAGT GAAAAAAATG
                                                            4260

CTTTATTTGT GAAATTTGTG ATGCTATTGC TTTATTTGTA ACCATTATAA GCTGCAATAA
                                                            4320

ACAAGTTAAC AACAACAATT GCATTCATTT TATGTTTCAG GTTCAGGGGG AGGTGTGGGA
                                                            4380

GGTTTTTTCG GATCCTCTAG AGTCGACCTG CAGGCTGATC TGGAAGGTGC TGAGGTACGA
                                                            4440

TGAGACCCGC ACCAGGTGCA GACCCTGCGA GTGTGGCGGT AAACATATTA GGAACCAGCC
                                                            4500

TGTGATGCTG GATGTGACCG AGGAGCTGAG GCCCGATCAC TTGGTGCTGG CCTGCACCCG
                                                            4560
```

FIGURE 9E

```
CGCTGAGTTT GGCTCTAGCG ATGAAGATAC AGATTGAGGT ACTGAAATGT GTGGGCGTGG
                                                                4620

CTTAAGGGTG GGAAAGAATA TATAAGGTGG GGGTCTTATG TAGTTTTGTA TCTGTTTTGC
                                                                4680

AGCAGCCGCC GCCGCCATGA GCACCAACTC GTTTGATGGA AGCATTGTGA GCTCATATTT
                                                                4740

GACAACGCGC ATGCCCCCAT GGGCCGGGGT GCGTCAGAAT GTGATGGGCT CCAGCATTGA
                                                                4800

TGGTCGCCCC GTCCTGCCCG CAAACTCTAC TACCTTGACC TACGAGACCG TGTCTGGAAC
                                                                4860

GCCGTTGGAG ACTGCAGCCT CCGCCGCCGC TTCAGCCGCT GCAGCCACCG CCCGCGGGAT
                                                                4920

TGTGACTGAC TTTGCTTTCC TGAGCCCGCT TGCAAGCAGT GCAGCTTCCC GTTCATCCGC
                                                                4980

CCGCGATGAC AAGTTGACGG CTCTTTTGGC ACAATTGGAT TCTTTGACCC GGGAACTTAA
                                                                5040

TGTCGTTTCT CAGCAGCTGT TGGATCTGCG CCAGCAGGTT TCTGCCCTGA AGGCTTCCTC
                                                                5100

CCCTCCCAAT GCGGTTTAAA ACATAAATAA AAAACCAGAC TCTGTTTGGA TTTGGATCAA
                                                                5160

GCAAGTGTCT TGCTGTCTTT ATTTAGGGGT TTTGCGCGCG CGGTAGGCCC GGGACCAGCG
                                                                5220

GTCTCGGTCG TTGAGGGTCC TGTGTATTTT TTCCAGGACG TGGTAAAGGT GACTCTGGAT
                                                                5280

GTTCAGATAC ATGGGCATAA GCCCGTCTCT GGGGTGGAGG TAGCACCACT GCAGAGCTTC
                                                                5340

ATGCTGCGGG GTGGTGTTGT AGATGATCCA GTCGTAGCAG GAGCGCTGGG CGTGGTGCCT
                                                                5400

AAAAATGTCT TTCAGTAGCA AGCTGATTGC CAGGGGCAGG CCCTTGGTGT AAGTGTTTAC
                                                                5460

AAAGCGGTTA AGCTGGGATG GGTGCATACG TGGGGATATG AGATGCATCT TGGACTGTAT
                                                                5520

TTTTAGGTTG GCTATGTTCC CAGCCATATC CCTCCGGGGA TTCATGTTGT GCAGAACCAC
                                                                5580

CAGCACAGTG TATCCGGTGC ACTTGGGAAA TTTGTCATGT AGCTTAGAAG GAAATGCGTG
                                                                5640

GAAGAACTTG GAGACGCCCT TGTGACCTCC AAGATTTTCC ATGCATTCGT CCATAATGAT
                                                                5700
```

FIGURE 9F

```
GGCAATGGGC CCACGGGCGG CGGCCTGGGC GAAGATATTT CTGGGATCAC TAACGTCATA
                                                                5760

GTTGTGTTCC AGGATGAGAT CGTCATAGGC CATTTTTACA AAGCGCGGGC GGAGGGTGCC
                                                                5820

AGACTGCGGT ATAATGGTTC CATCCGGCCC AGGGGCGTAG TTACCCTCAC AGATTTGCAT
                                                                5880

TTCCCACGCT TTGAGTTCAG ATGGGGGAT CATGTCTACC TGCGGGGCGA TGAAGAAAAC
                                                                5940

GGTTTCCGGG GTAGGGAGA TCAGCTGGGA AGAAAGCAGG TTCCTGAGCA GCTGCGACTT
                                                                6000

ACCGCAGCCG GTGGGCCCGT AAATCACACC TATTACCGGG TGCAACTGGT AGTTAAGAGA
                                                                6060

GCTGCAGCTG CCGTCATCCC TGAGCAGGGG GGCCACTTCG TTAAGCATGT CCCTGACTCG
                                                                6120

CATGTTTTCC CTGACCAAAT CCGCCAGAAG GCGCTCGCCG CCCAGCGATA GCAGTTCTTG
                                                                6180

CAAGGAAGCA AAGTTTTTCA ACGGTTTGAG ACCGTCCGCC GTAGGCATGC TTTTGAGCGT
                                                                6240

TTGACCAAGC AGTTCCAGGC GGTCCCACAG CTCGGTCACC TGCTCTACGG CATCTCGATC
                                                                6300

CAGCATATCT CCTCGTTTCG CGGGTTGGGG CGGCTTTCGC TGTACGGCAG TAGTCGGTGC
                                                                6360

TCGTCCAGAC GGGCCAGGGT CATGTCTTTC CACGGGCGCA GGGTCCTCGT CAGCGTAGTC
                                                                6420

TGGGTCACGG TGAAGGGGTG CGCTCCGGGC TGCGCGCTGG CCAGGGTGCG CTTGAGGCTG
                                                                6480

GTCCTGCTGG TGCTGAAGCG CTGCCGGTCT TCGCCCTGCG CGTCGGCCAG GTAGCATTTG
                                                                6540

ACCATGGTGT CATAGTCCAG CCCCTCCGCG GCGTGGCCCT TGGCGCGCAG CTTGCCCTTG
                                                                6600

GAGGAGGCGC CGCACGAGGG GCAGTGCAGA CTTTTGAGGG CGTAGAGCTT GGGCGCGAGA
                                                                6660

AATACCGATT CCGGGGAGTA GGCATCCGCG CCGCAGGCCC CGCAGACGGT CTCGCATTCC
                                                                6720

ACGAGCCAGG TGAGCTCTGG CCGTTCGGGG TCAAAAACCA GGTTTCCCCC ATGCTTTTTG
                                                                6780

ATGCGTTTCT TACCTCTGGT TTCCATGAGC CGGTGTCCAC GCTCGGTGAC GAAAAGGCTG
                                                                6840
```

FIGURE 9G

```
TCCGTGTCCC CGTATACAGA CTTGAGAGGC CTGTCCTCGA CCGATGCCCT TGAGAGCCTT
                                                                6900

CAACCCAGTC AGCTCCTTCC GGTGGGCGCG GGGCATGACT ATCGTCGCCG CACTTATGAC
                                                                6960

TGTCTTCTTT ATCATGCAAC TCGTAGGACA GGTGCCGGCA GCGCTCTGGG TCATTTTCGG
                                                                7020

CGAGGACCGC TTTCGCTGGA GCGCGACGAT GATCGGCCTG TCGCTTGCGG TATTCGGAAT
                                                                7080

CTTGCACGCC CTCGCTCAAG CCTTCGTCAC TGGTCCCGCC ACCAAACGTT TCGGCGAGAA
                                                                7140

GCAGGCCATT ATCGCCGGCA TGGCGGCCGA CGCGCTGGGC TACGTCTTGC TGGCGTTCGC
                                                                7200

GACGCGAGGC TGGATGGCCT TCCCCATTAT GATTCTTCTC GCTTCCGGCG GCATCGGGAT
                                                                7260

GCCCGCGTTG CAGGCCATGC TGTCCAGGCA GGTAGATGAC GACCATCAGG GACAGCTTCA
                                                                7320

AGGATCGCTC GCGGCTCTTA CCAGCCTAAC TTCGATCACT GGACCGCTGA TCGTCACGGC
                                                                7380

GATTTATGCC GCCTCGGCGA GCACATGGAA CGGGTTGGCA TGGATTGTAG GCGCCGCCCT
                                                                7440

ATACCTTGTC TGCCTCCCCG CGTTGCGTCG CGGTGCATGG AGCCGGGCCA CCTCGACCTG
                                                                7500

AATGGAAGCC GGCGGCACCT CGCTAACGGA TTCACCACTC CAAGAATTGG AGCCAATCAA
                                                                7560

TTCTTGCGGA GAACTGTGAA TGCGCAAACC AACCCTTGGC AGAACATATC CATCGCGTCC
                                                                7620

GCCATCTCCA GCAGCCGCAC GCGGCGCATC TCGGGCAGCG TTGGGTCCTG GCCACGGGTG
                                                                7680

CGCATGATCG TGCTCCTGTC GTTGAGGACC CGGCTAGGCT GGCGGGGTTG CCTTACTGGT
                                                                7740

TAGCAGAATG AATCACCGAT ACGCGAGCGA ACGTGAAGCG ACTGCTGCTG CAAAACGTCT
                                                                7800

GCGACCTGAG CAACAACATG AATGGTCTTC GGTTTCCGTG TTTCGTAAAG TCTGGAAACG
                                                                7860

CGGAAGTCAG CGCCCTGCAC CATTATGTTC CGGATCTGCA TCGCAGGATG CTGCTGGCTA
                                                                7920

CCCTGTGGAA CACCTACATC TGTATTAACG AAGCCTTTCT CAATGCTCAC GCTGTAGGTA
                                                                7980
```

FIGURE 9H

```
TCTCAGTTCG GTGTAGGTCG TTCGCTCCAA GCTGGGCTGT GTGCACGAAC CCCCCGTTCA
                                                                8040

GCCCGACCGC TGCGCCTTAT CCGGTAACTA TCGTCTTGAG TCCAACCCGG TAAGACACGA
                                                                8100

CTTATCGCCA CTGGCAGCAG CCACTGGTAA CAGGATTAGC AGAGCGAGGT ATGTAGGCGG
                                                                8160

TGCTACAGAG TTCTTGAAGT GGTGGCCTAA CTACGGCTAC ACTAGAAGGA CAGTATTTGG
                                                                8220

TATCTGCGCT CTGCTGAAGC CAGTTACCTT CGGAAAAAGA GTTGGTAGCT CTTGATCCGG
                                                                8280

CAAACAAACC ACCGCTGGTA GCGGTGGTTT TTTTGTTTGC AAGCAGCAGA TTACGCGCAG
                                                                8340

AAAAAAAGGA TCTCAAGAAG ATCCTTTGAT CTTTTCTACG GGTCTGACG CTCAGTGGAA
                                                                8400

CGAAAACTCA CGTTAAGGGA TTTTGGTCAT GAGATTATCA AAAAGGATCT TCACCTAGAT
                                                                8460

CCTTTTAAAT TAAAAATGAA GTTTTAAATC AATCTAAAGT ATATATGAGT AAACTTGGTC
                                                                8520

TGACAGTTAC CAATGCTTAA TCAGTGAGGC ACCTATCTCA GCGATCTGTC TATTTCGTTC
                                                                8580

ATCCATAGTT GCCTGACTCC CCGTCGTGTA GATAACTACG ATACGGGAGG GCTTACCATC
                                                                8640

TGGCCCCAGT GCTGCAATGA TACCGCGAGA CCCACGCTCA CCGGCTCCAG ATTTATCAGC
                                                                8700

AATAAACCAG CCAGCCGGAA GGGCCGAGCG CAGAAGTGGT CCTGCAACTT TATCCGCCTC
                                                                8760

CATCCAGTCT ATTAATTGTT GCCGGGAAGC TAGAGTAAGT AGTTCGCCAG TTAATAGTTT
                                                                8820

GCGCAACGTT GTTGCCATTG CTGCAGGCAT CGTGGTGTCA CGCTCGTCGT TTGGTATGGC
                                                                8880

TTCATTCAGC TCCGGTTCCC AACGATCAAG GCGAGTTACA TGATCCCCCA TGTTGTGCAA
                                                                8940

AAAAGCGGTT AGCTCCTTCG GTCCTCCGAT CGTTGTCAGA AGTAAGTTGG CCGCAGTGTT
                                                                9000

ATCACTCATG GTTATGGCAG CACTGCATAA TTCTCTTACT GTCATGCCAT CCGTAAGATG
                                                                9060

CTTTTCTGTG ACTGGTGAGT ACTCAACCAA GTCATTCTGA GAATAGTGTA TGCGGCGACC
                                                                9120
```

FIGURE 9I

```
GAGTTGCTCT TGCCCGGCGT CAACACGGGA TAATACCGCG CCACATAGCA GAACTTTAAA
                                                                9180
AGTGCTCATC ATTGGAAAAC GTTCTTCGGG GCGAAAACTC TCAAGGATCT TACCGCTGTT
                                                                9240
GAGATCCAGT TCGATGTAAC CCACTCGTGC ACCCAACTGA TCTTCAGCAT CTTTTACTTT
                                                                9300
CACCAGCGTT TCTGGGTGAG CAAAAACAGG AAGGCAAAAT GCCGCAAAAA AGGGAATAAG
                                                                9360
GGCGACACGG AAATGTTGAA TACTCATACT CTTCCTTTTT CAATATTATT GAAGCATTTA
                                                                9420
TCAGGGTTAT TGTCTCATGA GCGGATACAT ATTTGAATGT ATTTAGAAAA ATAAACAAAT
                                                                9480
AGGGGTTCCG CGCACATTTC CCCGAAAAGT GCCACCTGAC GTCTAAGAAA CCATTATTAT
                                                                9540
CATGACATTA ACCTATAAAA ATAGGCGTAT CACGAGGCCC TTTCGTCTTC AA
                                                         9592
```

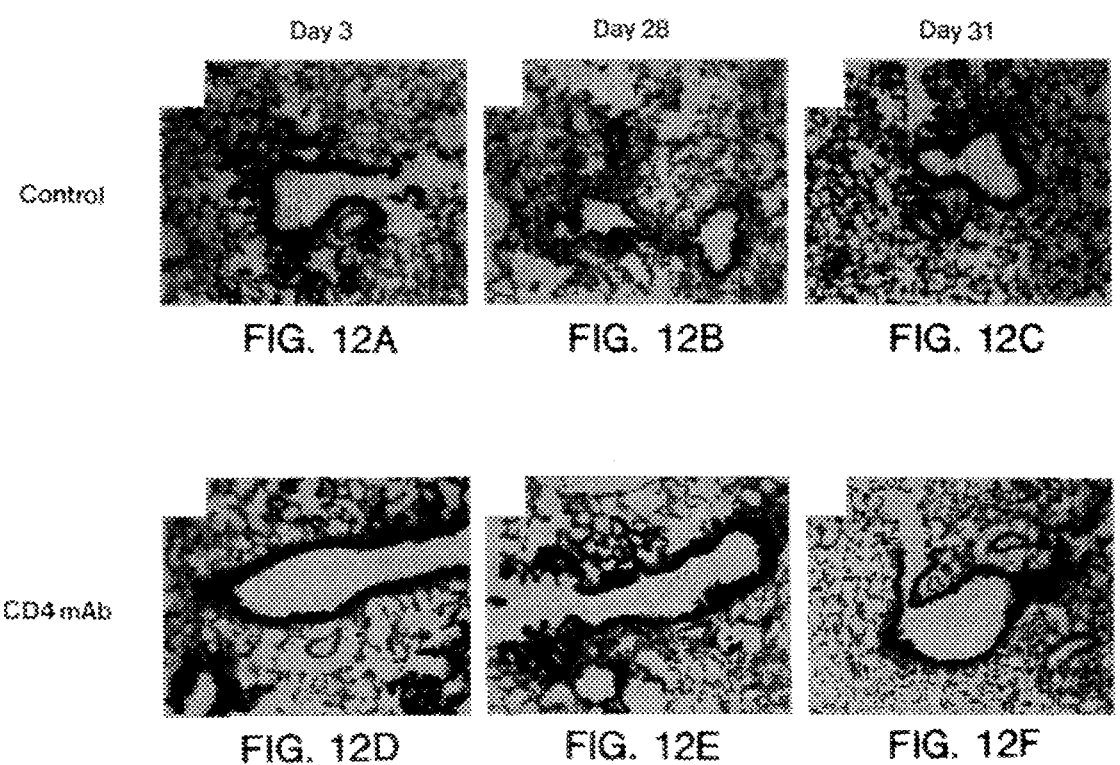

IL-12
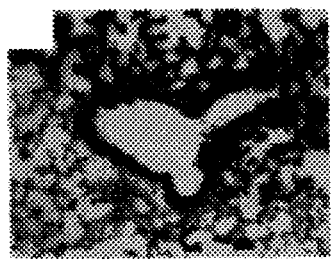 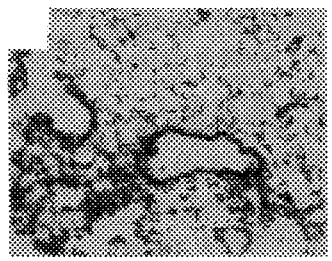 
FIG. 12G  FIG. 12H  FIG. 12I
IFN-γ
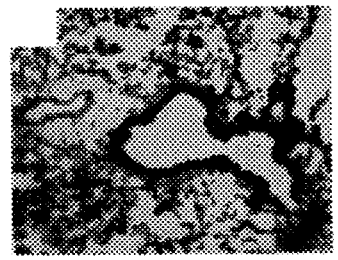 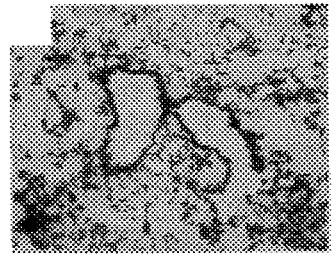 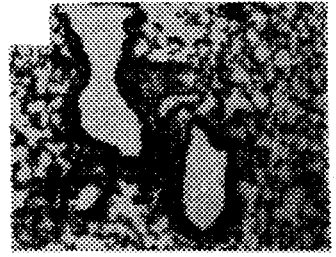
FIG. 12J  FIG. 12K  FIG. 12L
Day 3  Day 28  Day 31

METHODS AND COMPOSITIONS FOR GENE THERAPY FOR THE TREATMENT OF DEFECTS IN LIPOPROTEIN METABOLISM

This invention was supported by the National Institute of Health Grant Nos. DK 42193-05 and HD 29946. The United States government has rights in this invention.

FIELD OF THE INVENTION

The present invention relates to the field of somatic gene therapy and the treatment of genetic disorders related to lipoprotein metabolism.

BACKGROUND OF THE INVENTION

The metabolism of lipids, particularly cholesterol, involves the interaction of a number of lipoproteins and apolipoproteins. Very low density lipoprotein (VLDL) and apolipoprotein E (apoE) are key precursor molecules in the production of low density lipoprotein (LDL) and in the overall metabolism of lipids, including cholesterol. LDL is the major cholesterol-transport lipoprotein in human plasma.

The VLDL/apoE receptors are expressed in heart, skeletal muscle, and adipose tissue [F. M. Wittmaack et al, *Endocrinol.*, 136(1):340–348 (1995)] with lower levels of expression in the kidney, placenta, pancreas, and brain. This receptor has been suggested to play a role in the uptake of triglyceride-rich lipoprotein particles by specific organs. The cDNA encoding the putative human VLDL receptor was recently cloned [M. E. Gafvels et al, *Som. Cell Mol. Genet.*, 19:557–569 (1993), incorporated by reference herein]. The receptor for LDL is located in coated pits on the surfaces of cells in the liver and other organs.

As depicted in FIG. 1A, in a normal healthy human, the molecules apolipoprotein B48 (Apo-B48), apolipoprotein C-II (Apo-C-II) and Apo E form a chylomicron particle in plasma passing through the intestines, which interacts with a chylomicron remnant receptor in the liver. After metabolism of the chylomicrons taken up by the remnant receptor, the liver produces the primary lipoprotein, VLDL, which contains Apo-E, Apo-C-II and apolipoprotein B100 (Apo B100). VLDL is metabolized into LDL, which binds to the LDL receptor in the liver via Apo B100. The LDL receptor in the liver facilitates the uptake of LDL by receptor-mediated endocytosis. LDL is degraded in lysosomes, and its cholesterol is released for metabolic use.

Defects in the metabolism of such lipoproteins and/or receptors result in several serious metabolic disorders. The human disease familial hyper-cholesterolemia (FH) is caused primarily by one or more mutations in the gene encoding the LDL receptor. FH is characterized clinically by (1) an elevated concentration of LDL; (2) deposition of LDL-derived cholesterol in tendons and skin (xanthomas) and in arteries (atheromas); and (3) inheritance as an autosomal dominant trait with a gene dosage effect. Individuals with FH develop premature coronary heart disease, usually in childhood. Heterozygotes number about 1 in 500 persons, placing FH among the most common inborn errors of metabolism. Heterozygotes have twofold elevations in plasma cholesterol (350 to 550 mg/dl) from birth and tend to develop tendon xanthomas and coronary atherosclerosis after age 20. Homozygotes number 1 in 1 million persons and are characterized by severe hypercholesterolemia (650 to 1000 mg/dl), cutaneous xanthomas which appear within the first 4 years of life, and coronary heart disease which begins in childhood and frequently causes death before age 20. [J. Goldstein et al, "Familial Hypercholesterolemia", Chapter 48, in *The Metabolic Basis of Inherited Disease*, 6th ed., C. R. Scrivers et al (eds), McGraw-Hill Information Services Co., NY, N.Y., (1989) pp. 1215–1250].

Another metabolic disorder is familial combined hyperlipidemia (FCH) which was first associated with hyperlipidemia in survivors of myocardial infarction and their relatives. FCH patients generally have one of three phenotypes: (1) elevated levels of VLDL, (2) elevated levels of LDL, or (3) increases in the levels of both lipoproteins in plasma. Unlike FH, FCH appears in only 10 to 20 percent of patients in childhood, usually in the form of hypertriglyceridemia. Homozygosity for the trait may result in severe hypertriglyceridemia. [J. Goldstein et al, "Disorders of the Biogenesis and Secretion of Lipoproteins", Chapter 44B in *The Metabolic Basis of Inherited Disease*, 6th ed., C. R. Scrivers et al (eds), McGraw-Hill Information Services Co., NY, N.Y., (1989) pp. 1155–1156]. This disorder is also associated with the appearance of glucose intolerance and obesity in a number of individuals.

The most striking abnormality of FCH is marked elevation of VLDL content of plasma. Increased production of VLDL leads to an expanded plasma pool of VLDL in some individuals, but in others with more efficient lipolysis, it results in increased levels of LDL. FCH is characterized by an excess production of LDL, rather than a genetic defect in the LDL receptor. The LDL receptors of cultured fibroblasts appear to be normal in FCH patients.

Clinical experience suggests that FCH is at least five times as prevalent as FH, occurring in about 1 percent of the North American population. The predilection toward coronary artery disease among patients with this disorder makes it the most prominent known metabolic cause of premature atherosclerosis [J. Goldstein et al, cited above].

When LDL receptors are deficient as in FH (see FIG. 1B), or excess LDL is produced due to excess VLDL as in FCH, the efficient removal of LDL from plasma by the liver declines, and the level of LDL rises in inverse proportion to the receptor number. The excess plasma LDL is deposited in connective tissues and in scavenger cells, resulting in the symptoms of either disorder.

Presently, treatment for FH and FCH is directed at lowering the plasma level of LDL by the administration of drugs, i.e., combined administration of a bile acid-binding resin and an inhibitor of 3-hydroxy-3-methylglutaryl CoA reductase for treatment of FH and niacin for treatment of FCH. However, FH homozygotes with two nonfunctional genes are resistant to drugs that work by stimulating LDL receptors. Similarly, such drugs are not particularly effective in FCH. In FH homozygotes, plasma LDL levels can be lowered only by physical or surgical means.

Administration of normal LDL receptor genes by an adenovirus vector has been contemplated for the treatment of FH. Adenovirus vectors are capable of providing extremely high levels of transgene delivery to virtually all cell types, regardless of the mitotic state. The efficacy of this system in delivering a therapeutic transgene in vivo that complements a genetic imbalance has been demonstrated in animal models of various disorders [K. F. Kozarsky et al, *Somatic Cell Mol. Genet.*, 19:449–458 (1993) ("Kozarsky et al I"); K. F. Kozarsky et al, *J. Biol. Chem.*, 269:13695–13702 (1994) ("Kozarsky et al II); Y. Watanabe, *Atherosclerosis*, 36:261–268 (1986); K. Tanzawa et al, *FEBS Letters*, 118(1):81–84 (1980); J. L. Golasten et al, *New Engl. J. Med.*, 309(11983):288–296 (1983); S. Ishibashi et al, *J. Clin. Invest.*, 92:883–893 (1993); and S. Ishibashi et al, *J. Clin. Invest.*, 93:1885–1893 (1994)]. The use of adenovirus vectors in the transduction of genes into hepatocytes in vivo has previously been demonstrated in rodents and rabbits [see, e.g., Kozarsky II, cited above, and S. Ishibashi et al, *J. Clin. Invest.*, 92:883–893 (1993)].

Recent research has shown that introduction of a recombinant adenovirus encoding the human LDL receptor ("LDLR") cDNA into the livers of LDL receptor-deficient Watanabe heritable hyperlipidemic (WHHL) rabbits, which mimic the condition of FH, via an adenovirus vector resulted in large, transient reductions in plasma cholesterol. The transient nature of the effect of recombinant adenoviruses in most situations is the development of cellular immune responses to the virus-infected cells and their elimination. Antigenic targets for immune mediated clearance are viral proteins expressed from the recombinant viral genome and/ or the product of the transgene, which in this case, is the LDL receptor protein [Y. Yang et al, *Proc. Natl. Acad. Sci., USA*, 91:4407–4411 (May 1994); Y. Yang et al, *Immun.*, 1:433–442 (August 1994)].

Additionally, repeated reinfusions of the LDLR gene-containing adenovirus did not produce similar, subsequent cholesterol reductions due to the development of neutralizing anti-adenovirus antibodies [Kozarsky et al I and Kozarsky et al II, cited above; see also Y. Yang et al, *Immun.*, 1:433–442 (August 1994), all incorporated by reference herein].

There remains a need in the art for therapeutic compositions and gene therapy strategies which enable effective treatment and/or prevention of FH and FCH, as well as other defects in lipoprotein metabolism.

SUMMARY OF THE INVENTION

In one aspect, the invention provides a recombinant viral vector comprising the DNA of, or corresponding to, at least a portion of the genome of an adenovirus, which portion is capable of infecting a hepatic cell; and a human VLDL receptor ("VLDLR") gene operatively linked to regulatory sequences directing its expression, the vector capable of expressing the VLDLR gene product in the hepatic cell in vivo or in vitro.

In another aspect, the invention provides a mammalian cell infected with the viral vector described above.

In still a further aspect, the invention provides a method for delivering and stably integrating a VLDLR gene into the chromosome of a mammalian hepatocyte cell comprising introducing into said cell an effective amount of a recombinant viral vector described above.

Another aspect of this invention is a method for treating a patient having a metabolic disorder comprising administering to the patient by an appropriate route an effective amount of an above described vector containing a normal VLDLR gene, wherein said VLDLR gene is integrated into the chromosome of said patient's hepatocytes and said receptor is expressed stably in vivo at a location in the body where it is not normally expressed.

Other aspects and advantages of the present invention are described further in the following detailed description of the preferred embodiments thereof.

BRIEF DESCRIPTION OF THE DRAWINGS

FIG. 8 is the DNA sequence [SEQ ID NO: 1] with encoded amino acid sequence [SEQ ID NO: 2] of the human VLDL receptor gene, as reported by Gafvels et al, cited above.

FIG. 9 is the DNA sequence of pAd.CMVVLDLR [SEQ ID NO: 3], in which Ad 0–1 spans nucleotides 12–364, CMV ehn/prom spans nucleotides 381–862; nucleotides 966–4107 encode VLDLR, pA spans nucleotides 4192–4390; Ad 9.2–16.1 span nucleotides 4417–6880 and nucleotides 6881–9592 are pAT153 sequences.

FIG. 12A is an X-gal histochemical stain of lymph nodes of C57Bl/6 mice adenovirus-infected on day 0 as described in Example 8 (magnification x100) depicting the staining of lymph nodes from normal mice ("control") necrotized on day 3.

FIG. 12B is a stain from control mice immunized as in FIG. 12A, and necrotized on day 28.

FIG. 12C is a stain from control mice, immunized as in FIG. 12A, and necrotized on day 31 following reinfection with lacZ-containing adenovirus vector on day 28.

FIG. 12D is a stain on day 3 of lymph nodes from mice immunized as in FIG. 12A, and depleted on days −3, 0, and +3 of CD4$^+$ cells with mAb ("CD4 mAb").

FIG. 12E is a stain on day 28 of CD4 mAb mice immunized as in FIG. 12A.

FIG. 12F is a stain on day 31 of CD4 mAb mice immunized as in FIG. 12A.

FIG. 12G is a stain of lymph nodes from mice immunized as in FIG. 12A, and treated with IL-12 on days 0 and +1 ("IL-12") and necrotized on day 3.

FIG. 12H is a stain on day 28 of IL-12 mice immunized as in FIG. 12A.

FIG. 12I is a stain on day 31 of IL-12 mice immunized as in FIG. 12A.

FIG. 12J is a stain of lymph nodes from mice immunized as in FIG. 12A and treated with IFN-γ on days 0 and +1 ("IFN-γ") and necrotized on day 3.

FIG. 12K is a stain on day 28 of IFN-γ mice immunized as in FIG. 12A.

FIG. 12L is a stain on day 31 of IFN-γ mice, immunized as in FIG. 12A.

DETAILED DESCRIPTION OF THE INVENTION

The present invention provides novel compositions and methods which enable the therapeutic treatment of metabolic disorders, such as FH and FCH, characterized by the accumulation of LDL in human plasma. This invention provides for the use of a viral vector to introduce and stably express a gene normally expressed in mammals, i.e., the gene encoding a normal receptor for very low density lipoprotein (VLDLR), in a location in the body where that gene is not naturally present, i.e., in the liver.

The method and compositions of the present invention overcome the problems previously identified in the gene therapy treatment of LDL receptor-deficient individuals. As described in detail below, by use of a viral vector capable of targeting cells of the liver, the VLDL receptor gene is introduced into, and stably expressed in, the cells of the liver. The present invention differs from direct gene replacement in that the VLDL receptor protein is expressed normally in LDL receptor deficient individuals, e.g., the macrophages. The gene therapy using this type of vector would result not in expression of a new gene product but in de novo expression in an organ which otherwise does not express the gene product. The patient does not mount an immune (specifically, a CTL-mediated) response against the VLDLR gene expressed in the liver (i.e., the vector-delivered VLDLR gene is not recognized as a foreign antigen). There is no induction of CTL-mediated elimination of the transfected cell. The opposite result occurs when an LDLR gene is administered to an LDLR-deficient individual with FH [see, e.g., Kozarsky I and II, cited above].

Due to this recognition of the VLDLR gene by the patient's immune system as a known gene, and to the tendency of hepatocytes to have a long life in circulation, the hepatocytes transfected with the vector of this invention, which express the VLDLR gene, tend to be stable and VLDLR expression is not transient. That is, insertion of the non-foreign VLDLR gene in hepatocytes permits the receptor gene to be expressed for the duration of the hepatocyte's life. This increases the duration of treatment of the lipoprotein metabolic disorder without the need for reinfusion of the vector, thus initially limiting possible formation of neutralizing anti-vector antibodies.

The vectors and methods of this invention can provide gene therapy useful to treat and/or supplement current treatments for lipoprotein metabolic disorders. The presence of the VLDL receptor gene in the transfected hepatocytes according to this invention permits the binding of VLDL, a precursor of LDL, from the plasma at the site of the liver, thereby decreasing the amount of VLDL in plasma. The decrease in VLDL in the plasma at this site consequently decreases the production of plasma LDL.

Figure 1A:
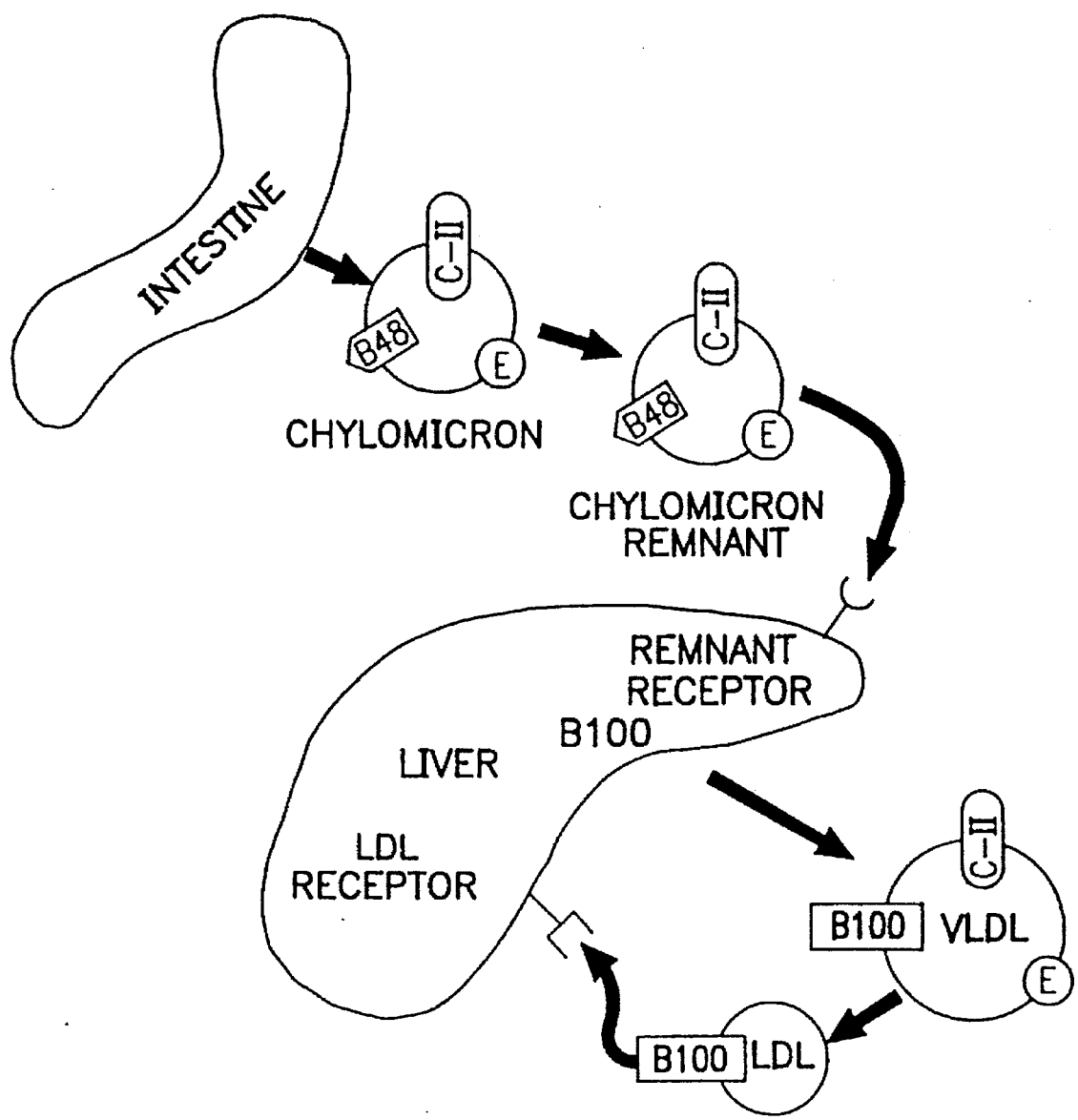
FIG. 1A is a schematic drawing of normal human and rabbit lipoprotein metabolism. The apolipoproteins are referred to as B48, B100, C-II, and E. LDL and VLDL are identified.
Figure 1B:
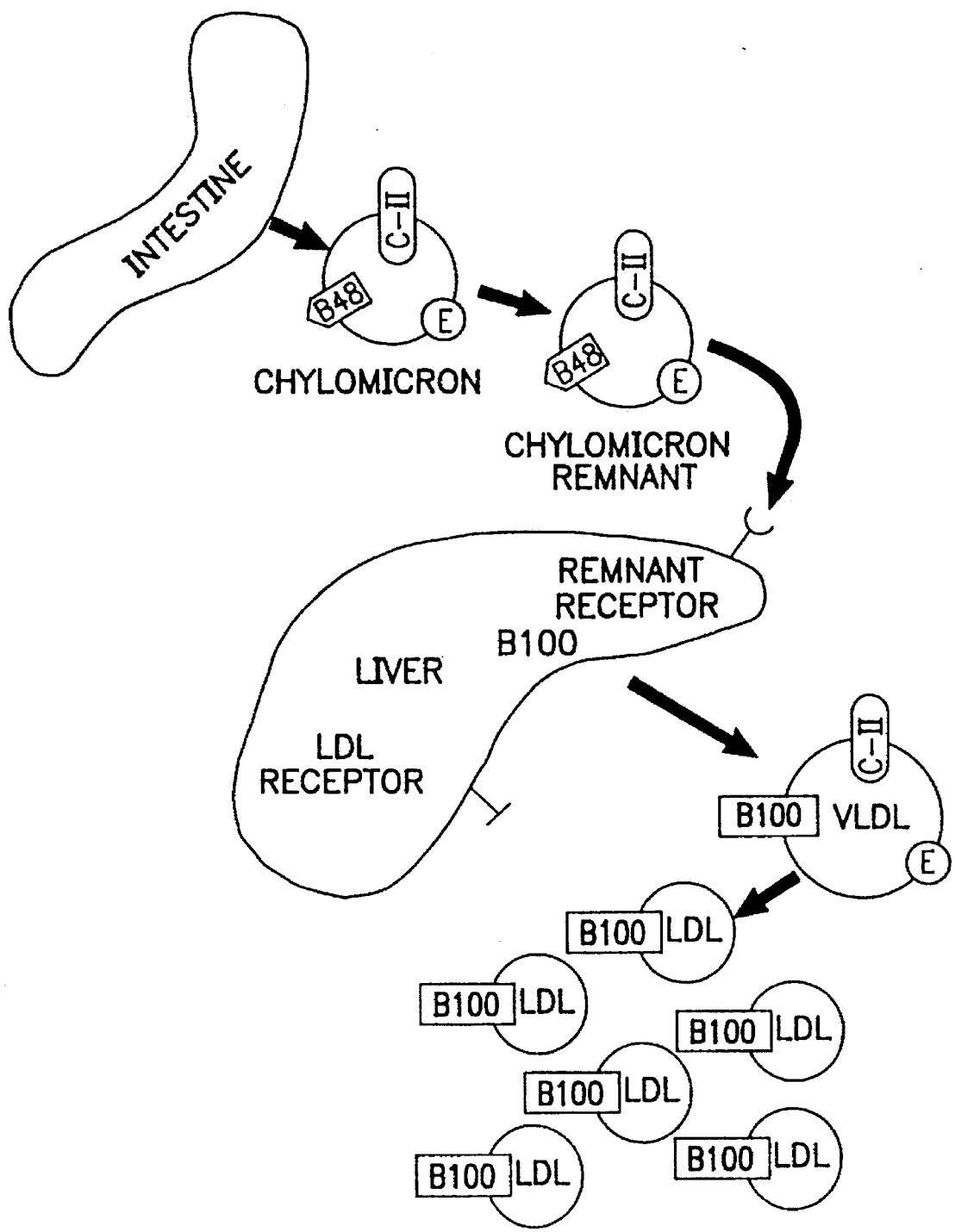
FIG. 1B is a schematic drawing of lipoprotein metabolism in FH patients and WHHL rabbits. The abbreviations are as described in FIG. 1A.
Figure 1C:
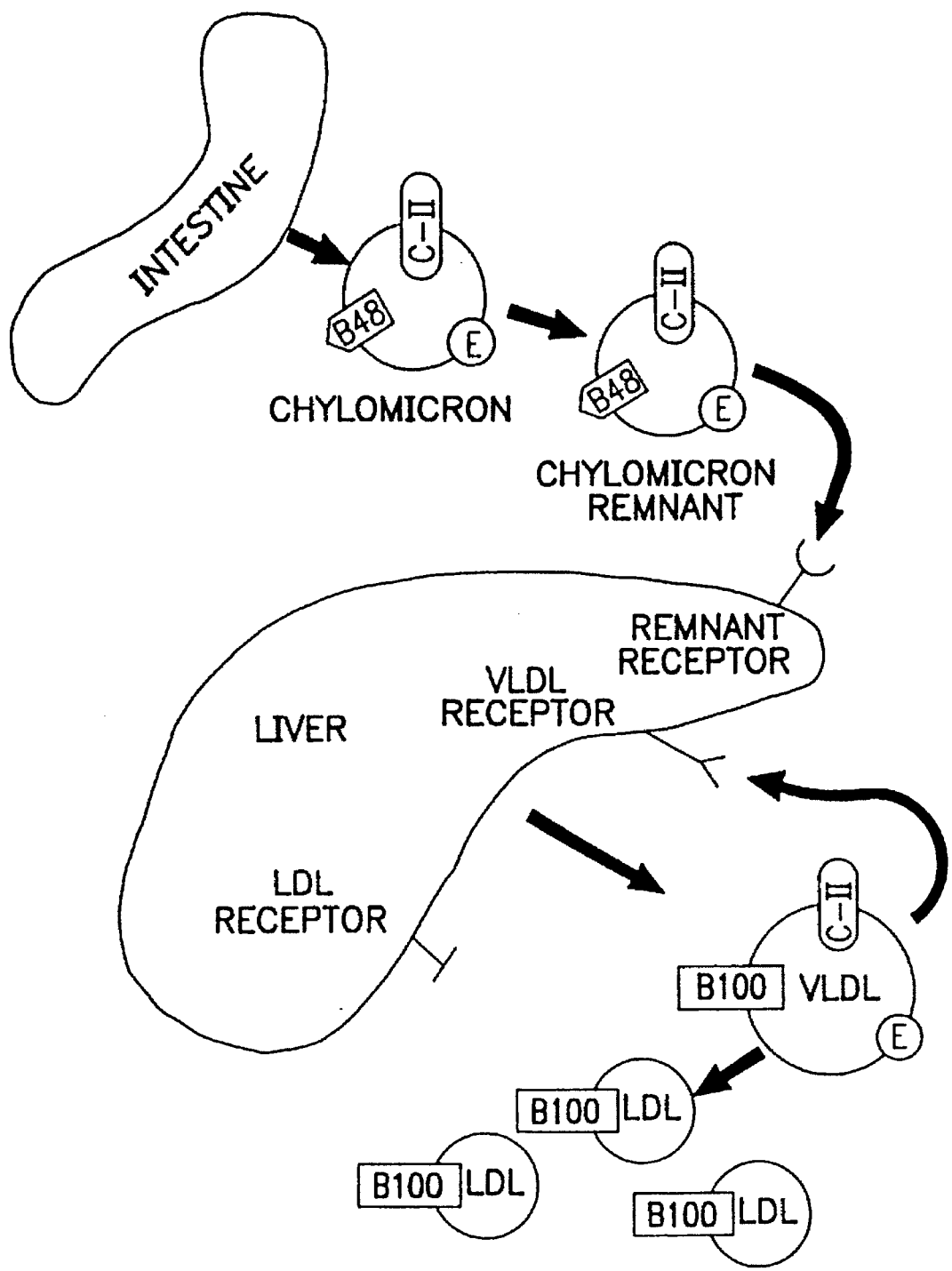
FIG. 1C is a schematic drawing of lipoprotein metabolism in rabbits infused with the recombinant VLDLR gene according to the invention.

For example, in FH, this reduction in plasma LDL can compensate for the defective LDL receptors in the liver. In FCH, this reduced production of plasma LDL from VLDL prevents the normal LDL receptors in the liver from becoming overloaded by excess LDL, and reduces the excess VLDL which contributes to the disorder. Compare, for example, the schematic representations of the normal operation of lipid metabolism (FIG. 1A) to the abnormal metabolism caused by FH (FIG. 1B) and then to the method of this invention (FIG. 1C).

I. Recombinant Viral Particles as Gene Therapy Vectors

The compositions of this invention involve the construction of desirable gene therapy vectors, which are capable of delivering and stably integrating a functional, normal VLDL receptor gene, to hepatocytes. Such gene therapy vectors include a selected virus vector, desirably deleted in one or more viral genes, a minigene containing the VLDLR gene under the control of regulatory sequences, and optional helper viruses and/or packaging cell lines which supply to the viral vectors any necessary products of deleted viral genes.

The viral sequences used in the vectors, helper viruses, if needed, and recombinant viral particles, and other vector components and sequences employed in the construction of the vectors described herein are obtained from commercial or academic sources based on previously published and described sequences. These viral materials may also be obtained from an individual patient. The viral sequences and vector components may be generated by resort to the teachings and references contained herein, coupled with standard recombinant molecular cloning techniques known and practiced by those skilled in the art. Modifications of existing nucleic acid sequences forming the vectors, including sequence deletions, insertions, and other mutations taught by this specification may be generated using standard techniques.

The methods employed for the selection of viral sequences useful in a vector, the cloning and construction of VLDLR "minigene" and its insertion into a desired viral vector and the production of a recombinant infectious viral particle by use of helper viruses and the like are within the skill in the art given the teachings provided herein.

A. Construction of the "Minigene"

By "minigene" is meant the combination of the VLDLR gene and the other regulatory elements necessary to transcribe the gene and express the gene product in vivo. The human VLDL receptor sequence has been provided [see, Gafvels et al, cited above; SEQ ID NOS: 1 and 2]. Generally, the entire coding region of this receptor sequence is used in the minigene; the 5' and 3' sequences of SEQ ID NO: 1 are not essential to the minigene. VLDL receptor genes of other mammalian origin, e.g., rabbit, monkey, etc., may also be useful in this invention.

The VLDL receptor gene (VLDLR) is operatively linked to regulatory components in a manner which permits its transcription. Such components include conventional regulatory elements necessary to drive expression of the VLDLR transgene in a cell transfected with the viral vector. Thus the minigene also contains a selected promoter which is linked to the transgene and located, with other regulatory elements, within the selected viral sequences of the recombinant vector.

Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, *Cell*, 41:521–530 (1985)]. Another desirable promoter includes the Rous sarcoma virus LTR promoter/enhancer. Still another promoter/enhancer sequence is the chicken cytoplasmic β-actin promoter [T. A. Kost et al, *Nucl. Acids Res.*, 11(23):8287 (1983)]. Other suitable promoters may be selected by one of skill in the art.

The minigene may also desirably contain nucleic acid sequences heterologous to the viral vector sequences including sequences providing signals required for efficient polyadenylation of the transcript (poly-A or pA) and introns with functional splice donor and acceptor sites. A common poly-A sequence which is employed in the exemplary vectors of this invention is that derived from the papovavirus SV-40. The poly-A sequence generally is inserted in the minigene following the transgene sequences and before the viral vector sequences. A common intron sequence is also derived from SV-40, and is referred to as the SV-40 T intron sequence. A minigene of the present invention may also contain such an intron, desirably located between the promoter/enhancer sequence and the transgene. Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

As above stated, the minigene is located in the site of any selected deletion in the viral vector. See Example 1 below.

B. Construction of The Viral Plasmid Vector

Although a number of viral vectors have been suggested for gene therapy, the most desirable vector for this purpose is a recombinant adenoviral vector or adeno-associated vector. Adenovirus vectors as described below are preferred because they can be purified in large quantities and highly concentrated, and the virus can transduce genes into non-dividing cells. However, it is within the skill of the art for other adenovirus, or even retrovirus, vaccinia or other virus vectors to be similarly constructed.

Adenoviruses are eukaryotic DNA viruses that can be modified to efficiently deliver a therapeutic or reporter transgene to a variety of cell types. Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, Virology, 2d edit., ed. B. N. Fields, Raven Press, Ltd., New York (1990)]. The general adenoviruses types 2 and 5 (Ad2 and Ad5, respectively), are not associated with human malignancies.

Suitable adenovirus vectors useful in gene therapy are well known [see, e.g., M. S. Horwitz et al, "Adenoviridae and Their Replication" Virology, second edition, pp. 1712, ed. B. N. Fields et al, Raven Press Ltd., New York (1990); M. Rosenfeld et al, Cell, 68:143–155 (1992); J. F. Engelhardt et al, Human Genet. Ther., 4:759–769 (1993); Y. Yang et al, Nature Genet. 7:362–269 (1994); J. Wilson, Nature, 365:691–692 (Oct. 1993); B. J. Carter, in "Handbook of Parvoviruses", ed. P. Tijsser, CRC Press, pp. 155–168 (1990).

Adenovirus vectors useful in this invention may include the DNA sequences of a number of adenovirus types. The adenovirus sequences useful in the vectors described herein may be obtained from any known adenovirus type, including the presently identified 41 human types [see, e.g., Horwitz, cited above]. The sequence of a strain of adenovirus type 5 may be readily obtained from Genbank Accession No. M73260. Similarly, adenoviruses known to infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources.

Adenovirus vectors useful in this invention include recombinant, defective adenoviruses optionally bearing other mutations, e.g., temperature sensitive mutations, deletions and hybrid vectors formed by adenovirus/adeno-associated virus sequences. Suitable vectors are described in the published literature [see, for example, Kozarsky I and II, cited above, and references cited therein, U.S. Pat. No. 5,240,846 and the copending applications incorporated herein by reference below.

In the construction of useful adenovirus vectors for delivery of the VLDLR gene to the liver, adenovirus nucleic acid sequences employed in the vectors can range from a minimum sequence amount, which vector requires the use of a helper virus to produce a hybrid virus particle, to only selected deletions of adenovirus genes, which deleted gene products can be supplied in the viral vector production process by a selected packaging cell line.

1. Recombinant Minimal Adenovirus

Desirable adenovirus (Ad) vectors useful in the present invention are described in detail in co-pending, co-owned U.S. patent application Ser. No. 08/331,381, which is incorporated by reference herein for the purpose of describing these vectors.

Briefly summarized, the minimal Ad virus is a viral particle containing only the adenovirus cis-elements necessary for replication and virion encapsidation, but otherwise deleted of all adenovirus genes. That is, the vector contains only the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. This left terminal (5') sequence of the Ad5 genome spans bp 1 to about 360 of the conventional published Ad5 adenovirus genome, also referred to as map units 0–1 of the viral genome, and generally is from about 353 to about 360 nucleotides in length. This sequence includes the 5'ITR (bp 1 to about 103 of the adenovirus genome); and the packaging/enhancer domain (bp about 194 to about 358 of the adenovirus genome). The minimal 3' adenovirus sequences of the adenovirus vector may include the right terminal (3') ITR sequence of the adenoviral genome spanning about bp 35,353—end of the adenovirus genome, or map units ~98.4–100. This sequence is generally about 580 nucleotide in length. Between such sequences a VLDLR minigene, as described above, is inserted.

Production of an infectious particle from the this minimal Ad viral vector involves the assistance of a helper virus, as discussed below. A second type of minimal vector also disclosed in the above-incorporated reference places the 5' Ad terminal sequence in a head-to-tail arrangement relative to the 3' terminal sequence. The minimal Ad vector co-infected with a helper virus and/or a packaging cell line, provides all of the viral gene products necessary to produce an infective recombinant viral particle containing the VLDLR minigene. Alternatively, this vector can contain additional adenovirus gene sequences, which then are not required to be supplied by a helper gene.

2. Other Defective Adenoviruses

Recombinant, replication-deficient adenoviruses useful for gene therapy of this invention may be characterized by containing more than the minimal adenovirus sequences defined above. These other Ad vectors can be characterized by deletions of various portions of gene regions of the virus, and infectious virus particles formed by the optional use of helper viruses and/or packaging cell lines. Suitable defective adenoviruses are described in more detail in Kozarsky and Wilson, Curr. Opin. Genet. Devel., 3:499–503 (1993); Kozarsky I and II, cited above, and references cited therein, all incorporated herein by reference.

As one example, suitable vectors may be formed by deleting all or a sufficient portion of the adenoviral early immediate early gene E1a (which spans mu 1.3 to 4.5) and delayed early gene E1b (which spans mu 4.6 to 11.2) so as to eliminate their normal biological functions. These replication-defective E1-deleted viruses are capable of replicating and producing infectious virus when grown on an adenovirus-transformed, complementation human embryonic kidney cell line containing functional adenovirus E1a and E1b genes which provide the corresponding gene products in trans, the 293 cell [ATCC CRL1573]. The resulting virus is capable of infecting many cell types and can express a transgene (i.e., VLDLR gene), but cannot replicate in most cells that do not carry the E1 region DNA unless the cell is infected at a very high multiplicity of infection. Extensive experience in animals indicates this vector is not particularly desirable for gene therapy because low levels of viral proteins are expressed which elicit destructive cellular immune responses.

As another example, all or a portion of the adenovirus delayed early gene E3 (which spans mu 76.6 to 86.2) may be eliminated from the adenovirus sequence which forms a part of the hybrid construct. The function of E3 is irrelevant to the function and production of the recombinant virus particle. For example, Ad vectors may be constructed with a therapeutic minigene inserted into the E1-deleted region of the known mutant Ad5 sub360 backbone [J. Logan et al, Proc. Natl. Acad. Sci. USA, 81:3655–3659 (1984)]; or the Ad5 mutant dl7001 backbone [Dr. William Wold, Washington University, St. Louis]. Both mutant viruses also contain a deletion in the E3 region of the adenoviral genome; in sub360, at 78.5 to 84.3 mu, and in dl7001, at 78.4 to 86 mu. The life cycle of both sub360 and dl7001 display wild type characteristics.

Adenovirus vectors may also be constructed having a deletion of the E1 gene, at least a portion of the E3 region, and an additional deletion within adenovirus genes other than E1 and E3 to accommodate the VLDLR minigene and/or other mutations which result in reduced expression of adenoviral protein and/or reduced viral replication. For example, all or a portion of the adenovirus delayed early gene E2a (which spans mu 67.9 to 61.5) may be eliminated from the adenovirus vector. It is also anticipated that portions of the other delayed early genes E2b (which spans mu 29 to 14.2) and E4 (which spans mu 96.8 to 91.3) may also be eliminated from the adenovirus vector.

Deletions may also be made in any of the late genes L1 through L5, which span mu 16.45 to 99 of the adenovirus genome. Similarly, deletions may be useful in the intermediate genes IX (which maps between mu 9.8 and 11.2) and IVa$_2$ (which maps between 16.1 to 11.1). Other deletions may occur in the other structural or non-structural adenovirus genes.

The above discussed deletions may occur individually, i.e., an adenovirus sequence for use in the present invention may contain deletions of E1 only. Alternatively, deletions of entire genes or portions effective to destroy their biological activity may occur in any combination. For example, in one exemplary vector, the adenovirus sequence may contain deletions of the E1 genes and the E3 gene, or of the E1, E2a and E3 genes, or of the E1 and E4 genes, or of E1, E2a and E4 genes, with or without deletion of E3, and so on.

Vectors may also contain additional mutations in genes necessary for viral replication. Adenovirus vectors may contain a mutation which produces temperature-sensitive (ts) virus. Among such mutations include the incorporation of the missense temperature-sensitive mutation in the (DBP) E2a region found in the Ad5 H5ts125 strain [P. Vander Vliet et al, *J. Virol.*, 15:348–354 (1975)] at 62.5 mu. A single amino acid substitution (62.5 mu) at the carboxy end of the 72 kd protein produced from the E2a gene in this strain produces a protein product which is a single-stranded DNA binding protein and is involved in the replication of adenoviral genomic DNA. At permissive temperatures (approximately 32° C.) the ts strain is capable of full life cycle growth on HeLa cells, while at non-permissive temperatures (approximately 38° C.) no replication of adenoviral DNA is seen. In addition, at non-permissive temperatures, decreased immunoreactive 72 kd protein is seen in HeLa cells.

Exemplary vectors for use in this invention, for example, may be obtained by combining fragments from three independent DNA constructs including sub360 or d17001, H5ts125, and a cDNA plasmid with E1a sequences placed 5' to a therapeutic minigene. This type of vector is described by, for example, J. F. Engelhardt et al, *Proc. Natl. Acad. Sci. USA*, 91:6196–6200 (June 1994); Y. Yang et al, *Nature Genet.*, 7:362–369 (July, 1994) and references cited therein, all references incorporated herein by reference. Due to the mutations in the vector, there is reduced viral replication, reduction in expressed protein and an increase in the persistence of transgene expression. Other adenovirus vectors contain the H5ts125 mutation in addition to E3 deletions of sub360 and d17001. The minigene containing VLDLR as the transgene may be inserted into any deleted region of the selected Ad virus.

An exemplary Ad virus vector used to demonstrate this invention is the defective adenovirus vector H5.010CMVVLDLR, which contains adenovirus sequences Ad m.u. 0–1, followed by a VLDLR minigene, and the sequence Ad m.u.9 to 100 with small deletions in E3. See FIG. 3, described above. The recombinant adenovirus was fully deleted of E1a, E1b and partially deleted of E3. This recombinant virus vector is described in detail in Example 1.

3. Ad/AAV Hybrid Vectors

Another preferred vector is a hybrid Ad/AAV vector, which is the subject of co-owned, co-pending U.S. patent application Ser. No. 08/331,384, which is incorporated by reference herein.

At a minimum, the adenovirus nucleic acid sequences employed in the hybrid vector of this invention are the minimal adenovirus genomic sequences required for packaging adenoviral genomic DNA into a preformed capsid head, as described above. The entire adenovirus 5' sequence containing the 5'ITR and packaging/enhancer region can be employed as the 5' adenovirus sequence in the hybrid vector. The 3' adenovirus sequences of the vector include the right terminal (3') ITR sequence of the adenoviral genome discussed above. Some modifications to these sequences which do not adversely effect their biological function may be acceptable.

Also part of the hybrid vectors of this invention are sequences of an adeno-associated virus. The AAV sequences useful in the hybrid vector are the viral sequences from which the rep and cap polypeptide encoding sequences are deleted. More specifically, the AAV sequences employed are the cis- acting 5' and 3' inverted terminal repeat (ITR) sequences [See, e.g., B. J. Carter, cited above]. The AAV ITR sequences are about 143 bp in length. Substantially the entire sequences encoding the ITRs are used in the vectors, although some degree of minor modification of these sequences is expected to be permissible for this use. The ability to modify these ITR sequences is within the skill of the art. See, e.g., Sambrook et al, cited above.

In the hybrid vector construct, the AAV sequences are flanked by the adenovirus sequences discussed above. The 5' and 3' AAV ITR sequences themselves flank a VLDLR minigene sequence as described above. Thus, the sequence formed by the VLDLR minigene and flanking 5' and 3' AAV sequences may be inserted at any deletion site in the adenovirus sequences of the vector. For example, the AAV sequences are desirably inserted at the site of deleted E1a/E1b genes of the adenovirus, i.e., after map unit 1. Alternatively, the AAV sequences may be inserted at an E3 deletion, E2a deletion, and so on. If only the adenovirus 5' ITR/packaging sequences and 3' ITR sequences are used in the vector, the AAV sequences are inserted between them.

As described above for the minimum adenovirus sequences, those gene sequences not present in the adenovirus portion of the hybrid vector must be supplied by either a packaging cell line and/or a helper adenovirus to generate the recombinant hybrid viral particle. Uptake of this hybrid virus by the cell is caused by the infective ability contributed to the vector by the adenovirus and AAV sequences. Once the virus or virus conjugate is taken up by a cell, the AAV ITR flanked transgene must be rescued from the parental adenovirus backbone. Rescue of the transgene is dependent upon supplying the infected cell with an AAV rep gene.

The AAV rep gene can be supplied to the hybrid virus by several methods described in the above-incorporated application. One embodiment for providing rep proteins in trans is by transfecting into the target monolayer of cells previously infected with the hybrid vector, a liposome enveloped plasmid containing the genes encoding the AAV rep 78 kDa and 52 kDa proteins under the control of the AAV P5 promoter. More preferably for in vivo use, the AAV rep gene may also be delivered as part of the hybrid virus. One embodiment of this single particle concept is supplied by a polycation conjugate of hybrid virus. Infection of this modified virus conjugate is accomplished in the same manner and with regard to the same target cells as identified above. However, the polylysine conjugate of the hybrid virus onto which was directly complexed a plasmid that encoded the rep 78 and 52 proteins, combines all of the functional components into a single particle structure. Thus, the hybrid virus conjugate permits delivery of a single particle to the cell, which is considerably more desirable for therapeutic use. In another embodiment, the hybrid virus is modified by cloning the rep cDNA directly into the adenovirus genome portion of the hybrid vector.

These and additional aspects of this hybrid vector are provided by the above-incorporated by reference application.

C. Production of the Recombinant Viral Particle

1. Helper Viruses/Packaging Cell Lines

Depending upon the adenovirus gene content of the plasmid vectors employed to carry the VLDLR minigene, a packaging cell line or a helper adenovirus or both may be necessary to provide sufficient adenovirus gene sequences necessary to produce an infective recombinant viral particle containing the VLDLR minigene.

Useful helper viruses contain selected adenovirus gene sequences not present in the adenovirus vector construct or expressed by the cell line in which the vector is transfected. A preferred helper virus is desirably replication defective and contains a variety of adenovirus genes in addition to the modified sequences described above. In this setting, the helper virus is desirably used in combination with a packaging cell line that stably expresses adenovirus genes. Helper viruses may also be formed into poly-cation conjugates as described in Wu et al, *J. Biol. Chem.*, 264:16985–16987 (1989); K. J. Fisher and J. M. Wilson, *Biochem. J.*, 299:49 (Apr. 1, 1994), and in U.S. patent application Ser. No. 08/331,381, incorporated by reference herein.

Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification. The construction of desirable helper cells is within the skill of the art.

As one example, if the cell line employed to produce the viral vector is not a packaging cell line, and the vector contains only the minimum adenovirus sequences identified above, the helper virus may be a wild type Ad vector supplying the necessary adenovirus early genes E1, E2a, E4 and all remaining late, intermediate, structural and non-structural genes of the adenovirus genome. However, if, in this situation, the packaging cell line is 293, which supplies the E1 proteins, the helper cell line need not contain the E1 gene.

In another embodiment, if the adenovirus vector construct is replication defective (no E1 gene and optionally no E3 gene) and the 293 cell line is employed, no helper virus is necessary for production of the hybrid virus. E3 may be eliminated from the helper virus because this gene product is not necessary for the formation of a functioning virus particle.

Preferably, to facilitate purification and reduce contamination of the viral vector particle with the helper virus, it is useful to modify the helper virus' native adenoviral gene sequences which direct efficient packaging, so as to substantially disable or "cripple" the packaging function of the helper virus or its ability to replicate.

A desirable "crippled" adenovirus is modified in its 5' ITR packaging/enhancer domain, which normally contains at least seven distinct yet functionally redundant sequences necessary for efficient packaging of replicated linear adenovirus genomes ("PAC" sequences). Within a stretch of nucleotide sequence from bp 194–358 of the Ad5 genome, five of these PAC sequences are localized: PAC I or its complement at bp 241–248 [SEQ ID NO: 4], PAC II or its complement at bp 262–269 [SEQ ID NO: 5], PAC III or its complement at bp 304–311 [SEQ ID NO: 6], PAC IV or its complement at bp 314–321 [SEQ ID NO: 7], and PAC V or its complement at bp 339–346 [SEQ ID NO: 8].

Mutations or deletions may be made to one or more of these PAC sequences in an adenovirus helper virus to generate desirable crippled helper viruses. Modifications of this domain may include 5' adenovirus sequences which contain less than all five of the native adenovirus PAC sequences, including deletions of contiguous or non-contiguous PAC sequences. An alternative modification may be the replacement of one or more of the native PAC sequences with one or more repeats of a consensus sequence containing the most frequently used nucleotides of the five native PAC sequences. Alternatively, this adenovirus region may be modified by deliberately inserted mutations which disrupt one or more of the native PAC sequences. One of skill in the art may further manipulate the PAC sequences to similarly achieve the effect of reducing the helper virus packaging efficiency to a desired level.

It should be noted that one of skill in the art may design other helper viruses or develop other packaging cell lines to complement the adenovirus deletions in the vector construct and enable production of the recombinant virus particle, given this information. Therefore, the use or description of any particular helper virus or packaging cell line is not limiting.

In the presence of other packaging cell lines which are capable of supplying adenoviral proteins in addition to the E1, the helper virus may accordingly be deleted of the genes encoding these adenoviral proteins. Such additionally deleted helper viruses also desirably contain crippling modifications as described above.

Poly-cation helper virus conjugates, which may be associated with a plasmid containing other adenoviral genes, which are not present in the helper virus may also be useful. The helper viruses described above may be further modified by resort to adenovirus-polylysine conjugate technology. See, e.g., Wu et al, cited above; and K. J. Fisher and J. M. Wilson, cited above.

Using this technology, a helper virus containing preferably the late adenoviral genes is modified by the addition of a poly-cation sequence distributed around the capsid of the helper virus. Preferably, the poly-cation is poly-lysine, which attaches around the negatively-charged vector to form an external positive charge. A plasmid is then designed to express those adenoviral genes not present in the helper virus, e.g., the E1, E2 and/or E4 genes. The plasmid associates to the helper virus-conjugate through the charges on the poly-lysine sequence. This conjugate permits additional adenovirus genes to be removed from the helper virus and be present on a plasmid which does not become incorporated into the virus during production of the recombinant viral vector. Thus, the impact of contamination is considerably lessened.

2. Assembly of Viral Particle and Infection of a Cell Line

Assembly of the selected DNA sequences of the adenovirus, the AAV and the reporter genes or therapeutic genes and other vector elements into the hybrid vector and the use of the hybrid vector to produce a hybrid viral particle utilize conventional techniques. Such techniques include conventional cloning techniques of cDNA such as those described in texts [Sambrook et al, cited above], use of overlapping oligonucleotide sequences of the adenovirus and AAV genomes, polymerase chain reaction, and any suitable method which provides the desired nucleotide sequence. Standard transfection and co-transfection techniques are employed, e.g., $CaPO_4$ transfection techniques using the complementation 293 cell line. Other conventional methods employed include homologous recombination of the viral genomes, plaquing of viruses in agar overlay, methods of measuring signal generation, and the like.

For example, following the construction and assembly of the desired minigene-containing plasmid vector, the vector is infected in vitro in the presence of an optional helper virus and/or a packaging cell line. Homologous recombination occurs between the helper and the vector, which permits the adenovirus-transgene sequences in the vector to be replicated and packaged into virion capsids, resulting in the recombinant vector viral particles. The current method for producing such virus particles is transfection-based. Briefly, helper virus is used to infect cells, such as the packaging cell line human HEK 293, which are then subsequently transfected with an adenovirus plasmid vector containing a VLDLR transgene by conventional methods. About 30 or more hours post-transfection, the cells are harvested, an extract prepared and the recombinant virus vector containing the VLDLR transgene is purified by buoyant density ultracentrifugation in a CsCl gradient.

The yield of transducing viral particles is largely dependent on the number of cells that are transfected with the plasmid, making it desirable to use a transfection protocol with high efficiency. One such method involves use of a poly-L-lysinylated helper adenovirus as described above. A plasmid containing the VLDLR minigene is then complexed directly to the positively charged helper virus capsid, resulting in the formation of a single transfection particle containing the plasmid vector and the helper functions of the helper virus.

II. Use of the Recombinant Virus Vectors in Gene Therapy

The resulting recombinant adenoviral vector containing the VLDLR minigene produced by cooperation of the adenovirus vector and helper virus or adenoviral vector and packaging cell line, as described above, thus provides an efficient gene transfer vehicle which can deliver the VLDLR gene to a patient in vivo or ex vivo and provide for integration of the gene into a liver cell.

The above-described recombinant vectors are administered to humans in a conventional manner for gene therapy and serve as an alternative or supplemental gene therapy for LDL receptor deficiencies or other lipoprotein metabolic disorders. A viral vector bearing the VLDLR gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The viral vectors are administered in sufficient amounts to transfect the liver cells and provide sufficient levels of transfer and expression of the VLDLR gene to provide a therapeutic benefit without undue adverse or with medically acceptable physiological effects which can be determined by those skilled in the medical arts. Conventional and pharmaceutically acceptable routes of administration include direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 20 to about 100 ml of saline solution containing concentrations of from about $1\times10^9$ to $1\times10^{11}$ pfu/ml virus vector. A preferred human dosage is estimated to be about 50 ml saline solution at $2\times10^{10}$ pfu/ml. The dosage will be adjusted to balance the therapeutic benefit against any side effects. The levels of expression of the VLDLR gene can be monitored to determine the frequency of dosage administration.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector.

Immune modulators for use in inhibiting neutralizing antibody formation are selected based on the determination of the immunoglobulin subtype of any neutralizing antibody produced in response to the VLDLR-containing adenovirus vector. For example, if the neutralizing antibody is a $T_{H2}$ mediated antibody, such as IgA, the immune modulator desirably suppresses or prevents the interaction of $T_{H2}$ with B cells. Alternatively, if the neutralizing antibody is a $T_{H1}$ mediated antibody, such as $IgG_{2A}$, the immune modulator desirably suppresses or prevents the interaction of $T_{H1}$ with B cells.

The neutralizing antibody which develops in response to administration of a viral vector of this invention can be based on what vehicle is being used to deliver the vector and/or the location of delivery. For instance, administration of adenoviral vectors via the lungs generally induces production of IgA neutralizing antibody. Administration of adenoviral vectors via the blood generally induces $IgG_1$ neutralizing antibody. The determination of the neutralizing antibody is readily determined in trials of the selected viral vector in animal models.

Where the reduction of CTL elimination of the viral vectors is desired, the immune modulator is selected for its ability to suppress or block $CD4+T_{H1}$ cells to permit prolonged residence of the viral vector in vitro.

A desirable immune modulator which selectively inhibits the CD4+T cell subset $T_{H2}$ function at the time of primary administration of the viral vector includes interleukin-12, which enhances antigen specific activity of $T_{H1}$ cells at the expense of the $T_{H2}$ cell function [see, e.g., European Patent Application No. 441,900; P. Scott, *Science*,260:496 (1993); R. Manetti et al, *J. Exp. Med.*, 177:1199 (1993); A.

D'Andrea et al, *J. Exp. Med.*, 176:1387 (1992)]. Another selected immune modulator which performs the same function is gamma interferon [S. C. Morris et al, *J. Immunol.*, 152:1047 (1994); F. P. Heinzel et al, *J. Exp. Med.*, 177:1505 (1993)]. Preferably, such immune modulators are in the form of human recombinant proteins. These proteins are currently commercially available or may be produced by methods extant in the art. It is also anticipated that active peptides, fragments, subunits or analogs of IL-12 or gamma interferon which share the $T_{H2}$ inhibitory function of these proteins, will also be useful in this method step when the neutralizing antibodies are $T_{H2}$ mediated.

A desirable immune modulator for use in this step of the method which selectively inhibits the CD4+ T cell subset $T_{H1}$ function at the time of primary administration of the viral vector includes interleukin-4, which enhances antigen specific activity of $T_{H2}$ cells at the expense of the $T_{H1}$ cell function [see, e.g., Yokota et al, *Proc. Natl. Acad. Sci., USA*, 83:5894–5898 (1986); U.S. Pat. No. 5,017,691].

Still other immune modulators which inhibit the $T_H$ function may also be employed. Among such modulators are agents that specifically inhibit or deplete CD4+cells, for example, antibody to the CD4 protein. Among such agents include anti-T cell antibodies, such as anti-OKT 3+ [see, e.g., U.S. Pat. No. 4,658,019; European Patent Application No. 501,233, published Sep. 2, 1992, among others]. See, the examples which employ the commercially available antibody GK1.5 (ATCC Accession No. TIB207) to deplete CD4+$T_{H1}$ cells. Depletion of CD4+ cells is shown to inhibit the CTL elimination of the viral vector.

Alternatively, any agent that interferes with the activation of B cells by $T_H$ cells is useful. For example, it is necessary for the activation of B cells by T cells for certain interactions to occur [F. H. Durie et al, *Immunol. Today*, 15(9):406–410 (1994)], such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

Thus, agents which can block the interactions necessary for B cell activation by T helper cells, and thus neutralizing antibody formation can be used as immune modulators. An agent which blocks the CD40 ligand on the $T_H$ cell interferes with the normal binding of CD40 ligand on the T helper cell with the CD40 antigen on the B cell. Thus, a soluble CD40 molecule or an antibody to CD40 ligand [available from Bristol-Myers Squibb Co; see, e.g., European patent application 555,880, published Aug. 18, 1993] can be a selected immune modulator.

Alternatively, an agent which blocks the CD28 and/or CTLA4 ligands present on T helper cells interferes with the normal binding of those ligands with the antigen B7 on the B cell. Thus, a soluble form of B7 or an antibody to CD28 or CTLA4, e.g., CTLA4-Ig [available from Bristol-Myers Squibb Co; see, e.g., European patent application 606,217, published Jul. 20, 1994] can be the selected immune modulator.

Although less desirable than the above-listed immune modulators, other immune modulators or agents that non-specificly inhibit immune function, i.e., cyclosporin A or cyclophosphamide, may be useful in this method step.

A suitable amount or dosage of the immune modulator will depend primarily on the amount of the recombinant vector bearing the VLDLR gene which is initially administered to the patient and the type of immune modulator selected. Other secondary factors such as the condition being treated, the age, weight, general health, and immune status of the patient, may also be considered by a physician in determining the dosage of immune modulator to be delivered to the patient. Generally, for example, a therapeutically effective human dosage of a cytokine immune modulator, e.g., IL-12 or γ-IFN, is generally in the range of from about 0.5 µg to about 5 mg per about $1 \times 10^7$ pfu/ml virus vector. Various dosages may be determined by one of skill in the art to balance the therapeutic benefit against any side effects.

It is presently preferred to administer the modulator just prior to the administration of the vector. The immune modulator may be administered separately from the recombinant vector, or, if desired, it may be administered in admixture with the recombinant vector. The immune modulator may be administered in a pharmaceutically acceptable carrier or diluent, such as saline. Alternatively, the immune modulator may be itself administered as DNA, either separately from the vector or admixed with the recombinant vector bearing the VLDLR gene. Methods exist in the art for the pharmaceutical preparation of the modulator as protein or as DNA [See, e.g., J. Cohen, *Science*, 259:1691–1692 (1993) regarding DNA vaccines]. Desirably the immune modulator is administered by the same route as the recombinant vector.

The optional administration of the selected immune modulator may be repeated during the treatment with the recombinant adenovirus vector carrying the human VLDLR gene, during the period of time that the VLDLR gene is expressed (as monitored by e.g., LDL levels), or with every booster of the recombinant vector.

Thus, the compositions and methods of this invention provide a desirable treatment for defects in LDL metabolism, by providing stable expression of the VLDLR gene in human hepatocytes, and the ability to re-administer the vector as desired without incurring an undesired immune response by the patient.

The following examples illustrate the construction and testing of the viral vectors and VLDL receptor gene inserts of the present invention and the use thereof in the treatment of metabolic disorders. An exemplary recombinant adenovirus encoding the human VLDL receptor was constructed as described in Example 1 below. These examples are illustrative only, and do not limit the scope of the present invention.

EXAMPLE 1

Construction and Purification of H5.010CMVVLDLR

The cDNA for the human very low density lipoprotein (VLDL) receptor [M. E. Gafvels et al, cited above; SEQ ID NO: 1] was inserted into the HindIII site of plasmid pRc/CMV (obtained from Invitrogen Corp.). The resulting plasmid, pRc/CMVVLDLR, was digested with the restriction enzymes SnaBI and NotI and the 4 kb fragment containing the cytomegalovirus (CMV) immediate-early promoter and VLDL receptor cDNA was isolated.

Figure 2:
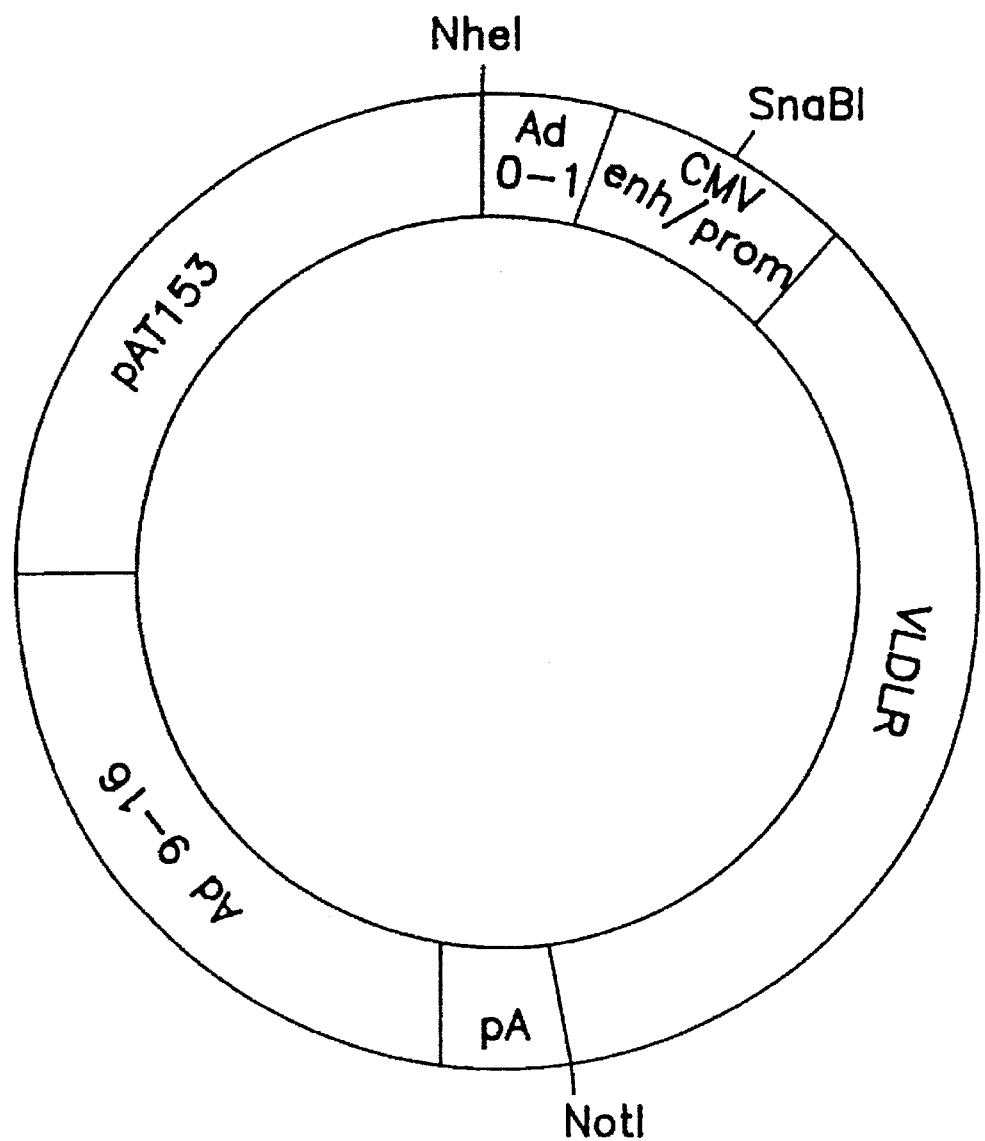
FIG. 2 is a schematic drawing of plasmid pAd.CMVVLDLR, which contains adenovirus map units 0–1 (Ad 0–1), followed by a cytomegalovirus enhancer/promoter (CMV enh/prom), a human VLDLR gene, a polyadenylation signal (pA), adenovirus map units 9–16 (Ad 9–16) and plasmid sequences from plasmid pAT153 including an origin of replication and ampicillin resistance gene. Restriction endonuclease enzymes are represented by conventional designations in the plasmid construct.

The plasmid pAd.CMVlacZ [Kozarsky II, cited above] was digested with SnaBI and NotI and the 5.6 kb backbone was isolated. The two fragments were ligated to generate pAd.CMVVLDLR (FIGS. 2 and 9; SEQ ID NO: 3). pAd.CMVVLDLR was linearized with NheI and co-transfected into 293 cells with sub360 DNA (derived from adenovirus type 5) which had been digested with XbaI and ClaI as previously described [K. F. Kozarsky I and II cited above].

Figure 3:
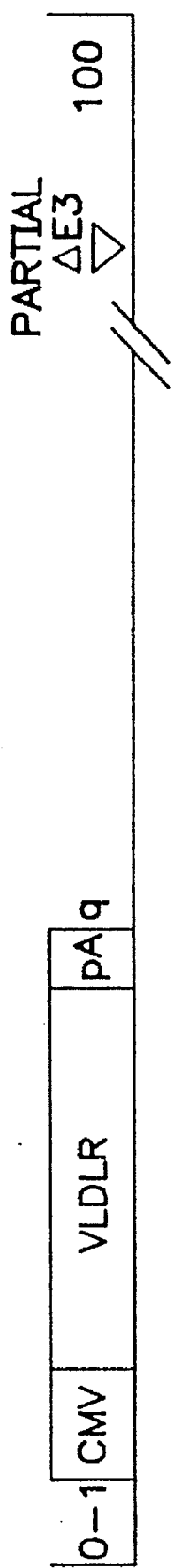
FIG. 3 is a schematic map of recombinant adenovirus H5.010CMVVLDLR, in which 0 to 100 represent the map units of an adenovirus type 5 (Genbank Accession No. M73260), and the CMV/VLDLR/pA minicassette of pAd.CMVVLDLR inserted between adenovirus m.u.1 and 9, with the remaining Ad5 map unit 9–100 having a partial E3 gene deletion between about map unit 78.5 and about 84.3.

The resulting recombinant adenovirus, designated H5.010CMVVLDLR contains the sequence from about nucleotide 12 to about 4390 of pAd.CMVVLDLR and Ad.5 map units 9–100 with a small deletion in the E3 gene (see GenBank Accession No. M73260) and discussion of FIG. 3. This recombinant adenovirus was isolated following two rounds of plaque purification. H5.010CMVVLDLR was grown on 293 cells and purified by two rounds of cesium chloride density centrifugation as previously described [K. F. Kozarsky I and II cited above]. Cesium chloride was removed by passing the virus over a BioRad DG10 column using phosphate-buffered saline.

For rabbit experiments, virus was used freshly purified; for mouse experiments virus was either used fresh, or after column purification glycerol was added to a final concentration of 10% (v/v), and virus was stored at −70° C. until use.

As described in the following examples, this recombinant adenovirus vector was introduced into the livers of WHHL rabbits and into the livers of LDL receptor knockout mice to determine the in vivo function of the VLDL receptor, and to determine its usefulness as an alternative or supplemental gene therapy for LDL receptor deficiency.

EXAMPLE 2

Other Recombinant Adenoviruses

H5.010CMVlacZ, encoding the lacZ gene under the control of the CMV enhancer/promoter, and H5.010CBhLDLR, encoding the human low density lipoprotein (LDL) receptor cDNA under the control of the CMV-enhanced chicken β-actin promoter, were prepared as previously described [K. F. Kozarsky I and II, cited above].

EXAMPLE 3

Effects of Hepatic Expression of the VLDL Receptor in the WHHL Rabbit

H5.010CMVVLDLR or H5.010CMVlacZ (encoding the β-galactosidase gene), obtained as described in Examples 1 and 2, was infused intravenously into WHHL rabbits [Camm Research] as follows. Rabbits were infused with $7.5 \times 10^{12}$ particles of either recombinant adenovirus through a marginal ear vein on day 0. In addition, two New Zealand White (NZW) rabbits [Hazleton, Inc.] were infused with each virus and sacrificed on day 5 post-infusion to document the extent of gene transfer in the liver.

Rabbits were maintained in a 12 hour light/dark cycle on a Purina laboratory chow, delivered each day at approximately 11:00 am. Venous samples were obtained through a marginal ear vein at approximately 10:00 am on the days indicated.

A. Plasma Analyses

Plasma samples were analyzed for total cholesterol using the Cholesterol HP kit and Preciset standards (Boehringer Mannheim).

Figure 4A:
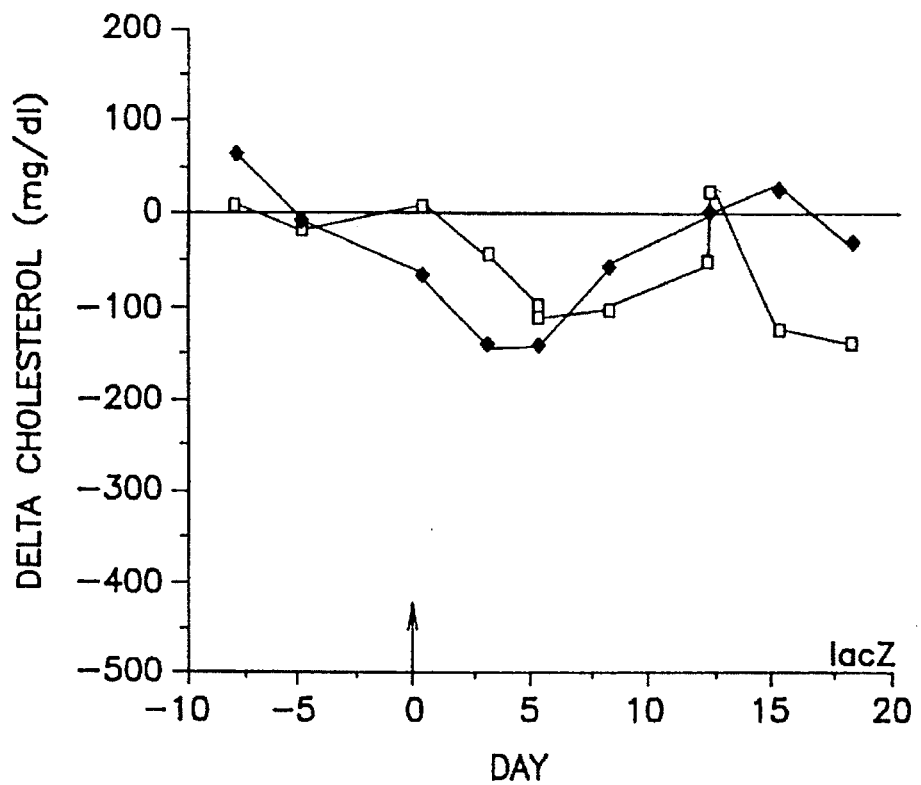
FIG. 4A is a graph plotting changes in plasma cholesterol levels in mg/dl for WHHL rabbits vs. days before and after receiving recombinant adenovirus H5.010CMVlacZ. The symbols represent individual animals. See Example 3.
Figure 4B:
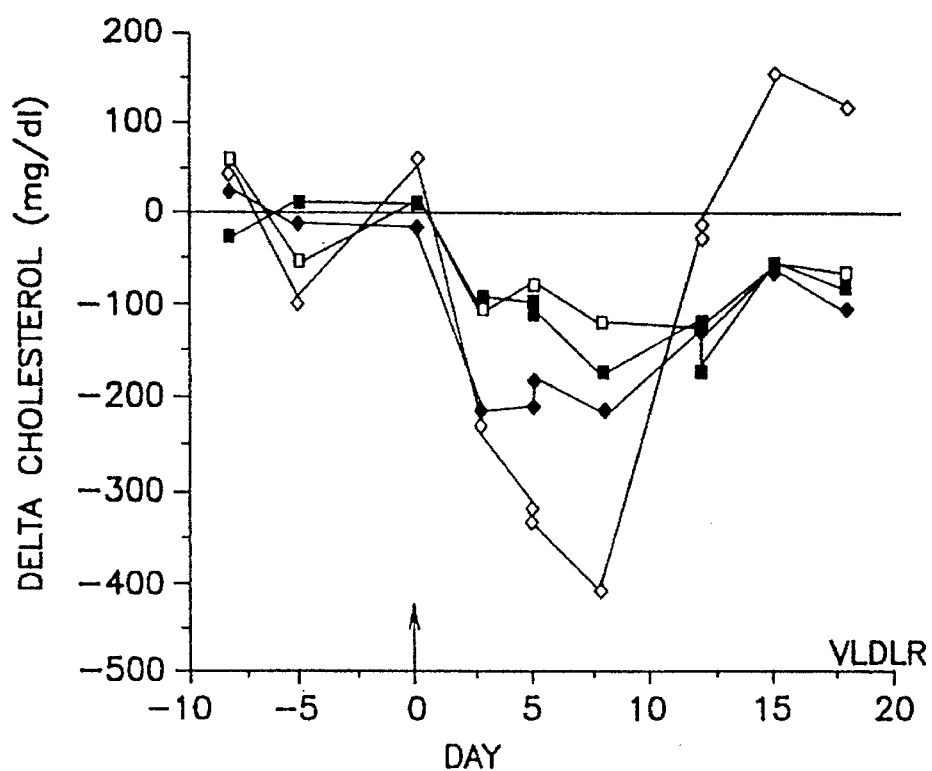
FIG. 4B is a graph plotting changes in plasma cholesterol levels in mg/dl for WHHL rabbits vs. days before and after receiving recombinant adenovirus H5.010CMVVLDLR. The symbols represent the response of four individual animals. See Example 3.

Plasma cholesterol levels were evaluated in each of the WHHL rabbits before and after receiving recombinant adenovirus. FIG. 4A shows that rabbits infused with H5.010CMVlacZ had no significant changes in cholesterol levels. However, following infusion with H5.010CMVVLDLR, cholesterol levels dropped, with maximum decreases that ranged from 140 to 420 mg/dl (FIG. 4B). This demonstrated that expression of the VLDL receptor results in decreased cholesterol levels in LDL receptor-deficient rabbits.

B. Histochemical Analysis

Portions of liver were paraffin embedded, sectioned, and stained with hematoxylin and eosin. Some portions were fresh-frozen, sectioned, fixed in glutaraldehyde, stained with X-gal and lightly counterstained with hematoxylin. Some fresh-frozen sections were fixed in methanol, and then stained with either a polyclonal anti-β-galactosidase antibody (5 prime-3 prime), a polyclonal anti-human LDL receptor antibody, or with a polyclonal anti-VLDL receptor antibody, followed by a fluorescein isothiocyanate-conjugated anti-rabbit antibody (Jackson Immunoresearch) as previously described [K. F. Kozarsky I and II cited above]. Oil Red 0 staining was performed on fresh-frozen sections fixed for 1 minute in 37% formaldehyde, then rinsed and stained in Oil Red O (3 parts 0.5% Oil Red O in isopropyl alcohol/2 parts water) for 10 minutes. Slides were counterstained in hematoxylin and mounted in aqueous solution.

Immunofluorescence analysis of the infused rabbits showed that approximately 50% of hepatocytes from the rabbit infused with H5.010CMVlacZ expressed β-galactosidase, liver tissue from the rabbit infused with H5.010CMVVLDLR had a slightly higher percentage of hepatocytes expressing the VLDL receptor. In agreement with Northern blot analysis showing little or no VLDL receptor mRNA expression [M. E. Gafvels et al, cited above], liver from the lacZ-infused rabbit showed no reactivity with the anti-VLDL receptor antibody.

EXAMPLE 4

Effects of Short-Term Hepatic Expression of the VLDL Receptor in LDL Receptor Knockout Mice C57Bl/6 mice and LDL receptor knockout mice (Jackson Labs) were infused intravenously with 0.5 or $1.0 \times 10^{10}$ particles of recombinant adenovirus through the tail vein and cholesterol levels were monitored before and after infusion.

Specifically, three mice each were infused with either H5.010CMVlacZ, H5.010CMVVLDLR, or H5.010CBhLDLR (encoding the human LDL receptor cDNA). This last virus was included as a control to confirm published results [Kozarsky I and II cited above]. Plasma samples were obtained by retroorbital bleeds using heparinized capillary tubes. The LDL receptor knockout mice were maintained upon a high cholesterol diet composed of Purina mouse chow supplemented with 1.25% cholesterol, 7.5% cocoa butter, 7.5% casein, and 0.5% cholate (1.25% cholesterol diet) for at least 3 weeks immediately following weaning before experiments were initiated. Mice were sacrificed on day 5 post-infusion.

Liver tissues were analyzed by immunofluorescence for transgene expression by the techniques described in Example 3, and plasma cholesterol levels were measured as similarly described. For lipoprotein fractionations, plasma from triplicate LDL receptor knockout mice were pooled, subjected to density ultracentrifugation, fractions were collected, and the cholesterol content was determined by conventional means.

Immunofluorescence analysis revealed moderate levels of β-galactosidase expression in H5.010CMVlacZ-infused mice, and higher levels of either human LDL receptor and VLDL receptor expression in H5.010CBhLDLR- and in H5.010CMVVLDLR-infused mice, respectively.

Figure 5:
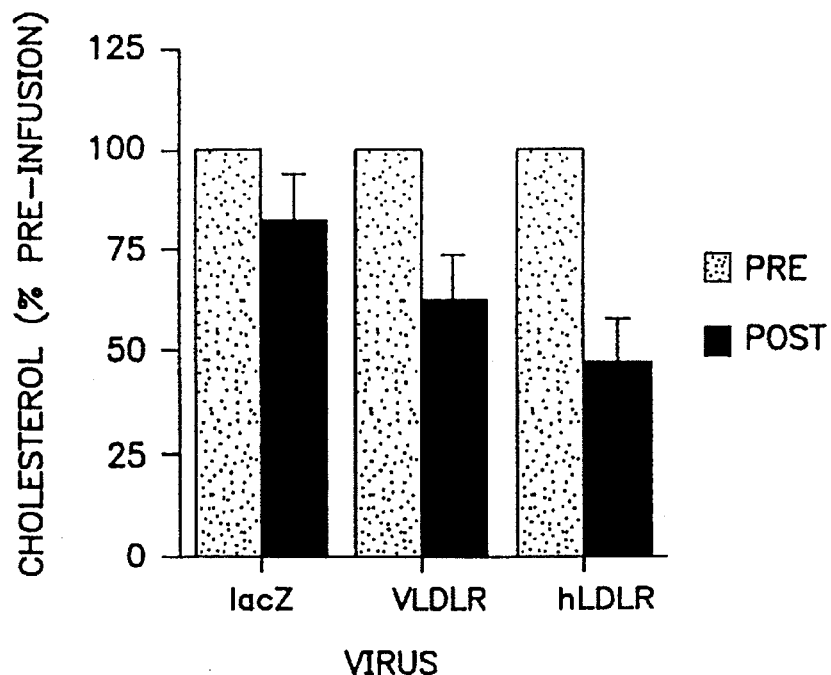
FIG. 5 is a bar graph representing cholesterol levels (measured as % pre-infusion) in mice infused with recombinant adenovirus H5.010CMVlacZ (lacZ), recombinant adenovirus H5.010CMVVLDLR and recombinant adenovirus H5.010CBhLDLR. The dotted bars represent pre-infusion levels and the solid bars represent post-infusion levels. See Example 4.
Figure 6:
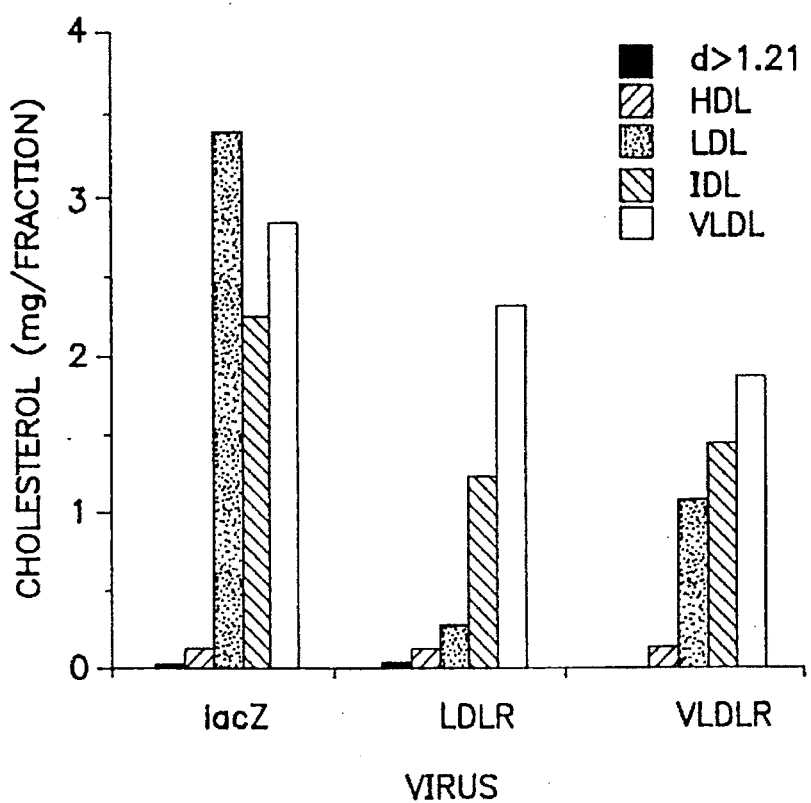
FIG. 6 is a bar graph representing cholesterol levels, specifically the levels of the fractions of plasma lipoproteins (measured as mg/fraction) in mice infused with recombinant adenovirus H5.010CMVlacZ (lacZ), recombinant adenovirus H5.010CMVVLDLR and recombinant adenovirus H5.010CBhLDLR. The solid bars represent proteins or fragments falling within a density (d)>1.21; the thickly cross-hatched bars represent HDL; the closely cross-hatched bars represent LDL, the spaced apart slanted hatched bars represent intermediate density lipoprotein (IDL), and the clear bars represent VLDL levels. See Example 4.

Cholesterol levels decreased slightly in the control, H5.010CMVlacZ-infused mice (FIG. 5), probably due to non-transgene-related effects of infusion of recombinant adenovirus, which can result in hepatotoxicity in mice [Y. Yang et al, Proc. Natl. Acad. Sci., USA, 91:4407–4411 (May 1994)]. However, in contrast to the decrease observed in the control mice, cholesterol levels dropped significantly to 50% of pre-infusion values in the H5.010CBhLDLR-infused mice on day 5 post-infusion. Cholesterol levels in the H5.010CMVVLDLR-infused mice also decreased, to approximately 60% of pre-infusion levels. Further analysis of plasma lipoproteins showed that in the H5.010CBhLDLR-treated mice, LDL levels plummeted, with additional decreases in IDL and VLDL fractions (FIG. 6). The H5.010CMVVLDLR-infused mice showed a larger decrease in the VLDL fraction with less of a decrease in LDL.

Taken together, these data indicate that hepatic expression of VLDL receptor results in increased clearance of VLDL from the plasma, resulting in decreases in the amounts of lipoproteins for which VLDL is the precursor (i.e., IDL and LDL), and an overall drop in total plasma cholesterol.

EXAMPLE 5

Effects of Long-Term Hepatic Expression of the VLDL Receptor in LDL Receptor Knockout Mice In order to achieve cholesterol levels closer to those observed in both FH patients and WHHL rabbits, LDL receptor knockout mice were maintained on a high cholesterol diet composed of Purina mouse chow supplemented with 0.2% cholesterol, 10% coconut oil, and 0.05% cholate (0.2% cholesterol diet). Cholesterol levels in these mice ranged from 930 to 1550 mg/dl, whereas the mice on the 1.25% cholesterol (Example 4) diet had levels of 1900 to 3100 mg/dl.

Three mice were each infused with $1 \times 10^{11}$ particles of a recombinant adenovirus selected from H5.010CBhLDLR, H5.010CMVVLDLR, or H5.010CMVlacZ. One mouse from each group was sacrificed on day 5 post-infusion to document the extent of gene transfer.

Immunofluorescence staining showed that most of the hepatocytes expressed the transgene product, either β-galactosidase, human LDL receptor, or VLDL receptor. Hematoxylin and eosin staining of sections of liver revealed essentially normal morphology in the H5.010CMVlacZ-infused mouse. However, for both the H5.010CBhLDLR- and H5.010CMVVLDLR-infused mice, hepatocytes appeared to have vacuoles within. When tissue was analyzed with Oil Red O staining, a stain for neutral lipids, liver from the receptor-infused animals clearly showed accumulation of large droplets of lipid when compared with the lacZ control. This suggested that short-term, high level expression of the LDL receptor or VLDL receptor in these LDL receptor-deficient mice resulted in intracellular accumulation of lipids.

Figure 7A:
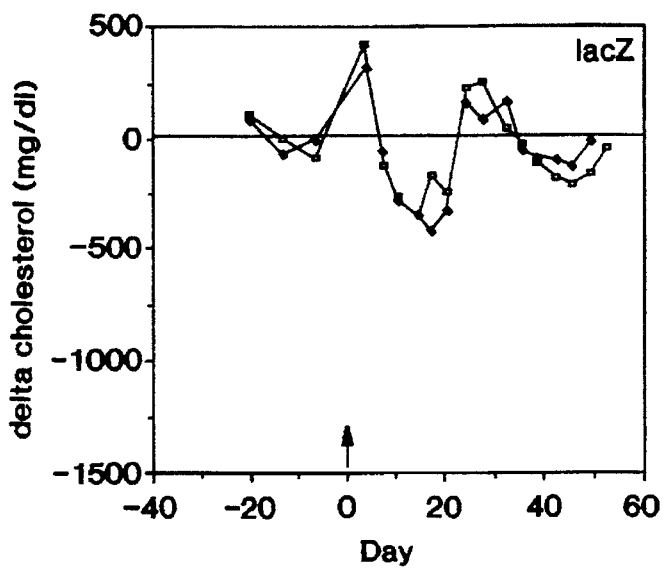
FIG. 7A is a graph plotting changes in cholesterol levels (measured in mg/dl) vs. days pre- and post-infusion for mice infused with H5.010CMVlacZ. The symbols represent the responses of individual animals. See Example 5.
Figure 7B:
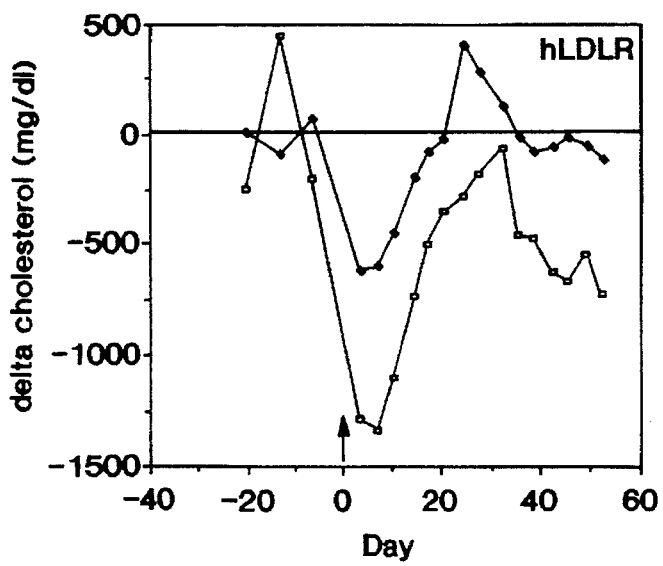
FIG. 7B is a graph plotting changes in cholesterol levels (measured in mg/dl) vs. days pre- and post-infusion for mice infused with H5.010CBhLDLR. The symbols are the same as for FIG. 7A. See Example 5.
Figure 7C:
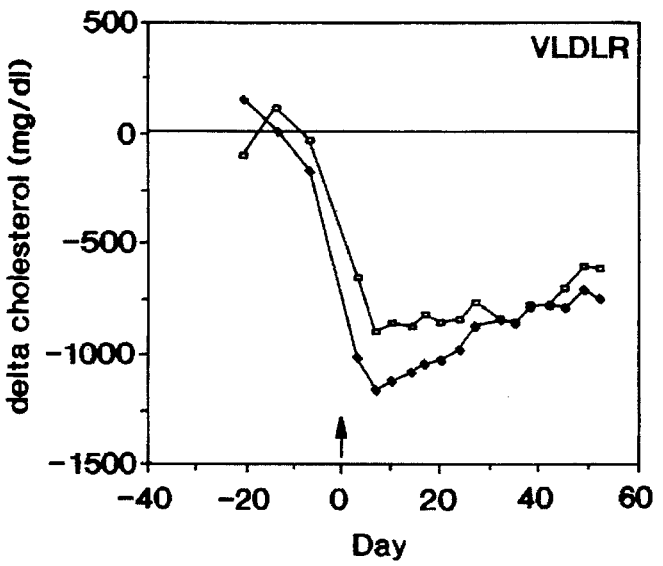
FIG. 7C is a graph plotting changes in cholesterol levels (measured in mg/dl) vs. days pre and post-infusion for mice infused with H5.010CMVVLDLR. The symbols are the same as for FIG. 9A. See Example 5.

To confirm the biologic activities of the transgene products, plasma cholesterol levels were followed before and after recombinant adenovirus administration. FIG. 7A shows that cholesterol levels in H5.010CMVlacZ-infused mice do not change significantly over time. Mice infused with H5.010CBhLDLR have a large but transient decrease in cholesterol (see, FIG. 7B). This is consistent with previous data indicating that recombinant adenovirus-mediated transgene expression is transient in mouse liver in large part or entirely due to the development of an immune response to the adenovirus-infected cells. Mice infused with H5.010CMVVLDLR showed large decreases in plasma cholesterol which paralleled those seen in the H5.010CBhLDLR-infused mice (FIG. 7C). Surprisingly, however, the decreases in cholesterol levels in the H5.010CMVVLDLR-infused mice (FIG. 7A) were sustained at least through 7 weeks following infusion (the current duration of the experiment). These data suggest that expression of the VLDL receptor in the liver is an effective therapy for hypercholesterolemia.

At the same time of infusion of the LDL receptor knockout mice, normal C57Bl/6 mice were infused with each of the recombinant adenoviruses. These mice were sacrificed on day 24 post-infusion, and immunofluorescence performed on liver tissues. This demonstrated that expression of β-galactosidase and of the human LDL receptor was nearly undetectable at this time point. In contrast, two mice infused with H5.010CMVVLDLR expressed the VLDL receptor at high levels. The percent of hepatocytes may have decreased slightly as compared to the day 5 mice. These data suggest that the sustained decrease in plasma cholesterol levels in the H5.010CMVVLDLR-infused mice was due to sustained expression of the VLDL receptor.

Western blots were performed using sera from these mice to determine the presence or absence of an immune response to the transgene products. Mice infused with H5.010CMVlacZ developed antibodies to β-galactosidase. In addition, mice infused with H5.010CBhLDLR synthesized antibodies to the human LDL receptor. However, antibodies to the VLDL receptor were undetectable in the mice infused with H5.010CMVVLDLR. This suggested that the VLDL receptor, although the human and not the mouse sequence was used, was not immunogenic in these mice. The amino acid sequences of the human and mouse LDL receptors are approximately 78% identical, while the human and mouse VLDL receptors are >94% identical. This increased sequence similarity is likely to account for the absence of antibody development to the human VLDL receptor despite high level expression in the mouse liver as a result of infusion of H5.010CMVVLDLR.

EXAMPLE 6

Stability of Expression of VLDL Receptor

This experiment illustrates relative transgene persistence in mice.

LDL receptor knockout mice were injected intravenously on day 0 with $1 \times 10^{11}$ particles of H5.010CMVlacZ, H5.010CBhLDLR, or H5.010CMVVLDLR. Mice were sacrificed on the indicated days after injection (3, 10 or 21), and fresh-frozen sections of liver were stained with one of X-gal (left column), anti-LDL receptor antibody (middle column) or anti-VLDL receptor antibody (right column) to detect expression of the lacZ gene, followed by a fluorescein-conjugated secondary antibody.

FIGS. 10A through 10L indicate the results, demonstrating that the expression of the VLDL receptor in mice persists longer than expression of either β-galactosidase (lacZ gene) or the human LDL receptor.

EXAMPLE 7

Western Blot to Detect Antibodies to the LDL Receptor and to the VLDL Receptor A. This experiment confirmed earlier work that mice injected with H5.010CBhLDLR develop antibodies to the human LDL receptor.

Two LDL receptor knockout mice (KO20 and KO27) or two normal C57Bl/6 mice were injected via the tail vein with $1 \times 10^{11}$ particles of H5.010CBhLDLR at day 0 and serum samples were collected both before injection (pre), and on days 10, 24,39,52 and 70 following injection for the knockout mice and on day 21 for the C57Bl/6 mice. The positive control (+) was rabbit antiserum to LDL receptor. The negative control (−) was pre-immune rabbit serum.

Lysates were prepared from 24–23 cells, a 3T3 cell line which produces retrovirus encoding the human LDL receptor, were subjected to SDS-polyacrylamide gel electrophoresis, and transferred to nitrocellulose filters. Filters were incubated with sera from the indicated mice, washed, and incubated with peroxidase-conjugated anti-mouse immunoglobulin followed by chemiluminescent substrate.

Figure 11A:
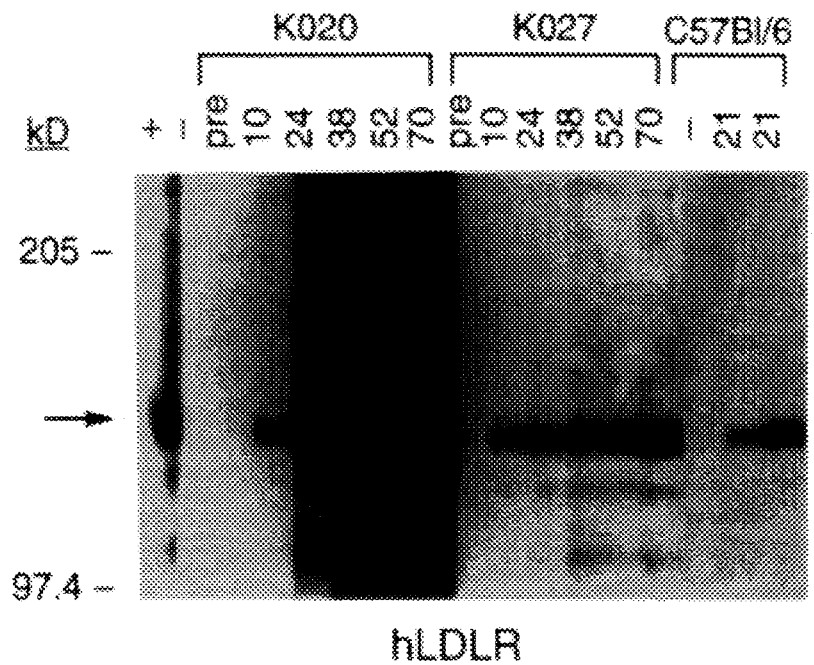
FIG. 11A is a Western gel for the experiment conducted as described in Example 7A. + is the positive control rabbit antiserum to LDL receptor. − is the pre-immune rabbit serum. KO20 and KO27 are LDL receptor knockout mice infused with H5.010CBhLDLR. C57Bl/6 represents two-separate mice infused with H5.010CBhLDLR. "pre" indicates lysates examined prior to injection. The numbers indicate days after injection.

The results are depicted in the Western gel of FIG. 11A, which demonstrated that the mice injected with H5.010CBhLDLR develop antibodies to the human LDL receptor, as indicated by the band at the arrow in the indicated lanes.

B. This experiment confirmed that mice injected with H5.010CMVVLDLR generally do not develop antibodies to the VLDL receptor.

Two individual LDL receptor knockout mice (−/−) and two individual normal (C57Bl/6) mice (+/+) were injected via the tail vein with $1 \times 10^{11}$ particles of H5.010CMVVLDLR and serum samples were collected on the days 24 and 27 after injection or before injection (pre). The positive control (+) was rabbit antibody to the VLDL receptor.

Lysates were prepared from HeLa cells previously infected with H5.010CMVVLDLR, were subjected to SDS-polyacrylamide gel electrophoresis, and transferred to nitrocellulose filters. Filters were incubated with sera from the indicated mice, washed, and incubated with peroxidase-conjugated anti-mouse immunoglobulin followed by chemiluminescent substrate.

Figure 11B:
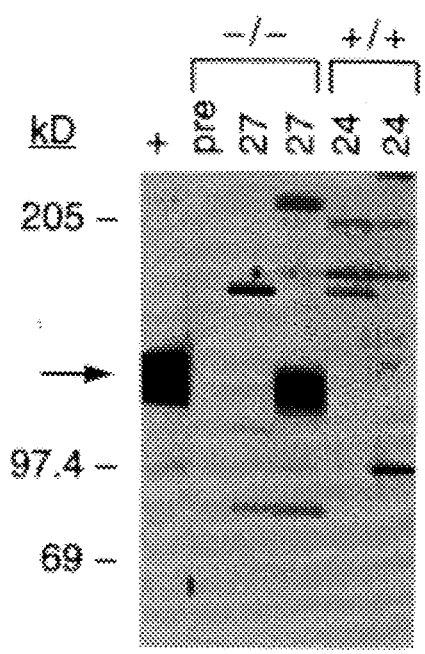
FIG. 11B is a Western gel for the experiment conducted as described in Example 7B. Two individual LDL receptor knockout mice are represented as −/−; two individual normal (C57Bl/6) mice as (+/+); 24 and 27 are days after injection; pre is pre-immune serum. The positive control (+) is rabbit antibody to the VLDL receptor. The arrow indicates the presence of anti-VLDLR antibodies.

The Western gel as shown in FIG. 11B indicated that only a single mouse (an LDL knock-out mouse, 27 day sera) developed antibodies to the VLDL receptor. See, the fourth lane of FIG. 11B.

EXAMPLE 8

Enhancement of Adenovirus Mediated Gene Transfer upon Second Administration by IL-12 and IFN-γ in Mouse Lung The recombinant adenoviruses H5.010CMVlacZ and H5.010CBALP (alkaline phosphatase gene expressed from the CMV enhanced β-actin promoter in the sub360 backbone) were used in this example. Each similar virus expresses a different reporter gene whose expression can be discriminated from that of the first reporter gene.

Female C57Bl/6 mice (6–8 week old) were infected with suspensions of H5.010CBALP ($1 \times 10^9$ pfu in 50 μl of PBS) via the trachea at day 0 and similarly with H5.010CMVlacZ at day 28. One group of such mice was used as a control. Another group of mice were acutely depleted of $CD4^+$ cells by i.p. injection of antibody to $CD4^+$ cells (GK1.5; ATCC No. TIB207, 1:10 dilution of ascites) at the time of the initial gene therapy (days—3, 0, and +3). A third group of mice were injected with IL-12 (1 μg intratracheal or 2 μg, i.p. injections) at the time of the first administration of virus (days 0 and +1). A fourth group of mice were injected with gamma interferon (1 μg intratracheal or 2 μg, i.p. injections) at the time of the first administration of virus (days 0 and +1).

When mice were subsequently euthanized and necropsied at days 3, 28, or 31, lung tissues were prepared for cryosections, while bronchial alveolar lavage (BAL) and mediastinal lymph nodes (MLN) were harvested for immunological assays.

A. Cryosections

The lung tissues were evaluated for alkaline phosphatase expression by histochemical staining following the procedures of Y. Yang et al, cited above. The results are depicted in FIGS. 12A–12L.

Instillation of alkaline phosphatase virus ($10^9$ pfu) into the airway of all groups of the C57Bl/6 mice resulted in high level transgene expression in the majority of conducting airways that diminishes to undetectable levels by day 28. Loss of transgene expression was shown to be due to CTL mediated elimination of the genetically modified hepatocytes [Y. Yang et al, cited above].

In the control mice, no recombinant gene expression was detected three days after the second administration of virus, i.e., day 31.

Administration of virus to the CD4+ depleted animals was associated with high level recombinant transgene expression that was stable for a month (FIGS. 12D–12F). Expression of the second virus was detectable on day 31.

Initial high level gene transfer diminished after about one month in the IL-12 treated mice; however, in contrast to the control, high level gene transfer to airway epithelial cells was achieved when virus was readministered to IL-12 treated animals at day 28, as seen in the day 31 results (FIG. 12G–12I).

The gamma-interferon treated animals were virtually indistinguishable from the animals treated with IL-12 in that efficient gene transfer was accomplished upon a second administration of virus (FIGS. 12J–12L).

B. Immunological Assays—MLN

Lymphocytes from MLN of the control group and IL-12 treated group of C57Bl/6 mice harvested 28 days after administration of H5.010CBALP were restimulated in vitro with UV-inactivated H5.010CMVlacZ at 10 particles/cell for 24 hours. Cell-free supernatants were assayed for the presence of IL-2 or IL-4 on HT-2 cells (an IL-2 or IL-4-dependent cell line) [Y. Yang et al, cited above]. Presence of IFN-γ in the same lymphocyte culture supernatant was measured on L929 cells as described [Y. Yang et al, cited above]. Stimulation index (S.I.) was calculated by dividing $^3$H-thymidine cpm incorporated into HT-2 cells cultured in supernatants of lymphocytes restimulated with virus by those incorporated into HT-2 cells cultured in supernatants of lymphocytes incubated in antigen-free medium.

The results are shown in Table 1 below.

TABLE 1

| | $^3$H-Thymidine Incorporation (cpm ± SD) | | | IFN-γ liter |
|---|---|---|---|---|
| | Medium | H5.010CMVlacZ | S.I. | (IU/ml)$^d$ |
| C57Bl/6 | 175 ± 40 | 2084 ± 66 | 11.91 | 80 |
| anti-IL2 (1:5000) | | 523 ± 81 | 2.98 | |
| anti-IL4 (1:5000) | | 1545 ± 33 | 8.83 | |
| C57Bl/6 + IL12 | 247 ± 34 | 5203 ± 28 | 21.07 | 160 |
| anti-IL2 (1:5000) | | 776 ± 50 | 3.14 | |
| anti-IL4 (1:5000) | | 4608 ± 52 | 18.66 | |

Stimulation of lymphocytes from regional lymph nodes with both recombinant adenoviruses led to secretion of cytokines specific for the activation of both $T_{H1}$ (i.e., IL-2 and IFN-γ) and $T_{H2}$ (i.e., IL-4) subsets of T helper cells (Table 1).

Analysis of lymphocytes from the IL-12 treated animals stimulated in vitro with virus revealed an increased secretion of IL-2 and IFN-γ and a relative decreased production of IL-4 as compared to animals that did not receive IL-12 (i.e., ratio of IL-2/IL-4 was increased from 3 to 6 when IL-12 was used; Table 1).

C. Immunological Assays—BAL

BAL samples obtained from animals 28 days after primary exposure to recombinant virus were evaluated for neutralizing antibodies to adenovirus and anti-adenovirus antibody isotypes as follows. The same four groups of C57Bl/6 mice, i.e., control, CD4⁺ depleted, IL-12 treated and IFN-γ treated, were infected with H5.010CBALP. Neutralizing antibody was measured in serially diluted BAL samples (100 μl) which were mixed with H5.010CBlacZ ($1 \times 10^6$ pfu in 20 μl), incubated for 1 hour at 37° C., and applied to 80% confluent Hela cells in 96 well plates ($2 \times 10^4$ cells per well). After 60 minutes of incubation at 37° C., 100 μl of DMEM containing 20% FBS was added to each well. Cells were fixed and stained for β-galactosidase expression the following day.

All cells were lacZ positive in the absence of anti-adenoviral antibodies.

Adenovirus-specific antibody isotype was determined in BAL by using enzyme-linked immunosorbent assay (ELISA). Briefly, 96-well plates were coated with 100 μl of PBS containing $5 \times 10^9$ particles of H5.010CBlacZ for 18 hours at 4° C. The wells were washed 5 times with PBS. After blocking with 200 μl of 2% BSA in PBS, the plates were rinsed once with PBS and incubated with 1:10 diluted BAL samples for 90 minutes at 4° C. Thereafter, the wells were extensively washed and refilled with 100 μl of 1:1000 diluted alkaline phosphatase-conjugated anti-mouse IgG or IgA (Sigma). The plates were incubated, subsequently washed 5 times, and 100 μl of the substrate solution (p-nitrophenyl phosphate, PNPP) was added to each well. Substrate conversion was stopped by the addition of 50 μl of 0.1M EDTA. Plates were read at 405 nm.

Figure 13A:
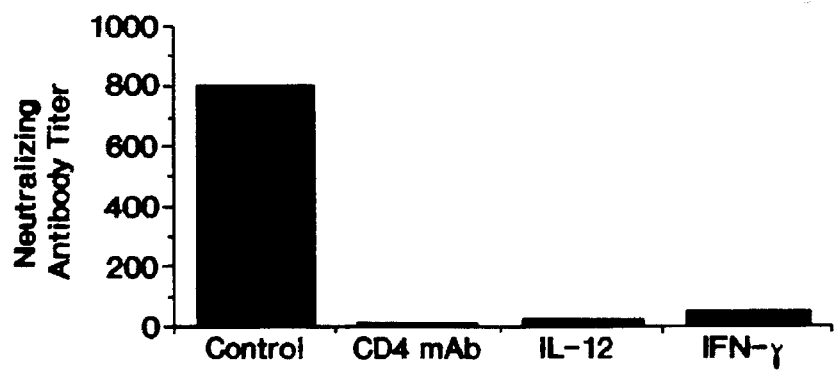
FIG. 13A is a graph summarizing neutralizing antibody titer present in BAL samples of C57Bl/6 mice adenovirus-infected on day 0 and necrotized on day 28 as described in Example 8. Control represents normal mice ("control"); CD4 mAB represents CD4+ depleted mice; IL-12 represents IL-12 treated mice and IFN-γ represent IFN-γ treated mice as described for FIGS. 12A through 12L.
Figure 13B:
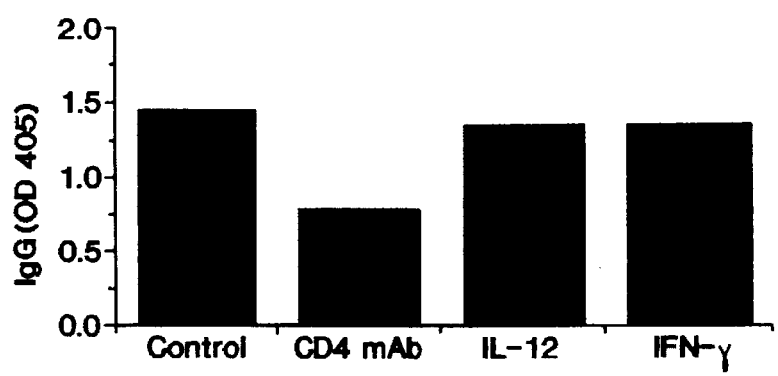
FIG. 13B is a graph summarizing the relative amounts ($OD_{405}$) of IgG present in BAL samples. The symbols are as described in FIG. 13A.
Figure 13C:
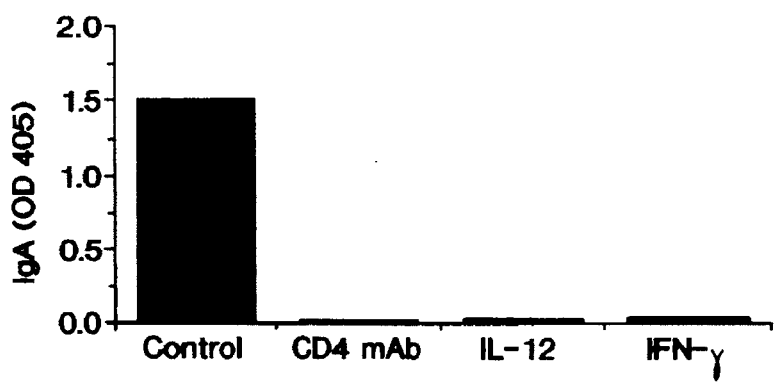
FIG. 13C is a graph summarizing the relative amounts ($OD_{405}$) of IgA present in BAL samples. The symbols are as described in FIG. 13A.

The results are shown graphically in FIGS. 13A through 13C, which summarize neutralizing antibody titer, and the relative amounts ($OD_{405}$) of IgG and IgA present in BAL samples. The titer of neutralizing antibody for each sample was reported as the highest dilution with which less than 50% of cells stained blue.

As demonstrated in the first bar of FIGS. 13A through 13C, the cytokines identified in Table 1 above were associated in the control mice with the appearance of antibodies to adenovirus proteins in BAL of both the IgG and IgA isotypes that were capable of neutralizing the human Ad5 recombinant vector in an in vitro assay out to a 1:800 dilution.

As shown in the second bar of the graphs of FIGS. 13A through 13C, transient CD4⁺ cell depletion inhibited the formation of neutralizing antibody (FIG. 13A) and virus specific IgA antibody (FIG. 13C) by 80-fold, thereby allowing efficient gene transfer to occur following a second administration of virus (see FIG. 12F). FIG. 13B shows a slight inhibition of IgG as well.

More importantly, as shown in the third bar of the three graphs, IL-12 selectively blocked secretion of antigen specific IgA (FIG. 13C), without significantly impacting on formation of IgG (FIG. 13B). This was concurrent with a 32-fold reduction in neutralizing antibody (FIG. 13A).

The gamma-interferon treated animals (fourth bar of FIGS. 13A through 13B) were virtually indistinguishable from the animals treated with IL-12 in that virus specific IgA (FIG. 13C) and neutralizing antibody (FIG. 13A) were decreased as compared to the control animals not treated with cytokine, but not to the extent obtained with those treated with IL-12.

These studies demonstrate that inhibition of CD4⁺ function at the time of primary exposure to virus is sufficient to prevent the formation of blocking antibodies. The concordant reduction of neutralizing antibody with antiviral IgA suggests that immunoglobulin of the IgA subtype is primarily responsible for the blockade to gene transfer.

All references recited above are incorporated herein by reference. Numerous modifications and variations of the present invention are included in the above-identified specification and are expected to be obvious to one of skill in the art. Such modifications and alterations to the compositions and processes of the present invention, such as selections of different modifications of adenovirus vectors selected to carry the VLDLR gene, or selection or dosage of the vectors or immune modulators are believed to be within the scope of the claims appended hereto.

---

What is claimed is:

1. A recombinant adenoviral vector comprising a human VLDL receptor gene operatively linked to regulatory sequences directing expression of said receptor gene in a hepatocyte.

2. The vector according to claim 1 further comprising adenovirus 5' and 3' cis-elements necessary for replication and virion encapsidation.

3. The vector according to claim 1 further comprising a deletion in all or a portion of the E1 gene.

4. The vector according to claim 1 further comprising a deletion in all or a portion of the E3 gene.

5. A method for delivering a VLDL receptor gene into a hepatocyte comprising introducing into said hepatocyte an effective amount of a recombinant adenoviral vector comprising a human VLDL receptor gene operatively linked to regulatory sequences directing expression of the VLDL receptor in said hepatocyte.

6. A mammalian hepatocyte, which expresses a human VLDL receptor introduced therein through transduction of said hepatocyte by an adenoviral vector comprising a human VLDL receptor gene operatively linked to regulatory sequences directing expression of said receptor gene in said hepatocyte.

7. A method for treating a patient having a disorder characterized by an elevated concentration of LDL in plasma comprising administering into the bloodstream of said patient an effective amount of a recombinant adenoviral vector comprising: a human VLDL receptor gene operatively linked to regulatory sequences directing expression of the VLDL receptor in hepatocytes.

8. The method according to claim 7 wherein said disorder is familial hypercholesterolemia or familial combined hyperlipidemia.

9. A method for decreasing the levels of VLDL and LDL in the plasma of a patient, comprising administering into the bloodstream of said patient an effective amount of an adenoviral vector comprising a human VLDL receptor gene operatively linked to regulatory sequences directing expression of the VLDL receptor in hepatocytes.

10. A pharmaceutical composition comprising a pharmaceutically acceptable carrier and an adenoviral vector, said vector comprising a human VLDL receptor gene operatively linked to regulatory sequences directing expression of said receptor gene in a hepatocyte.

11. The composition according to claim 10 wherein said adenoviral vector comprises adenovirus 5' and 3' cis-elements necessary for replication and virion encapsidation.

12. The composition according to claim 10 wherein said adenoviral vector comprises a deletion in all or a portion of the E1 gene.

13. The composition according to claim 10 wherein said adenoviral vector comprises a deletion in all or a portion of the E3 gene.

* * * * *

UNITED STATES PATENT AND TRADEMARK OFFICE
CERTIFICATE OF CORRECTION

PATENT NO. : 5,652,224
DATED : July 29, 1997
INVENTOR(S) : James M. Wilson, Karen Kozarsky, and Jerome Strauss, III It is certified that error appears in the above-indentified patent and that said Letters Patent is hereby corrected as shown below:

Col. 5, line 7, delete "section" and insert in place thereof -- sections --.

Col. 5, line 8, delete "is".

Col. 5, line 12, delete "21" and insert in place thereof -- 10 --.

Col. 5, line 13, insert the following paragraph

Figure 10A:
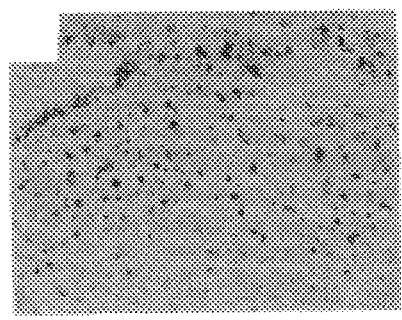
FIG. 10A is an X-gal histochemical stain of liver sections of LDL knock-out mice injected with phosphate buffered saline on day 0 and sacrificed on day 3. See, Example 6.
Figure 10E:
FIG. 10E is an X-gal histochemical stain of liver sections Of LDL knock-out mice injected with H5.010CMVVLDLR on day 0 and sacrificed on day 3.
Figure 10B:
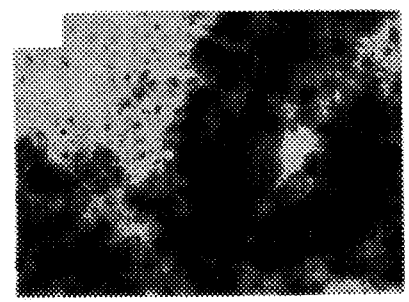
FIG. 10B is an X-gal histochemical stain of liver section is of LDL knock-out mice injected with H5.010CMVlacZ on day 0 and sacrificed on day 3.
Figure 10F:
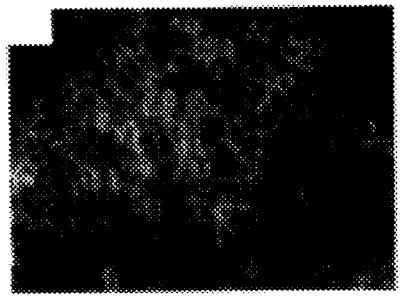
FIG. 10F is an X-gal histochemical stain of liver sections of LDL knock-out mice injected with H5.010CBhLDLR on day 0 and sacrificed on day 3.
Figure 10C:
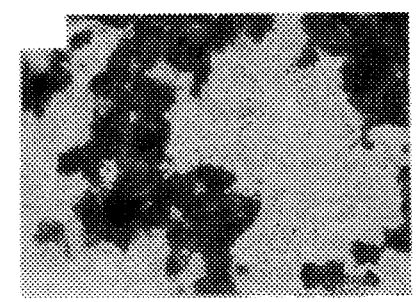
FIG. 10C is an X-gal histochemical stain of liver sections of LDL knock-out mice injected with H5.010CMVlacZ on day 0 and sacrificed on day 21.
Figure 10G:
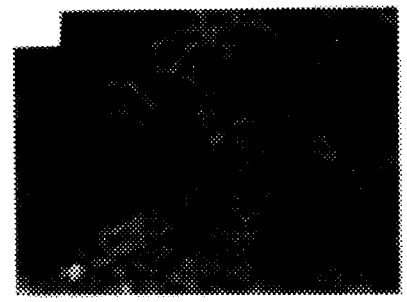
FIG. 10G is an X-gal histochemical stain of liver sections of LDL knock-out mice injected with H5.010CBhLDLR on day 0 and sacrificed on day 10.
Figure 10D:
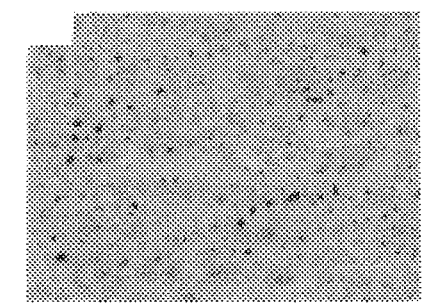
FIG. 10H is an X-gal histochemical stain of liver sections of LDL knock-out mice injected with H5.010CBhLDLR on day 0 and sacrificed on day 21.
FIG. 10I is an X-gal histochemical stain of liver sections of LDL knock-out mice injected with H5.010CBhLDLR on day 0 and sacrificed on day 3.
FIG. 10J is an X-gal histochemical stain of liver sections of LDL knock-out mice injected with H5.010CMVVLDLR on day 0 and sacrificed on day 3.
FIG. 10K is an X-gal histochemical stain of liver sections of LDL knock-out mice injected with H5.010CMVVLDLR on day 0 and sacrificed on day 10.
FIG. 10L is an X-gal histochemical stain of liver sections of LDL knock-out mice injected with H5.010CMVVLDLR on day 0 and sacrificed on day 21.
Figure 10H:
Figure 10I:
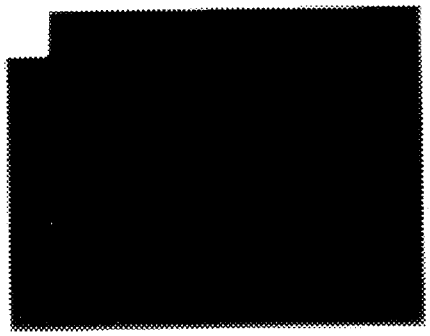
Figure 10J:
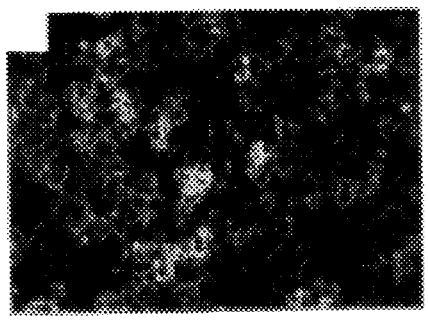
Figure 10K:
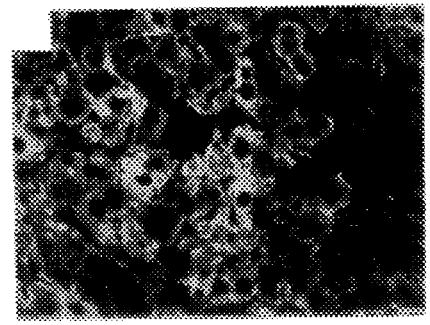
Figure 10L:
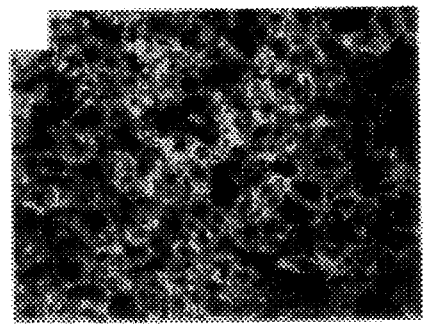

-- FIG. 10D is an X-gal histochemical stain of liver sections of *LDL* knock-out mice injected with H5.010CMV*lacZ* on day 0 and sacrificed on day 21. --

Signed and Sealed this

Twenty-first Day of October 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,652,224
DATED : July 29, 1997
INVENTOR(S) : Wilson et al.

It is certified that error appears in the above-identified patent and that said Letters Patent is hereby corrected as shown below:

```
At column 4, line 48, after "post-infusion for" insert --LDL
    receptor knock-out--;
At column 4, line 52, after "post-infusion for" insert --LDL
    receptor knock-out--;
At column 4, line 56, after "post-infusion for" insert --LDL
    receptor knock-out--;
At column 5, line 5, delete "LDL" replace with --LDLr--;
At column 5, line 8, delete "LDL" replace with --LDLr--;
At column 5, line 11, delete "LDL" replace with --LDLr--;
At column 5, line 14, delete "LDL" replace with --LDLr--;
At column 5, line 17, delete "LDL" replace with --LDLr--;
At column 5, line 20, delete "LDL" replace with --LDLr--;
At column 5, line 23, delete "LDL" replace with --LDLr--;
At column 5, line 26, delete "LDL" replace with --LDLr--;
At column 5, line 29, delete "LDL" replace with --LDLr--;
At column 5, line 32, delete "LDL" replace with --LDLr--;
At column 5, line 35, delete "LDL" replace with --LDLr--.
```

Signed and Sealed this

Thirteenth Day of January, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3656 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 392..3010

( x i ) SEQUENCE DESCRIPTION: SEQ ID NO:1:

-continued

```
CTCTGCGGGC CGCGGGTGCG GGTCGTCGCT ACCGGCTCTC TCCGTTCTGT GCTCTCTTCT      60

GCTCTCGGCT CCCCACCCCC TCTCCCTTCC CTCCTCTCCC CTTGCCTCCC CTCCTCTGCA     120

GCGCCTGCAT TATTTTCTGC CCGCAGCTCG GCTTGCACTG CTGCTGCAGC CCGGGGAGGT     180

GGCTGGGTGG GTGGGGAGGA GACTGTGCAA GTTGTAGGGG AGGGGTGCC CTCTTCTTCC      240

CCGCTCCCTT CCCCAGCCAA GTGGTTCCCC TCCTTCTCCC CCTTTCCCCT CCCAGCCCCC     300

ACCTTCTTCC TCTTTCGGAA GGGCTGGTAA CTTGTCGTGC GGAGCGAACG GCGGCGGCGG     360

CGGCGGCGGC GGCACCATCC AGGCGGGCAC C ATG GGC ACG TCC GCG CTC TGG        412
                                   Met Gly Thr Ser Ala Leu Trp
                                     1               5
```

| | | | | | | | | | | | | | | | | |
|---|---|---|---|---|---|---|---|---|---|---|---|---|---|---|---|---|
| GCC | GTC | TGG | CTG | CTG | CTC | GCG | CTG | TGC | TGG | GCG | CCC | CGG | GAG | AGC | GGC | 460 |
| Ala | Val | Trp | Leu | Leu | Leu | Ala | Leu | Cys | Trp | Ala | Pro | Arg | Glu | Ser | Gly | |
| | | 10 | | | | | 15 | | | | | 20 | | | | |

| GCC | ACC | GGA | ACC | GGG | AGA | AAA | GCC | AAA | TGT | GAA | CCC | TCC | CAA | TTC | CAG | 508 |
| Ala | Thr | Gly | Thr | Gly | Arg | Lys | Ala | Lys | Cys | Glu | Pro | Ser | Gln | Phe | Gln | |
| | 25 | | | | | 30 | | | | | 35 | | | | | |

| TGC | ACA | AAT | GGT | CGC | TGT | ATT | ACG | CTG | TTG | TGG | AAA | TGT | GAT | GGG | GAT | 556 |
| Cys | Thr | Asn | Gly | Arg | Cys | Ile | Thr | Leu | Leu | Trp | Lys | Cys | Asp | Gly | Asp | |
| 40 | | | | | 45 | | | | | 50 | | | | | 55 | |

| GAA | GAC | TGT | GTT | GAC | GGC | AGT | GAT | GAA | AAG | AAC | TGT | GTA | AAG | AAG | ACG | 604 |
| Glu | Asp | Cys | Val | Asp | Gly | Ser | Asp | Glu | Lys | Asn | Cys | Val | Lys | Lys | Thr | |
| | | | 60 | | | | | 65 | | | | | 70 | | | |

| TGT | GCT | GAA | TCT | GAC | TTC | GTG | TGC | AAC | AAT | GGC | CAG | TGT | GTT | CCC | AGC | 652 |
| Cys | Ala | Glu | Ser | Asp | Phe | Val | Cys | Asn | Asn | Gly | Gln | Cys | Val | Pro | Ser | |
| | | | 75 | | | | | 80 | | | | | 85 | | | |

| CGA | TGG | AAG | TGT | GAT | GGA | GAT | CCT | GAC | TGC | GAA | GAT | GGT | TCA | GAT | GAA | 700 |
| Arg | Trp | Lys | Cys | Asp | Gly | Asp | Pro | Asp | Cys | Glu | Asp | Gly | Ser | Asp | Glu | |
| | | 90 | | | | | 95 | | | | | 100 | | | | |

| AGC | CCA | GAA | CAG | TGC | CAT | ATG | AGA | ACA | TGC | CGC | ATA | CAT | GAA | ATC | AGC | 748 |
| Ser | Pro | Glu | Gln | Cys | His | Met | Arg | Thr | Cys | Arg | Ile | His | Glu | Ile | Ser | |
| | 105 | | | | | 110 | | | | | 115 | | | | | |

| TGT | GGC | GCC | CAT | TCT | ACT | CAG | TGT | ATC | CCA | GTG | TCC | TGG | AGA | TGT | GAT | 796 |
| Cys | Gly | Ala | His | Ser | Thr | Gln | Cys | Ile | Pro | Val | Ser | Trp | Arg | Cys | Asp | |
| 120 | | | | | 125 | | | | | 130 | | | | | 135 | |

| GGT | GAA | AAT | GAT | TGT | GAC | AGT | GGA | GAA | GAT | GAA | GAA | AAC | TGT | GGC | AAT | 844 |
| Gly | Glu | Asn | Asp | Cys | Asp | Ser | Gly | Glu | Asp | Glu | Glu | Asn | Cys | Gly | Asn | |
| | | | 140 | | | | | 145 | | | | | 150 | | | |

| ATA | ACA | TGT | AGT | CCC | GAC | GAG | TTC | ACC | TGC | TCC | AGT | GGC | CGC | TGC | ATC | 892 |
| Ile | Thr | Cys | Ser | Pro | Asp | Glu | Phe | Thr | Cys | Ser | Ser | Gly | Arg | Cys | Ile | |
| | | | 155 | | | | | 160 | | | | | 165 | | | |

| TCC | AGG | AAC | TTT | GTA | TGC | AAT | GGC | CAG | GAT | GAC | TGC | AGC | GAT | GGC | AGT | 940 |
| Ser | Arg | Asn | Phe | Val | Cys | Asn | Gly | Gln | Asp | Asp | Cys | Ser | Asp | Gly | Ser | |
| | | 170 | | | | | 175 | | | | | 180 | | | | |

| GAT | GAG | CTG | GAC | TGT | GCC | CCG | CCA | ACC | TGT | GGC | GCC | CAT | GAG | TTC | CAG | 988 |
| Asp | Glu | Leu | Asp | Cys | Ala | Pro | Pro | Thr | Cys | Gly | Ala | His | Glu | Phe | Gln | |
| | 185 | | | | | 190 | | | | | 195 | | | | | |

| TGC | AGC | ACC | TCC | TCC | TGC | ATC | CCC | ATC | AGC | TGG | GTA | TGC | GAC | GAT | GAT | 1036 |
| Cys | Ser | Thr | Ser | Ser | Cys | Ile | Pro | Ile | Ser | Trp | Val | Cys | Asp | Asp | Asp | |
| 200 | | | | | 205 | | | | | 210 | | | | | 215 | |

| GCA | GAC | TGC | TCC | GAC | CAA | TCT | GAT | GAG | TCC | CTG | GAG | CAG | TGT | GGC | CGT | 1084 |
| Ala | Asp | Cys | Ser | Asp | Gln | Ser | Asp | Glu | Ser | Leu | Glu | Gln | Cys | Gly | Arg | |
| | | | 220 | | | | | 225 | | | | | 230 | | | |

| CAG | CCA | GTC | ATA | CAC | ACC | AAG | TGT | CCA | GCC | AGC | GAA | ATC | CAG | TGC | GGC | 1132 |
| Gln | Pro | Val | Ile | His | Thr | Lys | Cys | Pro | Ala | Ser | Glu | Ile | Gln | Cys | Gly | |
| | | | 235 | | | | | 240 | | | | | 245 | | | |

| | | | | | | | | | | | | | | | | |
|---|---|---|---|---|---|---|---|---|---|---|---|---|---|---|---|---|
| TCT | GGC | GAG | TGC | ATC | CAT | AAG | AAG | TGG | CGA | TGT | GAT | GGG | GAC | CCT | GAC | 1180 |
| Ser | Gly | Glu | Cys | Ile | His | Lys | Lys | Trp | Arg | Cys | Asp | Gly | Asp | Pro | Asp | |
| | | 250 | | | | 255 | | | | | 260 | | | | | |
| TGC | AAG | GAT | GGC | AGT | GAT | GAG | GTC | AAC | TGT | CCC | TCT | CGA | ACT | TGC | CGA | 1228 |
| Cys | Lys | Asp | Gly | Ser | Asp | Glu | Val | Asn | Cys | Pro | Ser | Arg | Thr | Cys | Arg | |
| | 265 | | | | 270 | | | | | 275 | | | | | | |
| CCT | GAC | CAA | TTT | GAA | TGT | GAG | GAT | GGC | AGC | TGC | ATC | CAT | GGC | AGC | AGG | 1276 |
| Pro | Asp | Gln | Phe | Glu | Cys | Glu | Asp | Gly | Ser | Cys | Ile | His | Gly | Ser | Arg | |
| 280 | | | | | 285 | | | | | 290 | | | | | 295 | |
| CAG | TGT | AAT | GGT | ATC | CGA | GAC | TGT | GTC | GAT | GGT | TCC | GAT | GAA | GTC | AAC | 1324 |
| Gln | Cys | Asn | Gly | Ile | Arg | Asp | Cys | Val | Asp | Gly | Ser | Asp | Glu | Val | Asn | |
| | | | | 300 | | | | 305 | | | | | 310 | | | |
| TGC | AAA | AAT | GTC | AAT | CAG | TGC | TTG | GGC | CCT | GGA | AAA | TTC | AAG | TGC | AGA | 1372 |
| Cys | Lys | Asn | Val | Asn | Gln | Cys | Leu | Gly | Pro | Gly | Lys | Phe | Lys | Cys | Arg | |
| | | | 315 | | | | 320 | | | | | 325 | | | | |
| AGT | GGA | GAA | TGC | ATA | GAT | ATC | AGC | AAA | GTA | TGT | AAC | CAG | GAG | CAG | GAC | 1420 |
| Ser | Gly | Glu | Cys | Ile | Asp | Ile | Ser | Lys | Val | Cys | Asn | Gln | Glu | Gln | Asp | |
| | | 330 | | | | 335 | | | | | 340 | | | | | |
| TGC | AGG | GAC | TGG | AGT | GAT | GAG | CCC | CTG | AAA | GAG | TGT | CAT | ATA | AAC | GAA | 1468 |
| Cys | Arg | Asp | Trp | Ser | Asp | Glu | Pro | Leu | Lys | Glu | Cys | His | Ile | Asn | Glu | |
| | 345 | | | | 350 | | | | | 355 | | | | | | |
| TGC | TTG | GTA | AAT | AAT | GGT | GGA | TGT | TCT | CAT | ATC | TGC | AAA | GAC | CTA | GTT | 1516 |
| Cys | Leu | Val | Asn | Asn | Gly | Gly | Cys | Ser | His | Ile | Cys | Lys | Asp | Leu | Val | |
| 360 | | | | | 365 | | | | | 370 | | | | | 375 | |
| ATA | GGC | TAC | GAG | TGT | GAC | TGT | GCA | GCT | GGG | TTT | GAA | CTG | ATA | GAT | AGG | 1564 |
| Ile | Gly | Tyr | Glu | Cys | Asp | Cys | Ala | Ala | Gly | Phe | Glu | Leu | Ile | Asp | Arg | |
| | | | | 380 | | | | 385 | | | | | 390 | | | |
| AAA | ACC | TGT | GGA | GAT | ATT | GAT | GAA | TGC | CAA | AAT | CCA | GGA | ATC | TGC | AGT | 1612 |
| Lys | Thr | Cys | Gly | Asp | Ile | Asp | Glu | Cys | Gln | Asn | Pro | Gly | Ile | Cys | Ser | |
| | | | 395 | | | | 400 | | | | | 405 | | | | |
| CAA | ATT | TGT | ATC | AAC | TTA | AAA | GGC | GGT | TAC | AAG | TGT | GAA | TGT | AGT | CGT | 1660 |
| Gln | Ile | Cys | Ile | Asn | Leu | Lys | Gly | Gly | Tyr | Lys | Cys | Glu | Cys | Ser | Arg | |
| | | 410 | | | | 415 | | | | | 420 | | | | | |
| GCC | TAT | CAA | ATG | GAT | CTT | GCT | ACT | GGC | GTG | TGC | AAG | GCA | GTA | GGC | AAA | 1708 |
| Ala | Tyr | Gln | Met | Asp | Leu | Ala | Thr | Gly | Val | Cys | Lys | Ala | Val | Gly | Lys | |
| | | 425 | | | | 430 | | | | | 435 | | | | | |
| GAG | CCA | AGT | CTG | ATC | TTC | ACT | AAT | CGA | AGA | GAC | ATC | AGG | AAG | ATT | GGC | 1756 |
| Glu | Pro | Ser | Leu | Ile | Phe | Thr | Asn | Arg | Arg | Asp | Ile | Arg | Lys | Ile | Gly | |
| 440 | | | | | 445 | | | | | 450 | | | | | 455 | |
| TTA | GAG | AGG | AAA | GAA | TAT | ATC | CAA | CTA | GTT | GAA | CAG | CTA | AGA | AAC | ACT | 1804 |
| Leu | Glu | Arg | Lys | Glu | Tyr | Ile | Gln | Leu | Val | Glu | Gln | Leu | Arg | Asn | Thr | |
| | | | | 460 | | | | | 465 | | | | | 470 | | |
| GTG | GCT | CTC | GAT | GCT | GAC | ATT | GCT | GCC | CAG | AAA | CTA | TTC | TGG | GCC | GAT | 1852 |
| Val | Ala | Leu | Asp | Ala | Asp | Ile | Ala | Ala | Gln | Lys | Leu | Phe | Trp | Ala | Asp | |
| | | | 475 | | | | 480 | | | | | 485 | | | | |
| CTA | AGC | CAA | AAG | GCT | ATC | TTC | AGT | GCC | TCA | ATT | GAT | GAC | AAG | GTT | GGT | 1900 |
| Leu | Ser | Gln | Lys | Ala | Ile | Phe | Ser | Ala | Ser | Ile | Asp | Asp | Lys | Val | Gly | |
| | | 490 | | | | 495 | | | | | 500 | | | | | |
| AGA | CAT | GTT | AAA | ATG | ATC | GAC | AAT | GTC | TAT | AAT | CCT | GCA | GCC | ATT | GCT | 1948 |
| Arg | His | Val | Lys | Met | Ile | Asp | Asn | Val | Tyr | Asn | Pro | Ala | Ala | Ile | Ala | |
| | 505 | | | | 510 | | | | | 515 | | | | | | |
| GTT | GAT | TGG | GTG | TAC | AAG | ACC | ATC | TAC | TGG | ACT | GAT | GCG | GCT | TCT | AAG | 1996 |
| Val | Asp | Trp | Val | Tyr | Lys | Thr | Ile | Tyr | Trp | Thr | Asp | Ala | Ala | Ser | Lys | |
| 520 | | | | | 525 | | | | | 530 | | | | | 535 | |
| ACT | ATT | TCA | GTA | GCT | ACC | CTA | GAT | GGA | ACC | AAG | AGG | AAG | TTC | CTG | TTT | 2044 |
| Thr | Ile | Ser | Val | Ala | Thr | Leu | Asp | Gly | Thr | Lys | Arg | Lys | Phe | Leu | Phe | |
| | | | | 540 | | | | | 545 | | | | | 550 | | |
| AAC | TCT | GAC | TTG | CGA | GAG | CCT | GCC | TCC | ATA | GCT | GTG | GAC | CCA | CTG | TCT | 2092 |
| Asn | Ser | Asp | Leu | Arg | Glu | Pro | Ala | Ser | Ile | Ala | Val | Asp | Pro | Leu | Ser | |
| | | | 555 | | | | 560 | | | | | 565 | | | | |

```
GGC TTT GTT TAC TGG TCA GAC TGG GGT GAA CCA GCT AAA ATA GAA AAA                    2140
Gly Phe Val Tyr Trp Ser Asp Trp Gly Glu Pro Ala Lys Ile Glu Lys
        570             575             580

GCA GGA ATG AAT GGA TTC GAT AGA CGT CCA CTG GTG ACA GCG GAT ATC                    2188
Ala Gly Met Asn Gly Phe Asp Arg Arg Pro Leu Val Thr Ala Asp Ile
        585             590             595

CAG TGG CCT AAC GGA ATT ACA CTT GAC CTT ATA AAA AGT CGC CTC TAT                    2236
Gln Trp Pro Asn Gly Ile Thr Leu Asp Leu Ile Lys Ser Arg Leu Tyr
600             605             610             615

TGG CTT GAT TCT AAG TTG CAC ATG TTA TCC AGC GTG GAC TTG AAT GGC                    2284
Trp Leu Asp Ser Lys Leu His Met Leu Ser Ser Val Asp Leu Asn Gly
                620             625             630

CAA GAT CGT AGG ATA GTA CTA AAG TCT CTG GAG TTC CTA GCT CAT CCT                    2332
Gln Asp Arg Arg Ile Val Leu Lys Ser Leu Glu Phe Leu Ala His Pro
            635             640             645

CTT GCA CTA ACA ATA TTT GAG GAT CGT GTC TAC TGG ATA GAT GGG GAA                    2380
Leu Ala Leu Thr Ile Phe Glu Asp Arg Val Tyr Trp Ile Asp Gly Glu
        650             655             660

AAT GAA GCA GTC TAT GGT GCC AAT AAA TTC ACT GGA TCA GAG CAT GCC                    2428
Asn Glu Ala Val Tyr Gly Ala Asn Lys Phe Thr Gly Ser Glu His Ala
        665             670             675

ACT CTA GTC AAC AAC CTG AAT GAT GCC CAA GAC ATC ATT GTC TAT CAT                    2476
Thr Leu Val Asn Asn Leu Asn Asp Ala Gln Asp Ile Ile Val Tyr His
680             685             690             695

GAA CTT GTA CAG CCA TCA GGT AAA AAT TGG TGT GAA GAA GAC ATG GAG                    2524
Glu Leu Val Gln Pro Ser Gly Lys Asn Trp Cys Glu Glu Asp Met Glu
                700             705             710

AAT GGA GGA TGT GAA TAC CTA TGC CTG CCA GCA CCA CAG ATT AAT GAT                    2572
Asn Gly Gly Cys Glu Tyr Leu Cys Leu Pro Ala Pro Gln Ile Asn Asp
            715             720             725

CAC TCT CCA AAA TAT ACC TGT TCC TGT CCC AGT GGG TAC AAT GTA GAG                    2620
His Ser Pro Lys Tyr Thr Cys Ser Cys Pro Ser Gly Tyr Asn Val Glu
        730             735             740

GAA AAT GGC CGA GAC TGT CAA AGT ACT GCA ACT ACT GTG ACT TAC AGT                    2668
Glu Asn Gly Arg Asp Cys Gln Ser Thr Ala Thr Thr Val Thr Tyr Ser
        745             750             755

GAG ACA AAA GAT ACG AAC ACA ACA GAA ATT TCA GCA ACT AGT GGA CTA                    2716
Glu Thr Lys Asp Thr Asn Thr Thr Glu Ile Ser Ala Thr Ser Gly Leu
760             765             770             775

GTT CCT GGA GGG ATC AAT GTG ACC ACA GCA GTA TCA GAG GTC AGT GTT                    2764
Val Pro Gly Gly Ile Asn Val Thr Thr Ala Val Ser Glu Val Ser Val
                780             785             790

CCC CCA AAA GGG ACT TCT GCC GCA TGG GCC ATT CTT CCT CTC TTG CTC                    2812
Pro Pro Lys Gly Thr Ser Ala Ala Trp Ala Ile Leu Pro Leu Leu Leu
            795             800             805

TTA GTG ATG GCA GCA GTA GGT GGC TAC TTG ATG TGG CGG AAT TGG CAA                    2860
Leu Val Met Ala Ala Val Gly Gly Tyr Leu Met Trp Arg Asn Trp Gln
        810             815             820

CAC AAG AAC ATG AAA AGC ATG AAC TTT GAC AAT CCT GTG TAC TTG AAA                    2908
His Lys Asn Met Lys Ser Met Asn Phe Asp Asn Pro Val Tyr Leu Lys
825             830             835

ACC ACT GAA GAG GAC CTC TCC ATA GAC ATT GGT AGA CAC AGT GCT TCT                    2956
Thr Thr Glu Glu Asp Leu Ser Ile Asp Ile Gly Arg His Ser Ala Ser
840             845             850             855

GTT GGA CAC ACG TAC CCA GCA ATA TCA GTT GTA AGC ACA GAT GAT GAT                    3004
Val Gly His Thr Tyr Pro Ala Ile Ser Val Val Ser Thr Asp Asp Asp
                860             865             870

CTA GCT TGACTTCTGT GACAAATGTT GACCTTTGAG GTCTAAACAA ATAATACCCC                     3060
Leu Ala
CGTCGGAATG GTAACCGAGC CAGCAGCTGA AGTCTCTTTT TCTTCCTCTC GGCTGGAAGA                  3120
```

-continued

| ACATCAAGAT | ACCTTTGCGT | GGATCAAGCT | TGCTGTACTT | GACCGTTTTT | ATATTACTTT | 3180 |
| TGTAAATATT | CTTGTCCACA | TTCTACTTCA | GCTTTGGATG | TGGTTACCGA | GTATCTGTAA | 3240 |
| CCCTTGAATT | TCTAGACAGT | ATTGCCACCT | CTGGCCAAAT | ATGCACTTTC | CCTAGAAAGC | 3300 |
| CATATTCCAG | CAGTGAAACT | TGTGCTATAG | TGTATACCAC | CTGTACATAC | ATTGTATAGG | 3360 |
| CCATCTGTAA | ATATCCCAGA | GAACAATCAC | TATTCTTAAG | CACTTTGAAA | ATATTTCTAT | 3420 |
| GTAAATTATT | GTAAACTTTT | TCAATGGTTG | GGACAATGGC | AATAGGACAA | AACGGGTTAC | 3480 |
| TAAGATGAAA | TTGCCAAAAA | AATTTATAAA | CTAATTTTGG | TACGTATGAA | TGATATCTTT | 3540 |
| GACCTCAATG | GAGGTTTGCA | AAGACTGAGT | GTTCAAACTA | CTGTACATTT | TTTTTCAAGT | 3600 |
| GCTAAAAAAT | TAAACCAAGC | AGCTTAAAAA | AAAAAAAAAA | AAAAAAAAAA | AAAAAA | 3656 |

( 2 ) INFORMATION FOR SEQ ID NO:2:

( i ) SEQUENCE CHARACTERISTICS:
        ( A ) LENGTH: 873 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Thr Ser Ala Leu Trp Ala Val Trp Leu Leu Leu Ala Leu Cys
 1               5                  10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
            35                  40                  45

Leu Trp Lys Cys Asp Gly Asp Glu Asp Cys Val Asp Gly Ser Asp Glu
        50                  55                  60

Lys Asn Cys Val Lys Lys Thr Cys Ala Glu Ser Asp Phe Val Cys Asn
 65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys His Met Arg Thr
            100                 105                 110

Cys Arg Ile His Glu Ile Ser Cys Gly Ala His Ser Thr Gln Cys Ile
        115                 120                 125

Pro Val Ser Trp Arg Cys Asp Gly Glu Asn Asp Cys Asp Ser Gly Glu
    130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
            180                 185                 190

Cys Gly Ala His Glu Phe Gln Cys Ser Thr Ser Ser Cys Ile Pro Ile
        195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Ala Ser Glu Ile Gln Cys Gly Ser Gly Glu Cys Ile His Lys Lys Trp
                245                 250                 255

Arg Cys Asp Gly Asp Pro Asp Cys Lys Asp Gly Ser Asp Glu Val Asn
            260                 265                 270
```

```
Cys Pro Ser Arg Thr Cys Arg Pro Asp Gln Phe Glu Cys Glu Asp Gly
        275                 280                 285
Ser Cys Ile His Gly Ser Arg Gln Cys Asn Gly Ile Arg Asp Cys Val
    290                 295                 300
Asp Gly Ser Asp Glu Val Asn Cys Lys Asn Val Asn Gln Cys Leu Gly
305                 310                 315                 320
Pro Gly Lys Phe Lys Cys Arg Ser Gly Glu Cys Ile Asp Ile Ser Lys
                325                 330                 335
Val Cys Asn Gln Glu Gln Asp Cys Arg Asp Trp Ser Asp Glu Pro Leu
            340                 345                 350
Lys Glu Cys His Ile Asn Glu Cys Leu Val Asn Asn Gly Gly Cys Ser
        355                 360                 365
His Ile Cys Lys Asp Leu Val Ile Gly Tyr Glu Cys Asp Cys Ala Ala
    370                 375                 380
Gly Phe Glu Leu Ile Asp Arg Lys Thr Cys Gly Asp Ile Asp Glu Cys
385                 390                 395                 400
Gln Asn Pro Gly Ile Cys Ser Gln Ile Cys Ile Asn Leu Lys Gly Gly
                405                 410                 415
Tyr Lys Cys Glu Cys Ser Arg Ala Tyr Gln Met Asp Leu Ala Thr Gly
            420                 425                 430
Val Cys Lys Ala Val Gly Lys Glu Pro Ser Leu Ile Phe Thr Asn Arg
        435                 440                 445
Arg Asp Ile Arg Lys Ile Gly Leu Glu Arg Lys Glu Tyr Ile Gln Leu
    450                 455                 460
Val Glu Gln Leu Arg Asn Thr Val Ala Leu Asp Ala Asp Ile Ala Ala
465                 470                 475                 480
Gln Lys Leu Phe Trp Ala Asp Leu Ser Gln Lys Ala Ile Phe Ser Ala
                485                 490                 495
Ser Ile Asp Asp Lys Val Gly Arg His Val Lys Met Ile Asp Asn Val
            500                 505                 510
Tyr Asn Pro Ala Ala Ile Ala Val Asp Trp Val Tyr Lys Thr Ile Tyr
        515                 520                 525
Trp Thr Asp Ala Ala Ser Lys Thr Ile Ser Val Ala Thr Leu Asp Gly
    530                 535                 540
Thr Lys Arg Lys Phe Leu Phe Asn Ser Asp Leu Arg Glu Pro Ala Ser
545                 550                 555                 560
Ile Ala Val Asp Pro Leu Ser Gly Phe Val Tyr Trp Ser Asp Trp Gly
                565                 570                 575
Glu Pro Ala Lys Ile Glu Lys Ala Gly Met Asn Gly Phe Asp Arg Arg
            580                 585                 590
Pro Leu Val Thr Ala Asp Ile Gln Trp Pro Asn Gly Ile Thr Leu Asp
        595                 600                 605
Leu Ile Lys Ser Arg Leu Tyr Trp Leu Asp Ser Lys Leu His Met Leu
    610                 615                 620
Ser Ser Val Asp Leu Asn Gly Gln Asp Arg Arg Ile Val Leu Lys Ser
625                 630                 635                 640
Leu Glu Phe Leu Ala His Pro Leu Ala Leu Thr Ile Phe Glu Asp Arg
                645                 650                 655
Val Tyr Trp Ile Asp Gly Glu Asn Glu Ala Val Tyr Gly Ala Asn Lys
            660                 665                 670
Phe Thr Gly Ser Glu His Ala Thr Leu Val Asn Asn Leu Asn Asp Ala
        675                 680                 685
```

-continued

```
Gln  Asp  Ile  Ile  Val  Tyr  His  Glu  Leu  Val  Gln  Pro  Ser  Gly  Lys  Asn
     690                      695                     700

Trp  Cys  Glu  Glu  Asp  Met  Glu  Asn  Gly  Gly  Cys  Glu  Tyr  Leu  Cys  Leu
705                      710                     715                     720

Pro  Ala  Pro  Gln  Ile  Asn  Asp  His  Ser  Pro  Lys  Tyr  Thr  Cys  Ser  Cys
                    725                     730                     735

Pro  Ser  Gly  Tyr  Asn  Val  Glu  Glu  Asn  Gly  Arg  Asp  Cys  Gln  Ser  Thr
                    740                     745                     750

Ala  Thr  Thr  Val  Thr  Tyr  Ser  Glu  Thr  Lys  Asp  Thr  Asn  Thr  Thr  Glu
          755                     760                     765

Ile  Ser  Ala  Thr  Ser  Gly  Leu  Val  Pro  Gly  Gly  Ile  Asn  Val  Thr  Thr
     770                     775                     780

Ala  Val  Ser  Glu  Val  Ser  Val  Pro  Pro  Lys  Gly  Thr  Ser  Ala  Ala  Trp
785                      790                     795                     800

Ala  Ile  Leu  Pro  Leu  Leu  Leu  Leu  Val  Met  Ala  Ala  Val  Gly  Gly  Tyr
                    805                     810                     815

Leu  Met  Trp  Arg  Asn  Trp  Gln  His  Lys  Asn  Met  Lys  Ser  Met  Asn  Phe
               820                     825                     830

Asp  Asn  Pro  Val  Tyr  Leu  Lys  Thr  Thr  Glu  Glu  Asp  Leu  Ser  Ile  Asp
          835                     840                     845

Ile  Gly  Arg  His  Ser  Ala  Ser  Val  Gly  His  Thr  Tyr  Pro  Ala  Ile  Ser
     850                     855                     860

Val  Val  Ser  Thr  Asp  Asp  Asp  Leu  Ala
865                     870
```

( 2 ) INFORMATION FOR SEQ ID NO:3:

( i ) SEQUENCE CHARACTERISTICS:
( A ) LENGTH: 9592 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:3:

```
GAATTCGCTA  GCATCATCAA  TAATATACCT  TATTTTGGAT  TGAAGCCAAT  ATGATAATGA     60
GGGGGTGGAG  TTTGTGACGT  GGCGCGGGGC  GTGGGAACGG  GGCGGGTGAC  GTAGTAGTGT    120
GGCGGAAGTG  TGATGTTGCA  AGTGTGGCGG  AACACATGTA  AGCGACGGAT  GTGGCAAAAG    180
TGACGTTTTT  GGTGTGCGCC  GGTGTACACA  GGAAGTGACA  ATTTTCGCGC  GGTTTTAGGC    240
GGATGTTGTA  GTAAATTTGG  GCGTAACCGA  GTAAGATTTG  GCCATTTTCG  CGGGAAAACT    300
GAATAAGAGG  AAGTGAAATC  TGAATAATTT  TGTGTTACTC  ATAGCGCGTA  ATATTTGTCT    360
AGGGAGATCA  GCCTGCAGGT  CGTTACATAA  CTTACGGTAA  ATGGCCCGCC  TGGCTGACCG    420
CCCAACGACC  CCCGCCCATT  GACGTCAATA  ATGACGTATG  TTCCATAGT   AACGCCAATA    480
GGGACTTTCC  ATTGACGTCA  ATGGGTGGAG  TATTTACGGT  AAACTGCCCA  CTTGGCAGTA    540
CATCAAGTGT  ATCATATGCC  AAGTACGCCC  CCTATTGACG  TCAATGACGG  TAAATGGCCC    600
GCCTGGCATT  ATGCCCAGTA  CATGACCTTA  TGGGACTTTC  CTACTTGGCA  GTACATCTAC    660
GTATTAGTCA  TCGCTATTAC  CATGGTGATG  CGGTTTTGGC  AGTACATCAA  TGGGCGTGGA    720
TAGCGGTTTG  ACTCACGGGG  ATTTCCAAGT  CTCCACCCCA  TTGACGTCAA  TGGGAGTTTG    780
TTTTGGCACC  AAAATCAACG  GGACTTTCCA  AAATGTCGTA  ACAACTCCGC  CCCATTGACG    840
CAAATGGGCG  GTAGGCGTGT  ACGGTGGGAG  GTCTATATAA  GCAGAGCTCT  CTGGCTAACT    900
AGAGAACCCA  CTGCTTAACT  GGCTTATCGA  AATTAATACG  ACTCACTATA  GGGAGACCCA    960
```

-continued

```
AGCTTCTCTG CGGGCCGCGG GTGCGGGTCG TCGCTACCGG CTCTCTCCGT TCTGTGCTCT    1020
CTTCTGCTCT CGGCTCCCCA CCCCCTCTCC CTTCCCTCCT CTCCCCTTGC CTCCCCTCCT    1080
CTGCAGCGCC TGCATTATTT TCTGCCCGCA GCTCGGCTTG CACTGCTGCT GCAGCCCGGG    1140
GAGGTGGCTG GGTGGGTGGG GAGGAGACTG TGCAAGTTGT AGGGGAGGGG GTGCCCTCTT    1200
CTTCCCCGCT CCCTTCCCCA GCCAAGTGGT TCCCCTCCTT CTCCCCCTTT CCCTCCCAG    1260
CCCCCACCTT CTTCCTCTTT CGGAAGGGCT GGTAACTTGT CGTGCGGAGC GAACGGCGGC    1320
GGCGGCGGCG GCGGCGGCAC CATCCAGGCG GGCACCATGG GCACGTCCGC GCTCTGGGCC    1380
GTCTGGCTGC TGCTCGCGCT GTGCTGGGCG CCCCGGGAGA GCGGCGCCAC CGGAACCGGG    1440
AGAAAAGCCA AATGTGAACC CTCCCAATTC CAGTGCACAA ATGGTCGCTG TATTACGCTG    1500
TTGTGGAAAT GTGATGGGGA TGAAGACTGT GTTGACGGCA GTGATGAAAA GAACTGTGTA    1560
AGAAGACGT GTGCTGAATC TGACTTCGTG TGCAACAATG GCCAGTGTGT TCCCAGCCGA    1620
TGGAAGTGTG ATGGAGATCC TGACTGCGAA GATGGTTCAG ATGAAAGCCC AGAACAGTGC    1680
CATATGAGAA CATGCCGCAT ACATGAAATC AGCTGTGGCG CCCATTCTAC TCAGTGTATC    1740
CCAGTGTCCT GGAGATGTGA TGGTGAAAAT GATTGTGACA GTGGAGAAGA TGAAGAAAAC    1800
TGTGGCAATA TAACATGTAG TCCCGACGAG TTCACCTGCT CCAGTGGCCG CTGCATCTCC    1860
AGGAACTTTG TATGCAATGG CCAGGATGAC TGCAGCGATG GCAGTGATGA GCTGGACTGT    1920
GCCCCGCCAA CCTGTGGCGC CCATGAGTTC CAGTGCAGCA CCTCCTCCTG CATCCCCATC    1980
AGCTGGGTAT CGACGATGA TGCAGACTGC TCCGACCAAT CTGATGAGTC CCTGGAGCAG    2040
TGTGGCCGTC AGCCAGTCAT ACACACCAAG TGTCCAGCCA GCGAAATCCA GTGCGGCTCT    2100
GGCGAGTGCA TCCATAAGAA GTGGCGATGT GATGGGGACC CTGACTGCAA GGATGGCAGT    2160
GATGAGGTCA ACTGTCCCTC TCGAACTTGC CGACCTGACC AATTTGAATG TGAGGATGGC    2220
AGCTGCATCC ATGGCAGCAG GCAGTGTAAT GGTATCCGAG ACTGTGTCGA TGGTTCCGAT    2280
GAAGTCAACT GCAAAAATGT CAATCAGTGC TTGGGCCCTG GAAAATTCAA GTGCAGAAGT    2340
GGAGAATGCA TAGATATCAG CAAAGTATGT AACCAGGAGC AGGACTGCAG GGACTGGAGT    2400
GATGAGCCCC TGAAAGAGTG TCATATAAAC GAATGCTTGG TAAATAATGG TGGATGTTCT    2460
CATATCTGCA AAGACCTAGT TATAGGCTAC GAGTGTGACT GTGCAGCTGG GTTTGAACTG    2520
ATAGATAGGA AACCTGTGG AGATATTGAT GAATGCCAAA ATCCAGGAAT CTGCAGTCAA    2580
ATTTGTATCA ACTTAAAAGG CGGTTACAAG TGTGAATGTA GTCGTGCCTA TCAAATGGAT    2640
CTTGCTACTG GCGTGTGCAA GGCAGTAGGC AAAGAGCCAA GTCTGATCTT CACTAATCGA    2700
AGAGACATCA GGAAGATTGG CTTAGAGAGG AAAGAATATA TCCAACTAGT TGAACAGCTA    2760
AGAAACACTG TGGCTCTCGA TGCTGACATT GCTGCCCAGA AACTATTCTG GGCCGATCTA    2820
AGCCAAAAGG CTATCTTCAG TGCCTCAATT GATGACAAGG TTGGTAGACA TGTTAAAATG    2880
ATCGACAATG TCTATAATCC TGCAGCCATT GCTGTTGATT GGGTGTACAA GACCATCTAC    2940
TGGACTGATG CGGCTTCTAA GACTATTTCA GTAGCTACCC TAGATGGAAC CAAGAGGAAG    3000
TTCCTGTTTA ACTCTGACTT GCGAGAGCCT GCCTCCATAG CTGTGGACCC ACTGTCTGGC    3060
TTTGTTTACT GGTCAGACTG GGGTGAACCA GCTAAAATAG AAAAAGCAGG AATGAATGGA    3120
TTCGATAGAC GTCCACTGGT GACAGCGGAT ATCCAGTGGC CTAACGGAAT TACACTTGAC    3180
CTTATAAAAA GTCGCCTCTA TTGGCTTGAT TCTAAGTTGC ACATGTTATC CAGCGTGGAC    3240
TTGAATGGCC AAGATCGTAG GATAGTACTA AAGTCTCTGG AGTTCCTAGC TCATCCTCTT    3300
GCACTAACAA TATTTGAGGA TCGTGTCTAC TGGATAGATG GGAAAATGA AGCAGTCTAT    3360
```

```
GGTGCCAATA AATTCACTGG ATCAGAGCAT GCCACTCTAG TCAACAACCT GAATGATGCC      3420
CAAGACATCA TTGTCTATCA TGAACTTGTA CAGCCATCAG GTAAAAATTG GTGTGAAGAA      3480
GACATGGAGA ATGGAGGATG TGAATACCTA TGCCTGCCAG CACCACAGAT TAATGATCAC      3540
TCTCCAAAAT ATACCTGTTC CTGTCCCAGT GGGTACAATG TAGAGGAAAA TGGCCGAGAC      3600
TGTCAAAGTA CTGCAACTAC TGTGACTTAG AGACAAAAGA TACGAACACA ACAGAAATTT      3660
CAGCAACTAG TGGACTAGTT CCTGGAGGGA TCAATGTGAC CACAGCAGTA TCAGAGGTCA      3720
GTGTTCCCCC AAAAGGGACT TCTGCCGCAT GGGCCATTCT TCCTCTCTTG CTCTTAGTGA      3780
TGGCAGCAGT AGGTGGCTAC TTGATGTGGC GGAATTGGCA ACACAAGAAC ATGAAAAGCA      3840
TGAACTTTGA CAATCCTGTG TACTTGAAAA CCACTGAAGA GGACCTCTCC ATAGACATTG      3900
GTAGACACAG TGCTTCTGTT GGACACACGT ACCCAGCAAT ATCAGTTGTA AGCACAGATG      3960
ATGATCTAGC TTGACTTCTG TGACAAATGT TGACCTTTGA GGTCTAAACA AATAATACCC      4020
CCGTCGGAAT GGTAACCGAG CCAGCAGCTG AAGTCTCTTT TTCTTCCTCT CGGCTGGAAG      4080
AACATCAAGA TACCTTTGCG TGGATCAAGC TTGGTACCGA GCTCGGATCC ACTAGTAACG      4140
GCCGCCAGTG TGCTGGAATT CTGCAGATAT CCATCACACT GGCGGCCGCG GGATCCAGA      4200
CATGATAAGA TACATTGATG AGTTTGGACA AACCACAACT AGAATGCAGT GAAAAAAATG      4260
CTTTATTTGT GAAATTTGTG ATGCTATTGC TTTATTTGTA ACCATTATAA GCTGCAATAA      4320
ACAAGTTAAC AACAACAATT GCATTCATTT TATGTTTCAG GTTCAGGGGG AGGTGTGGGA      4380
GGTTTTTTCG GATCCTCTAG AGTCGACCTG CAGGCTGATC TGGAAGGTGC TGAGGTACGA      4440
TGAGACCCGC ACCAGGTGCA GACCCTGCGA GTGTGGCGGT AAACATATTA GGAACCAGCC      4500
TGTGATGCTG GATGTGACCG AGGAGCTGAG GCCCGATCAC TTGGTGCTGG CCTGCACCCG      4560
CGCTGAGTTT GGCTCTAGCG ATGAAGATAC AGATTGAGGT ACTGAAATGT GTGGGCGTGG      4620
CTTAAGGGTG GGAAAGAATA TATAAGGTGG GGGTCTTATG TAGTTTTGTA TCTGTTTTGC      4680
AGCAGCCGCC GCCGCCATGA GCACCAACTC GTTTGATGGA AGCATTGTGA GCTCATATTT      4740
GACAACGCGC ATGCCCCCAT GGGCCGGGGT GCGTCAGAAT GTGATGGGCT CCAGCATTGA      4800
TGGTCGCCCC GTCCTGCCCG CAAACTCTAC TACCTTGACC TACGAGACCG TGTCTGGAAC      4860
GCCGTTGGAG ACTGCAGCCT CCGCCGCCGC TTCAGCCGCT GCAGCCACCG CCCGCGGGAT      4920
TGTGACTGAC TTTGCTTTCC TGAGCCCGCT TGCAAGCAGT GCAGCTTCCC GTTCATCCGC      4980
CCGCGATGAC AAGTTGACGG CTCTTTTGGC ACAATTGGAT TCTTTGACCC GGGAACTTAA      5040
TGTCGTTTCT CAGCAGCTGT GGATCTGCG CCAGCAGGTT TCTGCCCTGA AGGCTTCCTC      5100
CCCTCCCAAT GCGGTTTAAA ACATAAATAA AAAACCAGAC TCTGTTTGGA TTTGGATCAA      5160
GCAAGTGTCT TGCTGTCTTT ATTTAGGGGT TTTGCGCGCG CGGTAGGCCC GGGACCAGCG      5220
GTCTCGGTCG TTGAGGGTCC TGTGTATTTT TTCCAGGACG TGGTAAAGGT GACTCTGGAT      5280
GTTCAGATAC ATGGGCATAA GCCCGTCTCT GGGGTGGAGG TAGCACCACT GCAGAGCTTC      5340
ATGCTGCGGG GTGGTGTTGT AGATGATCCA GTCGTAGCAG GAGCGCTGGG CGTGGTGCCT      5400
AAAAATGTCT TTCAGTAGCA AGCTGATTGC CAGGGGCAGG CCCTTGGTGT AAGTGTTTAC      5460
AAAGCGGTTA AGCTGGGATG GGTGCATACG TGGGGATATG AGATGCATCT TGGACTGTAT      5520
TTTTAGGTTG GCTATGTTCC CAGCCATATC CCTCCGGGGA TTCATGTTGT GCAGAACCAC      5580
CAGCACAGTG TATCCGGTGC ACTTGGGAAA TTTGTCATGT AGCTTAGAAG GAAATGCGTG      5640
GAAGAACTTG GAGACGCCCT TGTGACCTCC AAGATTTCC ATGCATTCGT CCATAATGAT      5700
GGCAATGGGC CCACGGGCGG CGGCCTGGGC GAAGATATTT CTGGGATCAC TAACGTCATA      5760
```

```
GTTGTGTTCC  AGGATGAGAT  CGTCATAGGC  CATTTTTACA  AAGCGCGGGC  GGAGGGTGCC    5820
AGACTGCGGT  ATAATGGTTC  CATCCGGCCC  AGGGGCGTAG  TTACCCTCAC  AGATTTGCAT    5880
TTCCCACGCT  TTGAGTTCAG  ATGGGGGGAT  CATGTCTACC  TGCGGGGCGA  TGAAGAAAAC    5940
GGTTTCCGGG  GTAGGGGAGA  TCAGCTGGGA  AGAAAGCAGG  TTCCTGAGCA  GCTGCGACTT    6000
ACCGCAGCCG  GTGGGCCCGT  AAATCACACC  TATTACCGGG  TGCAACTGGT  AGTTAAGAGA    6060
GCTGCAGCTG  CCGTCATCCC  TGAGCAGGGG  GGCCACTTCG  TTAAGCATGT  CCCTGACTCG    6120
CATGTTTTCC  CTGACCAAAT  CCGCCAGAAG  GCGCTCGCCG  CCCAGCGATA  GCAGTTCTTG    6180
CAAGGAAGCA  AAGTTTTCA   ACGGTTTGAG  ACCGTCCGCC  GTAGGCATGC  TTTTGAGCGT    6240
TTGACCAAGC  AGTTCCAGGC  GGTCCACAG   CTCGGTCACC  TGCTCTACGG  CATCTCGATC    6300
CAGCATATCT  CCTCGTTTCG  CGGGTTGGGG  CGGCTTTCGC  TGTACGGCAG  TAGTCGGTGC    6360
TCGTCCAGAC  GGGCCAGGGT  CATGTCTTTC  CACGGGCGCA  GGGTCCTCGT  CAGCGTAGTC    6420
TGGGTCACGG  TGAAGGGGTG  CGCTCCGGGC  TGCGCGCTGG  CCAGGGTGCG  CTTGAGGCTG    6480
GTCCTGCTGG  TGCTGAAGCG  CTGCCGGTCT  TCGCCCTGCG  CGTCGGCCAG  GTAGCATTTG    6540
ACCATGGTGT  CATAGTCCAG  CCCCTCCGCG  GCGTGGCCCT  TGGCGCGCAG  CTTGCCCTTG    6600
GAGGAGGCGC  CGCACGAGGG  GCAGTGCAGA  CTTTTGAGGG  CGTAGAGCTT  GGGCGCGAGA    6660
AATACCGATT  CCGGGGAGTA  GGCATCCGCG  CCGCAGGCCC  CGCAGACGGT  CTCGCATTCC    6720
ACGAGCCAGG  TGAGCTCTGG  CCGTTCGGGG  TCAAAAACCA  GGTTTCCCCC  ATGCTTTTG    6780
ATGCGTTTCT  TACCTCTGGT  TTCCATGAGC  CGGTGTCCAC  GCTCGGTGAC  GAAAGGCTG    6840
TCCGTGTCCC  CGTATACAGA  CTTGAGAGGC  CTGTCCTCGA  CCGATGCCCT  TGAGAGCCTT    6900
CAACCCAGTC  AGCTCCTTCC  GGTGGGCGCG  GGGCATGACT  ATCGTCGCCG  CACTTATGAC    6960
TGTCTTCTTT  ATCATGCAAC  TCGTAGGACA  GGTGCCGGCA  GCGCTCTGGG  TCATTTTCGG    7020
CGAGGACCGC  TTTCGCTGGA  GCGCGACGAT  GATCGGCCTG  TCGCTTGCGG  TATTCGGAAT    7080
CTTGCACGCC  CTCGCTCAAG  CCTTCGTCAC  TGGTCCCGCC  ACCAAACGTT  TCGGCGAGAA    7140
GCAGGCCATT  ATCGCCGGCA  TGGCGGCCGA  CGCGCTGGGC  TACGTCTTGC  TGGCGTTCGC    7200
GACGCGAGGC  TGGATGGCCT  TCCCCATTAT  GATTCTTCTC  GCTTCCGGCG  GCATCGGGAT    7260
GCCCGCGTTG  CAGGCCATGC  TGTCCAGGCA  GGTAGATGAC  GACCATCAGG  GACAGCTTCA    7320
AGGATCGCTC  GCGGCTCTTA  CCAGCCTAAC  TTCGATCACT  GGACCGCTGA  TCGTCACGGC    7380
GATTTATGCC  GCCTCGGCGA  GCACATGGAA  CGGGTTGGCA  TGGATTGTAG  CGCCGCCCT    7440
ATACCTTGTC  TGCCTCCCCG  CGTTGCGTCG  CGGTGCATGG  AGCCGGGCCA  CCTCGACCTG    7500
AATGGAAGCC  GGCGGCACCT  CGCTAACGGA  TTCACCACTC  CAAGAATTGG  AGCCAATCAA    7560
TTCTTGCGGA  GAACTGTGAA  TGCGCAAACC  AACCCTTGGC  AGAACATATC  CATCGCGTCC    7620
GCCATCTCCA  GCAGCCGCAC  GCGGCGCATC  TCGGGCAGCG  TTGGGTCCTG  GCCACGGGTG    7680
CGCATGATCG  TGCTCCTGTC  GTTGAGGACC  CGGCTAGGCT  GGCGGGGTTG  CCTTACTGGT    7740
TAGCAGAATG  AATCACCGAT  ACGCGAGCGA  ACGTGAAGCG  ACTGCTGCTG  CAAAACGTCT    7800
GCGACCTGAG  CAACAACATG  AATGGTCTTC  GGTTTCCGTG  TTTCGTAAAG  TCTGGAAACG    7860
CGGAAGTCAG  CGCCCTGCAC  CATTATGTTC  CGGATCTGCA  TCGCAGGATG  CTGCTGGCTA    7920
CCCTGTGGAA  CACCTACATC  TGTATTAACG  AAGCCTTTCT  CAATGCTCAC  GCTGTAGGTA    7980
TCTCAGTTCG  GTGTAGGTCG  TTCGCTCCAA  GCTGGGCTGT  GTGCACGAAC  CCCCGTTCA    8040
GCCCGACCGC  TGCGCCTTAT  CCGGTAACTA  TCGTCTTGAG  TCCAACCCGG  TAAGACACGA    8100
CTTATCGCCA  CTGGCAGCAG  CCACTGGTAA  CAGGATTAGC  AGAGCGAGGT  ATGTAGGCGG    8160
```

```
TGCTACAGAG  TTCTTGAAGT  GGTGGCCTAA  CTACGGCTAC  ACTAGAAGGA  CAGTATTTGG    8220

TATCTGCGCT  CTGCTGAAGC  CAGTTACCTT  CGGAAAAAGA  GTTGGTAGCT  CTTGATCCGG    8280

CAAACAAACC  ACCGCTGGTA  GCGGTGGTTT  TTTTGTTTGC  AAGCAGCAGA  TTACGCGCAG    8340

AAAAAAAGGA  TCTCAAGAAG  ATCCTTTGAT  CTTTTCTACG  GGGTCTGACG  CTCAGTGGAA    8400

CGAAAACTCA  CGTTAAGGGA  TTTTGGTCAT  GAGATTATCA  AAAGGATCT   TCACCTAGAT    8460

CCTTTTAAAT  TAAAAATGAA  GTTTTAAATC  AATCTAAAGT  ATATATGAGT  AAACTTGGTC    8520

TGACAGTTAC  CAATGCTTAA  TCAGTGAGGC  ACCTATCTCA  GCGATCTGTC  TATTTCGTTC    8580

ATCCATAGTT  GCCTGACTCC  CCGTCGTGTA  GATAACTACG  ATACGGGAGG  GCTTACCATC    8640

TGGCCCCAGT  GCTGCAATGA  TACCGCGAGA  CCCACGCTCA  CCGGCTCCAG  ATTTATCAGC    8700

AATAAACCAG  CCAGCCGGAA  GGGCCGAGCG  CAGAAGTGGT  CCTGCAACTT  TATCCGCCTC    8760

CATCCAGTCT  ATTAATTGTT  GCCGGGAAGC  TAGAGTAAGT  AGTTCGCCAG  TTAATAGTTT    8820

GCGCAACGTT  GTTGCCATTG  CTGCAGGCAT  CGTGGTGTCA  CGCTCGTCGT  TTGGTATGGC    8880

TTCATTCAGC  TCCGGTTCCC  AACGATCAAG  GCGAGTTACA  TGATCCCCA   TGTTGTGCAA    8940

AAAAGCGGTT  AGCTCCTTCG  GTCCTCCGAT  CGTTGTCAGA  AGTAAGTTGG  CCGCAGTGTT    9000

ATCACTCATG  GTTATGGCAG  CACTGCATAA  TTCTCTTACT  GTCATGCCAT  CCGTAAGATG    9060

CTTTTCTGTG  ACTGGTGAGT  ACTCAACCAA  GTCATTCTGA  GAATAGTGTA  TGCGGCGACC    9120

GAGTTGCTCT  TGCCCGGCGT  CAACACGGGA  TAATACCGCG  CCACATAGCA  GAACTTTAAA    9180

AGTGCTCATC  ATTGGAAAAC  GTTCTTCGGG  GCGAAAACTC  TCAAGGATCT  TACCGCTGTT    9240

GAGATCCAGT  TCGATGTAAC  CCACTCGTGC  ACCCAACTGA  TCTTCAGCAT  CTTTTACTTT    9300

CACCAGCGTT  TCTGGGTGAG  CAAAAACAGG  AAGGCAAAAT  GCCGCAAAAA  AGGGAATAAG    9360

GGCGACACGG  AAATGTTGAA  TACTCATACT  CTTCCTTTTT  CAATATTATT  GAAGCATTTA    9420

TCAGGGTTAT  TGTCTCATGA  GCGGATACAT  ATTTGAATGT  ATTTAGAAAA  ATAAACAAAT    9480

AGGGGTTCCG  CGCACATTTC  CCCGAAAAGT  GCCACCTGAC  GTCTAAGAAA  CCATTATTAT    9540

CATGACATTA  ACCTATAAAA  ATAGGCGTAT  CACGAGGCCC  TTTCGTCTTC  AA            9592
```

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:4:

```
TAGTAAATTT  GGGC                                                            14
```

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:5:

```
AGTAAGATTT  GGCC                                                            14
```

(2) INFORMATION FOR SEQ ID NO:6:

(i) SEQUENCE CHARACTERISTICS:
　　　　(A) LENGTH: 14 base pairs
　　　　(B) TYPE: nucleic acid
　　　　(C) STRANDEDNESS: double
　　　　(D) TOPOLOGY: unknown (ii) MOLECULE TYPE: DNA (genomic)

(xi) SEQUENCE DESCRIPTION: SEQ ID NO:6:

AGTGAAATCT GAAT　　　　　　　　　　　　　　　　　　　　　　　　14

(2) INFORMATION FOR SEQ ID NO:7:

(i) SEQUENCE CHARACTERISTICS:
　　　　(A) LENGTH: 14 base pairs
　　　　(B) TYPE: nucleic acid
　　　　(C) STRANDEDNESS: double
　　　　(D) TOPOLOGY: unknown (ii) MOLECULE TYPE: DNA (genomic)

(xi) SEQUENCE DESCRIPTION: SEQ ID NO:7:

GAATAATTTT GTGT　　　　　　　　　　　　　　　　　　　　　　　　14

(2) INFORMATION FOR SEQ ID NO:8:

(i) SEQUENCE CHARACTERISTICS:
　　　　(A) LENGTH: 14 base pairs
　　　　(B) TYPE: nucleic acid
　　　　(C) STRANDEDNESS: double
　　　　(D) TOPOLOGY: unknown (ii) MOLECULE TYPE: DNA (genomic)

(xi) SEQUENCE DESCRIPTION: SEQ ID NO:8:

CGTAATATTT GTCT　　　　　　　　　　　　　　　　　　　　　　　　14